United States Patent
Minskoff et al.

(10) Patent No.: US 10,821,212 B2
(45) Date of Patent: *Nov. 3, 2020

(54) SURGICAL SUCTION DEVICE THAT USES POSITIVE PRESSURE GAS

(71) Applicant: CONMED CORPORATION, Utica, NY (US)

(72) Inventors: Noah Mark Minskoff, Palo Alto, CA (US); James Jackson, Victoria (CA)

(73) Assignee: CONMED CORPORATION, Utica, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,191

(22) Filed: Oct. 19, 2015

(65) Prior Publication Data

US 2017/0014559 A1 Jan. 19, 2017

Related U.S. Application Data

(60) Provisional application No. 62/191,689, filed on Jul. 13, 2015.

(51) Int. Cl.
*A61M 1/00* (2006.01)
*A61B 5/15* (2006.01)
(Continued)

(52) U.S. Cl.
CPC ..... *A61M 1/0027* (2014.02); *A61B 5/150015* (2013.01); *A61B 5/150099* (2013.01);
(Continued)

(58) Field of Classification Search
CPC . A61M 1/0066; A61M 2205/42; A61B 17/00; A61B 2217/005; A61B 2218/008
(Continued)

(56) References Cited

U.S. PATENT DOCUMENTS

| 2,055,577 A | 9/1936 | Huff |
| 2,713,510 A | 7/1955 | Conada |

(Continued)

FOREIGN PATENT DOCUMENTS

| EP | 1757317 A1 | 2/2007 |
| EP | 1909864 A2 | 4/2008 |

(Continued)

OTHER PUBLICATIONS

PCT/US2015/056276 International Search Report and Written Opinion dated Jan. 28, 2016.

(Continued)

*Primary Examiner* — Andrew J Mensh
(74) *Attorney, Agent, or Firm* — Bond, Schoeneck & King, PLLC; Frederick J. M. Price

(57) ABSTRACT

A surgical suction device that uses positive pressure gas is shown and described. The surgical suction device includes an air amplifier. The air amplifier includes a structure defining a generally cylindrical cavity having a first opening at a first end and a second opening at a second end. The cylindrical cavity is defined by an inner wall of the cavity. The air amplifier includes an annular opening in the inner wall near the first end. The annular opening defines a jet opening adapted to allow a pressurized gas to flow out of the annular opening such that a low pressure region is produced at the first end and an amplified flow is produced at the second end. The annular opening is further configured such that the pressurized gas enters the cavity at an angle with respect to the inner wall of the cavity that is towards the second end.

9 Claims, 52 Drawing Sheets

(51) Int. Cl.
  *A61B 10/02* (2006.01)
  *A61M 39/22* (2006.01)
(52) U.S. Cl.
  CPC ....... *A61B 10/0283* (2013.01); *A61M 1/0029* (2014.02); *A61M 1/0035* (2014.02); *A61M 1/0039* (2013.01); *A61M 1/0049* (2013.01); *A61M 1/0052* (2014.02); *A61M 1/0076* (2013.01); *A61M 1/0088* (2013.01); *A61M 39/22* (2013.01); *A61B 5/150221* (2013.01); *A61B 2217/005* (2013.01); *A61B 2218/008* (2013.01); *A61M 1/0056* (2013.01); *A61M 2205/10* (2013.01); *A61M 2205/18* (2013.01); *A61M 2205/183* (2013.01); *A61M 2205/3331* (2013.01); *A61M 2205/42* (2013.01); *A61M 2205/581* (2013.01); *A61M 2205/582* (2013.01); *A61M 2206/10* (2013.01)
(58) Field of Classification Search
  USPC .......................................................... 604/540
  See application file for complete search history.

(56) References Cited

U.S. PATENT DOCUMENTS

| | | | |
|---|---|---|---|
| 2,773,251 A | 12/1956 | Snyder | |
| 3,494,360 A | 2/1970 | Raymond | |
| 3,499,393 A | 3/1970 | Bent | |
| 3,665,682 A | 5/1972 | Ciavattoni et al. | |
| 3,667,069 A | 6/1972 | Blackshear et al. | |
| 3,812,855 A | 5/1974 | Banko | |
| 4,013,089 A * | 3/1977 | Braukmann | E03C 1/106 137/218 |
| 4,046,492 A * | 9/1977 | Inglis | F04F 5/16 417/197 |
| 4,654,029 A | 3/1987 | D'Antonio | |
| 4,838,281 A | 6/1989 | Rogers et al. | |
| 5,055,100 A | 10/1991 | Olsen | |
| 5,108,389 A | 4/1992 | Cosmescu | |
| 5,154,709 A | 10/1992 | Johnson | |
| 5,199,944 A | 4/1993 | Cosmescu | |
| 5,255,412 A | 10/1993 | Mally et al. | |
| 5,318,516 A | 6/1994 | Cosmescu | |
| 5,431,650 A | 7/1995 | Cosmescu | |
| 5,460,602 A | 10/1995 | Shapira | |
| 5,693,044 A | 12/1997 | Cosmescu | |
| 5,836,944 A | 11/1998 | Cosmescu | |
| 5,853,384 A | 12/1998 | Bair | |
| 5,971,956 A | 10/1999 | Epstein | |
| 6,001,077 A * | 12/1999 | Ellman | A61B 18/00 604/19 |
| 6,085,746 A * | 7/2000 | Fox | A61M 16/0096 128/204.19 |
| 6,149,648 A | 11/2000 | Cosmescu | |
| 6,203,321 B1 * | 3/2001 | Helmer | A61C 17/04 433/95 |
| 6,355,034 B2 | 3/2002 | Cosmescu | |
| 6,368,309 B1 | 4/2002 | Yeh | |
| 6,458,125 B1 | 10/2002 | Cosmescu | |
| 6,599,277 B2 | 7/2003 | Neubert | |
| 6,604,694 B1 | 8/2003 | Kordas et al. | |
| 6,635,034 B1 | 10/2003 | Cosmescu | |
| 6,702,812 B2 | 3/2004 | Cosmescu | |
| 7,112,199 B2 | 9/2006 | Cosmescu | |
| 7,276,063 B2 | 10/2007 | Davison et al. | |
| 7,935,109 B2 | 5/2011 | Cosmescu | |
| 8,092,166 B2 | 1/2012 | Nicolas et al. | |
| 8,308,445 B2 | 11/2012 | Gammack et al. | |
| 8,403,650 B2 | 3/2013 | Gammack et al. | |
| 8,414,576 B2 | 4/2013 | Cosmescu | |
| 8,439,874 B2 | 5/2013 | Hertweck | |
| 8,518,018 B2 | 8/2013 | Minskoff et al. | |
| 8,596,990 B2 | 12/2013 | Schaaf | |
| 8,613,601 B2 | 12/2013 | Helps | |
| 8,721,595 B2 | 5/2014 | Stiehl et al. | |
| 8,764,412 B2 | 7/2014 | Gammack et al. | |
| 8,827,945 B2 | 9/2014 | Baker et al. | |
| 8,845,616 B2 | 9/2014 | Minskoff et al. | |
| 8,932,286 B2 | 1/2015 | Terry et al. | |
| 8,932,292 B2 | 1/2015 | Terry et al. | |
| 9,023,002 B2 | 5/2015 | Robinson et al. | |
| 9,119,907 B2 | 9/2015 | Sherman et al. | |
| 2007/0016136 A1 * | 1/2007 | Opie | A61M 1/0043 604/119 |
| 2007/0129722 A1 | 6/2007 | Cosmescu | |
| 2007/0249990 A1 | 10/2007 | Cosmescu | |
| 2007/0259226 A1 | 11/2007 | Sang et al. | |
| 2009/0221948 A1 * | 9/2009 | Szamosfalvi | A61M 1/3672 604/6.07 |
| 2010/0094283 A1 | 4/2010 | Cosmescu | |
| 2010/0241026 A1 | 9/2010 | Boukas | |
| 2012/0114513 A1 | 5/2012 | Simmonds et al. | |
| 2012/0203209 A1 | 8/2012 | Minskoff et al. | |
| 2012/0203223 A1 | 8/2012 | Terry et al. | |
| 2013/0053795 A1 | 2/2013 | Coulthard et al. | |
| 2013/0053796 A1 | 2/2013 | Robinson et al. | |
| 2013/0131580 A1 | 5/2013 | Blackhurst et al. | |
| 2013/0150782 A1 | 6/2013 | Sorensen et al. | |
| 2013/0276751 A1 | 10/2013 | Raasch | |
| 2014/0228839 A1 | 8/2014 | Cosmescu | |
| 2015/0088132 A1 | 3/2015 | Minskoff et al. | |
| 2015/0088133 A1 | 3/2015 | Minskoff et al. | |
| 2015/0088134 A1 | 3/2015 | Minskoff et al. | |
| 2015/0094718 A1 | 4/2015 | Minskoff et al. | |
| 2015/0157773 A1 | 6/2015 | Baker et al. | |
| 2016/0114084 A1 | 4/2016 | Minskoff et al. | |
| 2016/0114085 A1 | 4/2016 | Minskoff et al. | |
| 2016/0114086 A1 | 4/2016 | Minskoff et al. | |
| 2016/0114087 A1 | 4/2016 | Minskoff et al. | |
| 2016/0114088 A1 | 4/2016 | Minskoff et al. | |
| 2016/0178076 A1 * | 6/2016 | Cellemme | F16K 17/02 137/512 |

FOREIGN PATENT DOCUMENTS

| | | |
|---|---|---|
| EP | 2548537 A2 | 1/2013 |
| EP | 2977613 A1 | 1/2016 |
| WO | WO-9623448 A1 | 8/1996 |
| WO | WO-9714364 A1 | 4/1997 |
| WO | WO-2009054732 A1 | 4/2009 |
| WO | WO-2012106543 A1 | 8/2012 |
| WO | WO-2017011024 A1 | 1/2017 |

OTHER PUBLICATIONS

Co-pending U.S. Appl. No. 14/938,731, filed Nov. 11, 2015.
Co-pending U.S. Appl. No. 14/938,733, filed Nov. 11, 2015.
Co-pending U.S. Appl. No. 14/938,736, filed Nov. 11, 2015.
Co-pending U.S. Appl. No. 14/938,742, filed Nov. 11, 2015.
PCT/US2015/57241 International Search Report and Written Opinion dated Jan. 8, 2016.
U.S. Appl. No. 14/921,944 Office Action dated Jun. 29, 2016.
U.S. Appl. No. 14/921,944 Office Action dated Mar. 15, 2016.
U.S. Appl. No. 14/938,731 Office Action dated Aug. 16, 2016.
U.S. Appl. No. 14/938,733 Office Action dated Aug. 15, 2016.
U.S. Appl. No. 14/938,742 Office Action dated Aug. 23, 2016.
U.S. Appl. No. 14/945,366 Office Action dated Jul. 14, 2016.
U.S. Appl. No. 14/945,367 Office Action dated Jul. 13, 2016.
U.S. Appl. No. 14/945,368 Office Action dated Mar. 17, 2016.
U.S. Appl. No. 14/945,370 Office Action dated Mar. 15, 2016.
Chegg Study. Retrieved from http://www.chegg.com/homework-help/questions-and-answers/venturi-tube-tube-constriction--pressure-venturi-tube-measured-attaching-u-shaped-fluid-fi-q1799759 (retrieved Jan. 26, 2017) (2 pgs) (2003).
Co-pending U.S. Appl. No. 15/480,356, filed Apr. 5, 2017.
Co-pending U.S. Appl. No. 15/480,365, filed Apr. 5, 2017.
PCT/US2015/57241 International Preliminary Report on Patentability dated May 4, 2017.
U.S. Appl. No. 14/938,736 Office Action dated Sep. 8, 2016.
U.S. Appl. No. 14/945,367 Office Action dated Feb. 10, 2017.

(56) References Cited

OTHER PUBLICATIONS

U.S. Appl. No. 14/945,368 Office Action dated Jan. 3, 2017.
U.S. Appl. No. 14/945,370 Office Action dated Dec. 30, 2016.

* cited by examiner

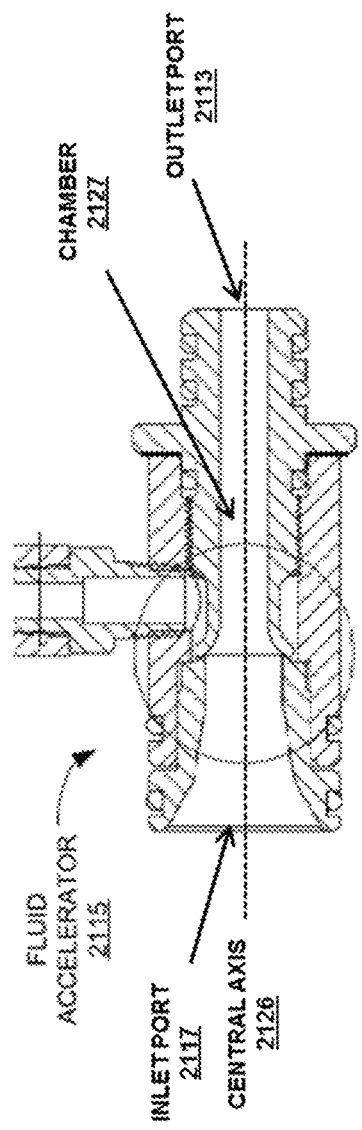
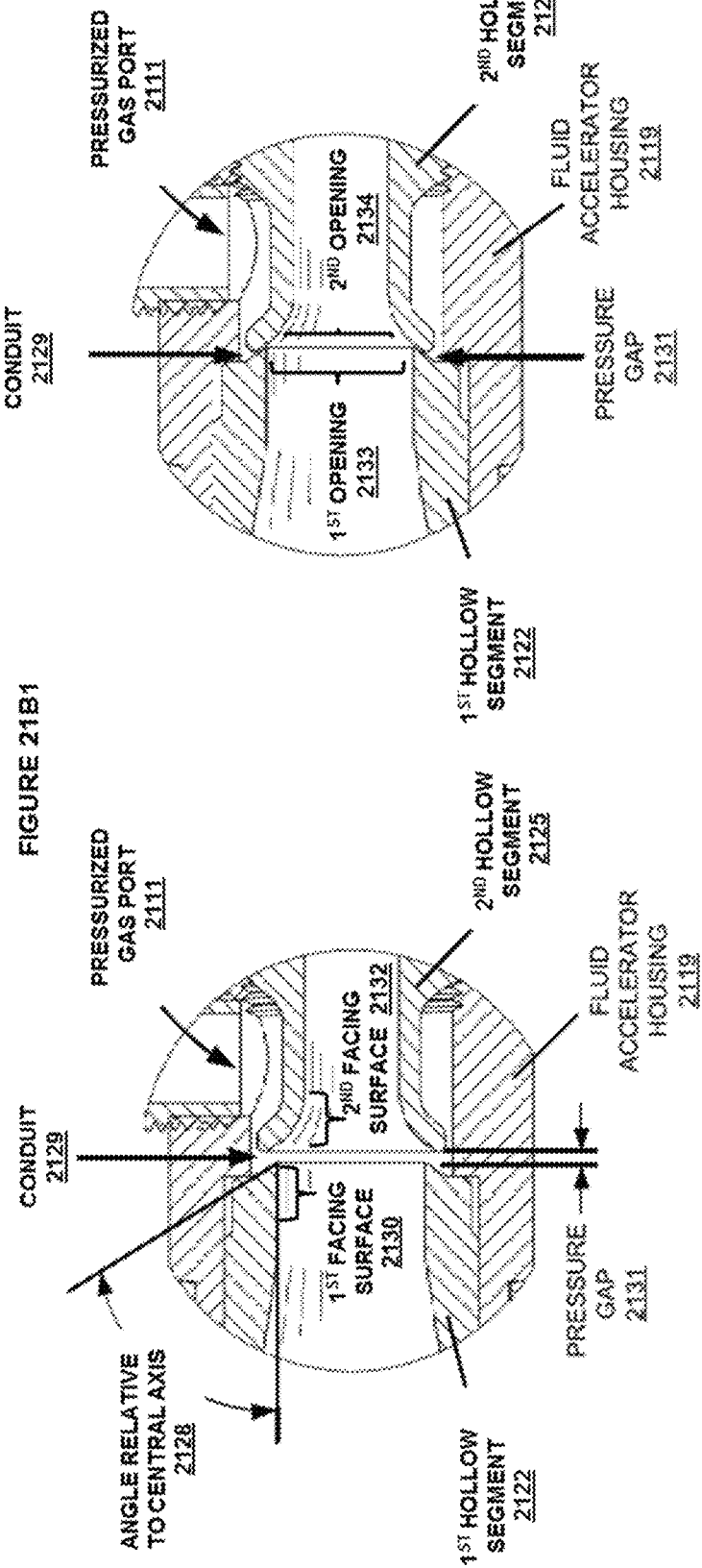

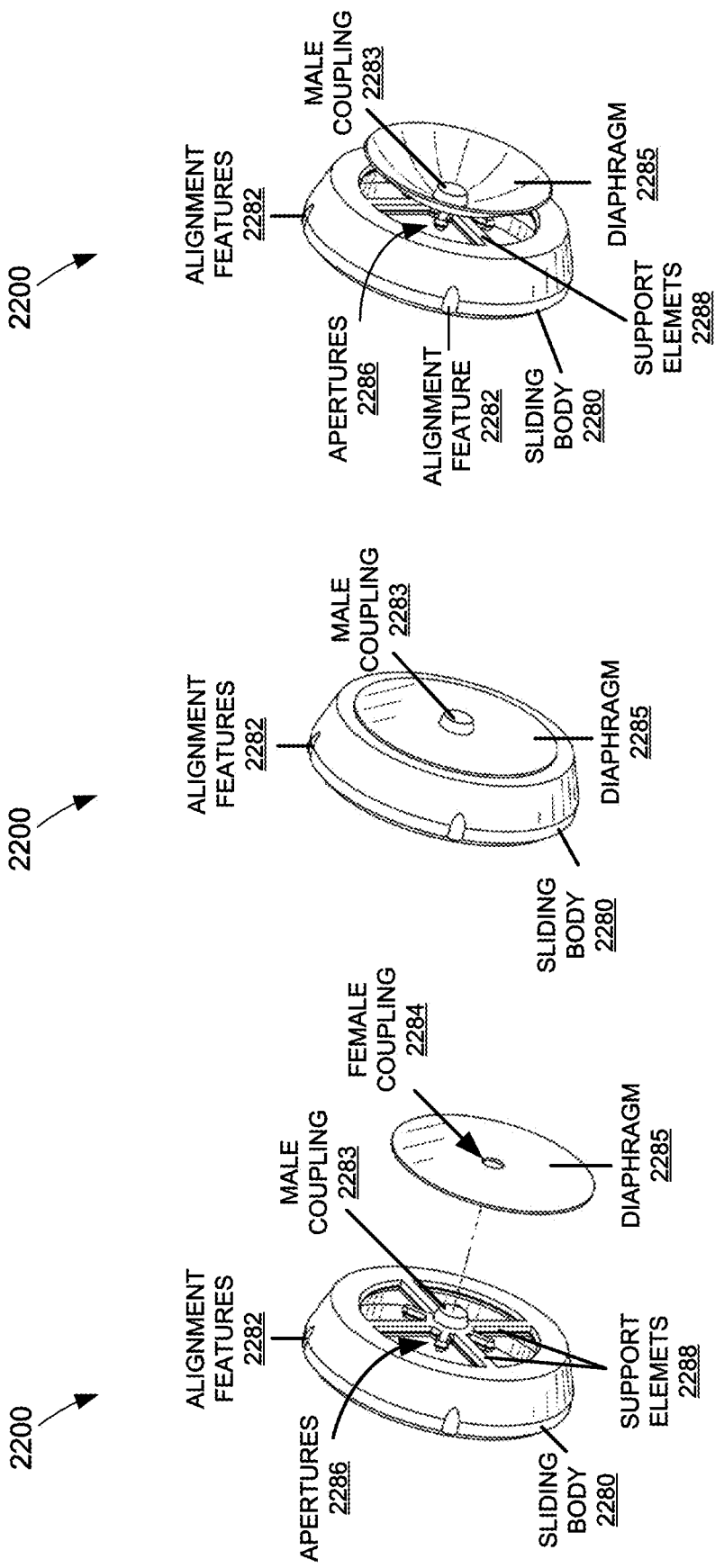

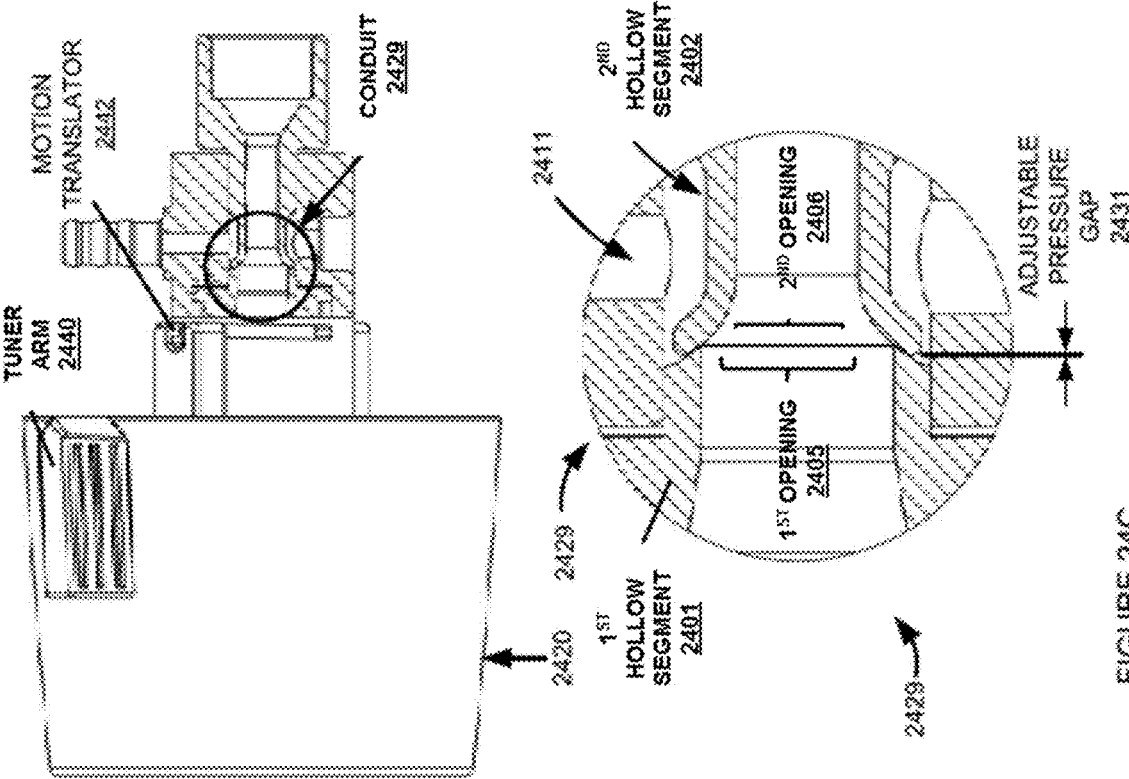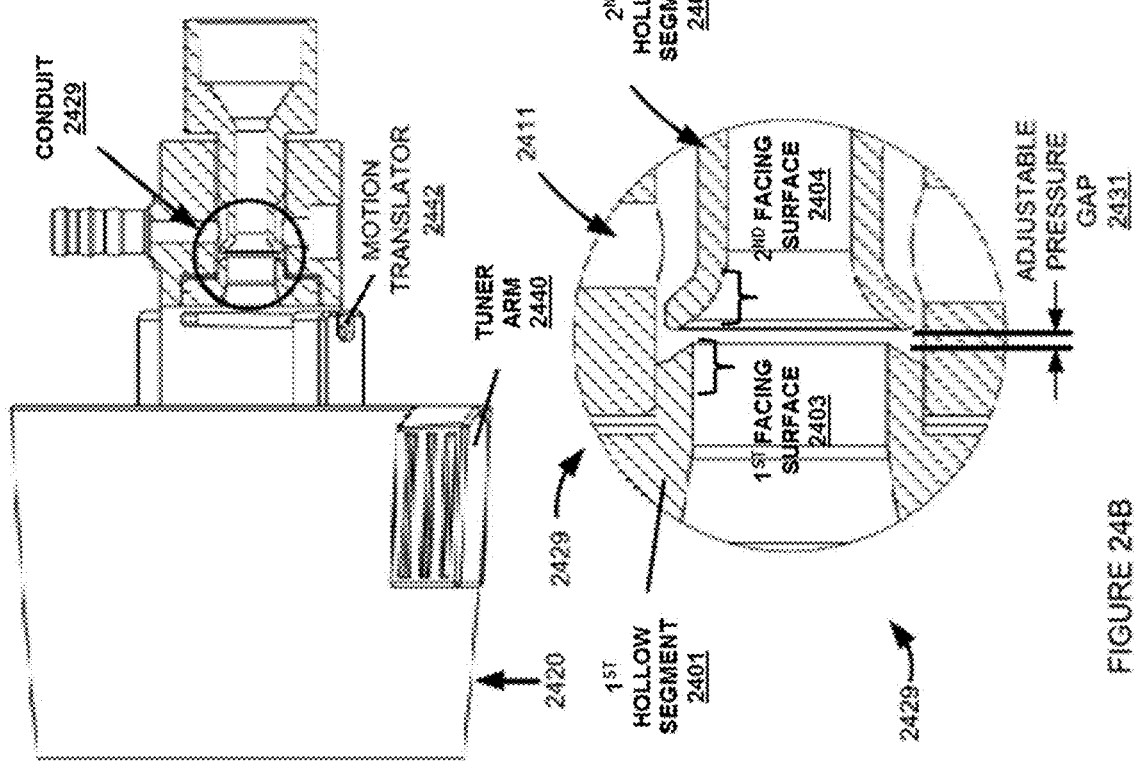

| Device | Device Setting | Smoke Flow Rate [SCFM] | | Static Vacuum [mmHg] |
| --- | --- | --- | --- | --- |
| | | Setup A | Setup B | |
| PULSE Prototype | 43 psi, max gap | 4.3 | 2.8 | 220* |
| | 30 psi, max gap | 3.4 | 2 | 187 |
| | 30 psi, setting 10 | 3.4 | 1.8 | 150 |
| ConMed 1200 | 100%, boost on | 4.1 | - | 116 |
| | 50%, boost on | 2.9 | - | 60 |
| | 100%, boost off | 2.1 | - | 32 |
| | 50%, boost off | 1.5 | - | 18 |
| *Static suction creates internal vortex shedding at this setting | | | | |

Figure 29

| 30 psi input pressure | |
|---|---|
| Room background noise of 43 dB(A) | Device Noise [dB(A)] |
| Device | at 1.5m away |
| PULSE 1.75 gap | 49.4 |
| ConMed AER Defense | 54 |
| Covidien RapidVac | 60 |
| ConMed SES 1200 | 66.5 |

Figure 30

| Air (psi) | Coanda Setting | Vacuum (mmHg) | ΔP (mmHg) | Flow (SCFM) | Notes (Tubing and fittings in use, observations, etc.) |
|---|---|---|---|---|---|
| 30 | 12 | 133 | 19 | 2 | smoke removal testing, 3" blade, tip cover fully retracted |
| 30 | 14 | 118 | 23 | 2.2 | good smoke removal |
| | 10 | 104 | 20 | 2.0-2.1 | |
| | 12 | 117 | 23 | 2.2 | |
| | 10 | 104 | 20 | 2 | blade extending 2 mm from tip |
| | 8 | 86 | 16 | 1.8 | |
| | 6 | 55 | 10.8 | 1.4 | full smoke capture |
| | 4 | 55 | 10.8 | 1.4 | some escape |
| | 3 | 9.8 | 2.7 | 0.5 | 10% smoke loss |
| | | | | | Repeating test with tip cover fully retracted |
| 30 | 14 | 118 | 22.5 | 2.2 | smoke extraction not great |
| 40 | 14 | 173 | 34 | 2.8 | smoke extraction is ok |

Figure 41

|  | Maximum Vacuum [mmHg] |
| --- | --- |
| ConMed AER Defence | 62 |
| Covidien RapidVac | 112 |
| ConMed 1200 | 120 |
| PULSE, Porcine Trial Prototype | 255 |
| PULSE, 55° Prototype | 310 |

Figure 42

| | Smoke Evacuation (Deep Neck of Porcine) * | Smoke Evacuation-Surface Fat * | No Pen * | Fluid (Deep) * | Manufacturer Spec | Maximum Static Vacuum (mmHg) |
|---|---|---|---|---|---|---|
| AER DEFENSE ™ Smoke Evacuator | 57.3 dB | 59 dB | | | <58 dBA | 62 |
| RapidVac™ Smoke Evacuator | | 59.1 dB | | | <54 dBA ** | 112 |
| PULSE and FIRST | 56-57 dB | 58.1 dB | 55.6 dB | 58.8 - 59 dB | TBD | 255 |
| Conmed 1200 | | | | | <65 dBA | 120 |
| PULSE, 55° Prototype | | | | | | |
| *Quiet Room (Equipment turned off, no conversation) | 45.8 dB | | | | | |
| *Baseline Room With conversation | 50-60 dB typical | | | | | |
| *Distance from dB Meter | ~2m | | | | | |
| **Rapid Vac Unit marketing material defined as cart mounted | | | | | | |

Figure 44

SURGICAL SUCTION DEVICE THAT USES POSITIVE PRESSURE GAS

CROSS-REFERENCE

This application claims the benefit of U.S. Provisional Application No. 62/191,689, filed Jul. 13, 2015, which application is incorporated herein by reference.

BACKGROUND

Suction may be generated in a number of ways in a number of different applications. Generally speaking, suction generating devices are used to remove gasses, liquids, or any combination thereof from an environment. Suction is typically generated by electric or motor powered devices which tend to be noisy and cumbersome.

SUMMARY

Described herein are devices, systems, and methods for providing suction. In some embodiments, the suction is generated passively.

Described herein is a surgical suction device that includes an air amplifier. In some embodiments, the air amplifier includes a structure defining a generally cylindrical cavity having a first opening at a first end and a second opening at a second end. In some embodiments, the cylindrical cavity is defined by an inner wall of the cavity. In some embodiments, the air amplifier includes an annular opening in the inner wall near the first end. In some embodiments, the annular opening defines a jet opening adapted to allow a pressurized gas to flow out of the annular opening such that a low pressure region is produced at the first end and an amplified flow is produced at the second end. The annular opening is further configured such that the pressurized gas enters the cavity at an angle with respect to the inner wall of the cavity that is towards the second end. The cavity is flared to a larger diameter where the annular opening communicates with the cavity.

Described herein is a passive suction device comprising a housing comprising a first hollow segment comprising an inlet port configured to receive a gas, a liquid, or a combination thereof; a first opening; and a first outer surface surrounding the first opening; a second hollow segment having an interior and comprising an outlet port configured to release the gas, the liquid, or the combination thereof from the housing; a second opening facing the first opening; and a second outer surface surrounding the second opening and facing the first outer surface; and an airflow amplifier comprising a pressurized gas port configured to receive a pressurized gas flow; and a conduit comprising a gap space between the first outer surface and the second outer surface, wherein the conduit is in fluid continuity with the pressurized gas port, and wherein the conduit is positioned at an angle relative to the second opening in order to receive the pressurized gas flow from the pressurized gas port and direct the pressurized gas flow into the second opening such that when the pressurized gas flow passes into the second hollow segment, the pressurized gas flow travels essentially entirely along one or more interior surfaces of the second hollow segment. In some embodiments, the inlet port further comprises a valve configured to prevent backflow of the gas, the liquid, or the combination thereof. In some embodiments, the passive suction device further comprises an alarm configured to activate in the presence of a backflow of the gas, the liquid, or the combination thereof through the housing. In some embodiments, the alarm port is continuous with the first segment. In some embodiments, the passive suction device further comprises a filter. In some embodiments, the first hollow segment and the second hollow segment are configured to move relative to each other thus changing the distance between the first outer surface and the second outer surface, and thus adjusting the width of the gap space of the conduit. In some embodiments, when the pressurized gas flow travels essentially entirely along one or more surfaces of the hollow interior of the second segment a low pressure area forms within the interior of the second segment thereby creating suction that draws the gas, liquid, solid, or any combination thereof through the inlet port, through the first hollow segment, through the first opening, through the second opening, through the second hollow segment, and through the outlet port. In some embodiments, the conduit is positioned at an angle determined by the angle of the first surface, and wherein the angle of the first surface comprises an angle between 0 degrees and 90 degrees.

Described herein is a method for passively generating suction comprising providing a device comprising a first hollow segment and a second hollow segment; and an airflow amplifier comprising a pressurized gas port configured to receive a pressurized gas flow; and a conduit comprising a gap space between the first hollow segment and the second hollow segment, wherein the conduit is in fluid continuity with the pressurized gas port, and wherein the conduit is positioned to receive the pressurized gas flow from the pressurized gas port and direct the pressurized gas flow into the second opening such that when the pressurized gas flow passes into the second hollow segment, the pressurized gas flow travels essentially entirely along one or more interior surfaces of the second hollow segment. In some embodiments, the device further comprises a valve configured to prevent backflow of the gas, the liquid, or the combination thereof. In some embodiments, the device further comprises an alarm configured to activate in the presence of a backflow of the gas, the liquid, or the combination thereof through the housing. In some embodiments, the device further comprises an alarm port comprising an air powered alarm configured to sound an alarm when a backflow of air passes through the alarm port. In some embodiments, the alarm port is continuous with the first segment. In some embodiments, the device further comprises a filter. In some embodiments, the width of the gap space of the conduit is adjustable. In some embodiments, the flow of pressurized gas through the second hollow segment forms a low pressure area within the interior of the second hollow segment thereby creating suction. In some embodiments, the second hollow segment comprises an opening configured to receive the pressurized gas flow from the conduit, and the conduit is positioned to direct the pressurized gas flow at an angle between 0 degrees and 90 degrees relative to the first hollow segment.

Described herein is a method of passively creating suction using a passive suction device comprising receiving a pressurized gas flow into a conduit of the suction device; and directing the flow of the pressurized gas through a gap space between a first hollow segment and a second hollow segment of the device such that the pressurized gas travels through the second hollow segment and essentially entirely along one or more surfaces of the hollow interior of the second hollow segment thus creating the suction. In some embodiments, the method further comprises adjusting a dimension of the gap space thus modifying the intensity of the suction. In some embodiments, the method further comprises receiving, using the suction, a suction flow comprising a solid, liquid, or mixture thereof. In some embodiments, the method further comprises filtering the suction flow. In some embodiments, the method further comprising sounding an alarm in the presence of a blockage of the suction flow. In some embodiments, the second hollow segment comprises an opening configured to receive the pressurized gas flow from the conduit, and the conduit is positioned to direct the pressurized gas flow at an angle between 0 degrees and 90 degrees relative to the first hollow segment.

Described herein is a method for providing suction during a surgical procedure comprising receiving a suction device configured to passively generate suction by directing a flow of a pressurized gas through the suction device; delivering the pressurized gas to the device thus providing suction during the surgical procedure; and applying the suction to a surgical field thus suctioning a gas, a liquid, a solid, or any combination thereof that result from the surgical procedure. In some embodiments, the method further comprises adjusting the intensity of the suction. In some embodiments, the method further comprises filtering the suctioned gas, the liquid, the solid, or the any combination thereof. In some embodiments, the method further comprises sounding an alarm in the presence of a blockage of the device. In some embodiments, the device is configured to couple with a surgical suction system comprising a canister and a suction tube. In some embodiments, the suction device further comprises a valve configured to prevent backflow of the suctioned gas, liquid, solid, or any combination thereof. In some embodiments, a suction capacity of the device is between about 10 pounds per square inch to about 25 pounds per square inch.

An aspect of the present disclosure provides a passive suction device. The device comprises (a) a first hollow segment having a central axis, wherein the first hollow segment comprises (i) an inlet port configured to receive a gas, a liquid, a solid or any combination thereof (ii) a first opening; and (iii) a first facing surface at least partially surrounding the first opening; (b) a second hollow segment having an interior and comprising (i) an outlet port configured to release the gas, the liquid, the solid or any combination thereof; (ii) a second opening facing the first opening; and (iii) a second facing surface at least partially surrounding the second opening and facing the first outer surface; and (c) an airflow amplifier comprising: (i) a pressurized gas port configured to receive a pressurized gas flow; and (ii) a conduit defined by the first facing surface and the second facing surface. In some embodiments, the conduit is in fluid communication with the pressurized gas port. In some embodiments, the first facing surface comprises an angle less than 90 degrees relative to a central axis of the first hollow segment. In some embodiments, the conduit is configured to receive the pressurized gas flow and direct the pressurized gas flow into the second opening such that the pressurized gas flow through the second opening generates an area of low pressure which generates a suction flow causing the inlet port to receive the gas, the liquid, the solid, or the combination thereof.

In some embodiments, the inlet port further comprises a valve configured to prevent backflow of the gas, the liquid, or the combination thereof. In some embodiments, the device further comprises an alarm configured to activate in the presence of a backflow of the gas, the liquid, or the combination thereof. In some embodiments, the alarm port is in fluid communication with the first segment. In some embodiments, the device further comprises a filter configured to filter the gas, the liquid, the solid, or the combination thereof. In some embodiments, the device further comprises a tuner arm configured to adjust a width of the conduit, wherein the tuner arm is configured to move one or more of the first hollow segment and the second hollow segment relative to each other thus changing a distance between the first facing surface and the second facing surface. In some embodiments, the width of the conduit is adjustable between about 0 millimeters (mm) and about 2 mm. In some embodiments, the device further comprises an angle adjustment controller, wherein the angle adjustment controller is configured to adjust the angle.

An aspect of the present disclosure provides an airflow amplifier. The air amplifier comprises (a) a conduit having a diameter and comprising a first wall and a second wall, and wherein the conduit is configured to receive a pressurized gas flow; (b) a hollow segment in fluid communication with the conduit and having a central axis; and (c) a tuner arm configured to adjust a width of the conduit. In some embodiments, the first wall of the conduit is angled at an angle less than 90 degrees relative to the central axis of the receiving channel. In some embodiments, the conduit is configured to direct a pressurized gas flow into the hollow segment such that the pressurized gas flow through the hollow segment generates an area of low pressure which generates a suction flow and amplifies the flow of the pressurized gas. In some embodiments, the tuner arm is configured to move one or more of the first wall and the second wall relative to each other.

In some embodiments, the amplifier further comprises a chamber wherein the suction flow is generated by the flow of the pressurized gas. In some embodiments, the amplifier further comprises a filter through which the suction flow passes. In some embodiments, the chamber further comprises a flow valve configured to prevent a back flow of the suction flow outside of the chamber. In some embodiments, the amplifier further comprises an alarm configured to sound when a blockage is present in the receiving channel. In some embodiments, the width of the conduit is adjustable between about 0 millimeters (mm) and about 2 mm.

An aspect of the present disclosure provides a suction system. The suction system comprises (a) a pressurized gas; (b) a suction device, comprising (i) a pressurized gas port configured to receive the pressurized gas; (ii) a conduit having a diameter and comprising a first wall and a second wall, and wherein the conduit is configured to receive a pressurized gas flow; (iii) a hollow segment in fluid communication with the conduit and having a central axis; and (c) a canister configured to receive a gas, a liquid, a solid, or combination thereof. In some embodiments, the first wall of the conduit is angled at an angle less than 90 degrees relative to the central axis of the receiving channel. In some embodiments, the conduit is configured to direct a pressurized gas flow into the hollow segment such that the pressurized gas flow through the hollow segment generates an area of low pressure which generates a suction flow. In some embodiments, the canister is in fluid communication with the suction device such that a suction force generated by the suction device is transmitted to the canister causing the canister to receive the gas, the liquid, the solid or the combination thereof.

In some embodiments, the pressurized gas flow conduit has a diameter, and wherein the diameter is adjustable. In some embodiments, the suction device further comprises an alarm configured to sound when a blockage is present in the receiving channel. In some embodiments, the canister is configured to contain the liquid, the solid, or the combination thereof and the gas is suctioned through the canister and into the suction device. In some embodiments, the suction device further comprises a filter through which the suctioned gas is passed through. In some embodiments, the suction system further comprises a tuner arm configured to adjust a width of the conduit, wherein the tuner arm is configured to move one or more of the first wall and the second wall relative to each other.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the subject matter described herein are set forth with particularity in the appended claims. A better understanding of the features and advantages of the present subject matter will be obtained by reference to the following detailed description that sets forth illustrative embodiments, in which the principles of the subject matter described herein are utilized, and the accompanying drawings of which:

FIGS. 21B and 21C are close-up diagrams of FIG. 21B1, illustrating a conduit of a suction device with backflow prevention valve.

FIG. 22A is a diagram illustrating an exploded view of a backflow prevention valve.

FIG. 22B is a diagram illustrating a backflow prevention valve during a blockage.

FIG. 22C is a diagram illustrating a backflow prevention valve during normal operation.

FIG. 24B is a close-up diagram of FIG. 24B1, illustrating the operation of an adjustable pressure gap for a positive pressure operated suction device.

FIG. 24C is a close-up diagram of FIG. 24C1, illustrating the operation of an adjustable pressure gap for a positive pressure operated suction device.

FIG. 29 is a table illustrating different device settings and corresponding values of smoke flow rate in standard cubic feet per minute (scfm) and static vacuum in millimeters of mercury (mmHg).

FIG. 30 is a table illustrating the auditory noise level (dB) of different devices at 30 psi input pressure.

FIG. 41 is a table illustrating different device conditions for smoke evacuation in the porcine trial.

FIG. 42 is a table illustrating maximum static vacuum (mmHg) in the porcine trial.

FIG. 44 is a table illustrating the auditory noise level in decibels (dB) as a function of maximum static vacuum (mmHg) in the porcine trial.

DETAILED DESCRIPTION

Figure 1:
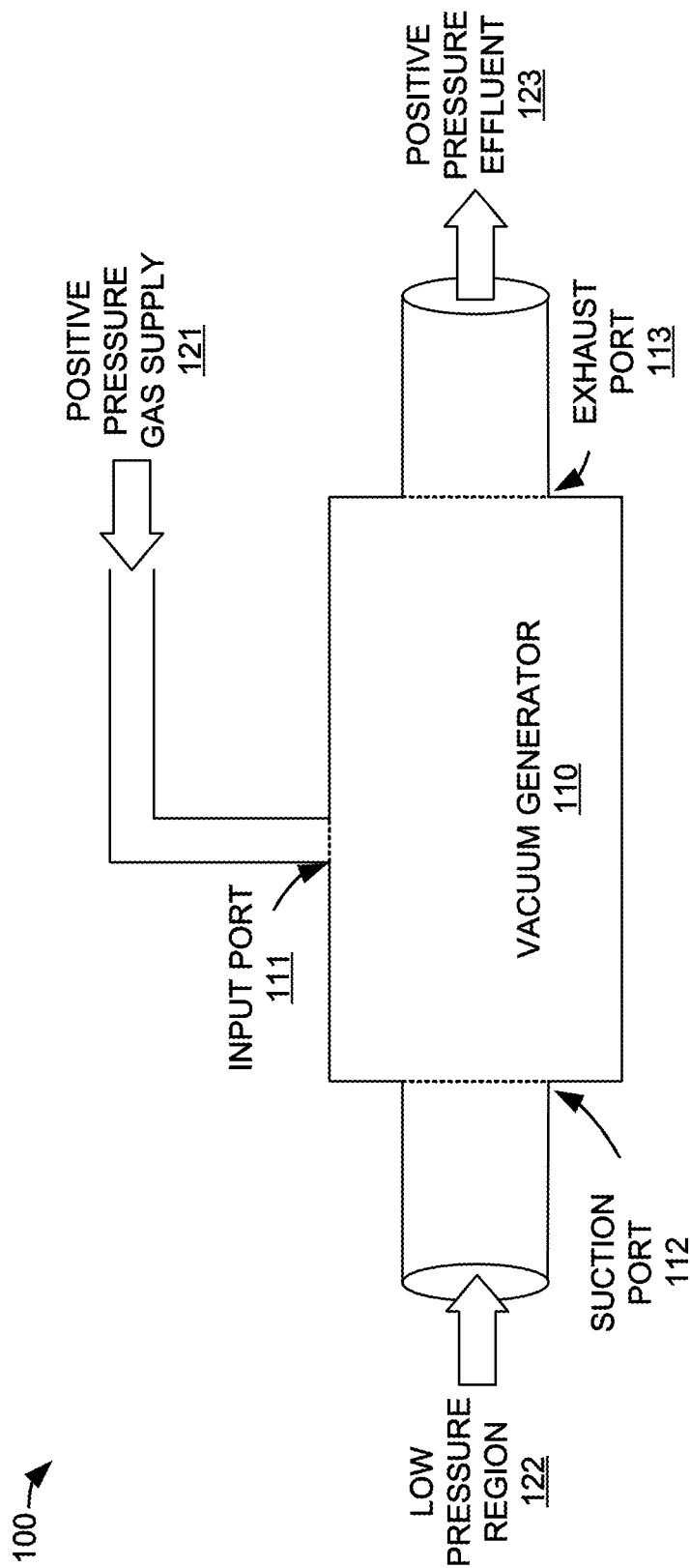
FIG. 1 is a block diagram illustrating a suction system.

Described herein are devices, methods, and systems for generating suction. Before explaining at least one embodiment of the inventive concepts disclosed herein in detail, it is to be understood that the inventive concepts are not limited in their application to the details of construction, experiments, exemplary data, and/or the arrangement of the components set forth in the following description, or illustrated in the drawings. The presently disclosed and claimed inventive concepts are capable of other embodiments or of being practiced or carried out in various ways. Also, it is to be understood that the phraseology and terminology employed herein is for purpose of description only and should not be regarded as limiting in any way.

In the following detailed description of embodiments of the described subject matter, numerous specific details are set forth in order to provide a more thorough understanding of the inventive concepts. However, it will be apparent to one of ordinary skill in the art that the inventive concepts within the disclosure may be practiced without these specific details. In other instances, well-known features have not been described in detail to avoid unnecessarily complicating the instant disclosure.

Further, unless expressly stated to the contrary, "or" refers to an inclusive or and not an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The term "subject" as used herein may refer to a human subject or any animal subject.

Finally, as used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In some embodiments, a suction device for removing medical or surgical byproducts, such as smoke, tissue, and body fluids, uses a Coanda effect based airflow amplifier to create suction. The suction is primarily created by the device from a flow of air or a gas (typically pressurized above ambient) that is provided to the suction device—not an external suction pump (although the device may be used in conjunction with a suction pump). The device may have safety features that prevent the flow of pressurized gas from 'reversing' direction and flowing out of the device in the wrong direction. In other words, the device is configured to prevent the pressurized gas from flowing out the suction end of the device—which may cause problems or injure a patient.

In some embodiments, a one-way valve resides along the airflow path inside the device to ensure the flow of pressurized gas does not flow out the suction end of the device. The one way valve may include to a diversion port configured to allow the pressurized gas to escape to the atmosphere. The one way valve may simply stop all flow through the suction port by isolating the suction port from the air flow amplifier and diverting the pressurized gas out of a diversion port.

In some embodiments, the device may have an alert that is activated when an obstruction, either partially or entirely, blocks an exhaust path used by the device. This alert may be activated by the reversal of flow caused by the obstruction. This alert may be activated by other means (e.g., electronic). In some embodiments, the alert may be activated by the activation of the one-way valve. In some embodiments, the alert may be activated by the flow of the pressurized gas out of a diversion port.

In some embodiments, the alert may include one or more mechanical gauges and/or electronic transducers to measure pressure within the device. The alert may be configured to activate in response to internal pressure within the device reaching a threshold criteria. In some embodiments, the alert may also notify a user of the current internal pressure levels of the suction device and/or whether the internal pressure levels are within the desired operating range.

The alert may be an audible alert, such as a whistle, siren, horn, buzzer, vibration, or any combination thereof. The alert may be a visual alert, such as a constant light or flashing light located on the device. The visual alert may be a lighted button or icon with a symbol or word, such as "Blocked Flow", that may light when the visual alert is activated. The alert may be a mechanical alert, such as a tab, lever, or button that changes position, such as a button that pops or pushes out of the device during an alert or a lever that rotates on the outside of the device during an alert. The device may comprise one or more alerts. The device may comprise one or more visual alerts, audible alerts, mechanical alerts, or any combination thereof.

In some embodiments, a suction device or attachment includes a suction or inlet port disposed towards the distal end of the suction device or attachment. The suction device or attachment also includes a pressurized gas port to receive a first pressurized gas flow. A first air flow amplifier of the suction device or attachment is in fluid communication with the suction port. The air flow amplifier is configured to receive the first pressurized gas flow to produce a first low pressure region. This first low pressure region produces a first flow into the suction port from outside the suction device or attachment. A combined flow of the first pressurized gas flow and the first flow into the suction port pass out of an output port of the first air flow amplifier.

The suction device or attachment may include a filter. This filter receives (and thereby filters) the combined flow. The filter includes at least one filter inlet port and at least one filter output port. The at least one filter inlet port is fluidically connected to a filter media so that air entering the filter passes through a filter media before exiting the at least one filter output port. Accordingly, the combined flow is filtered during its passage through the filter.

In some embodiments, the suction device or attachment may include a second air flow amplifier. The second air flow amplifier is configured to produce a second low pressure region that produces a second flow from a second pressurized gas flow. The second air flow amplifier receives the second pressurized gas flow to produce the second low pressure region. The addition of multiple air flow amplifiers increases the suction capabilities of the suction device. In some embodiments, the second air flow amplifier may be coupled to the first air flow amplifier. In some embodiments, the second air flow amplifier may be configured to compensate for flow and/or pressure (suction) losses attributable to the flow resistance of the filter. For example, the second air flow amplifier may compensate for a portion (e.g., ¼, ½, etc.) or all of the flow resistance of the filter. In another example, the second air flow amplifier may generated suction that exceeds (e.g., 1.25×, 1.5×) the flow resistance of the filter.

In some embodiments, the suction device or attachment may include a backflow preventer. This backflow preventer (e.g., check valve, one-way valve, etc.) can be configured to prevent a flow of pressurized gas from exiting via the suction port. A flow of pressurized gas could exit via the suction port in the event of an obstruction, occlusion, or other blockage of the flow passing via the output port if the backflow preventer is omitted or not activated. An obstruction may occur in the suction device itself, an ancillary pipe, line, or tubing that configured to contain and carry away the materials suctioned-up by the suction device or attachment.

In some embodiments, the suction device or attachment includes an alert. The alert may be activated in response to the backflow preventer becoming activated. In some embodiments, the backflow preventer redirects a pressurized gas flow to a diversion port. In some embodiments, in response to the redirection of the gas flow to a diversion port, the alert is activated. The alert may be audible. The alert may be visual (e.g., an indicator that changes color, shape, etc.) The alert may be mechanical (e.g., a vibration). In some embodiments, the alert comprises a whistle that makes an audible noise when air is passed through it.

In some embodiments, a method for removing surgical byproducts includes receiving a pressurized gas flow by a suction assembly that includes a first air flow amplifier. The pressurized gas flow is provided to the first air flow amplifier. The first air flow amplifier produces a low pressure region that pulls a suction flow into the suction assembly. The suction flow can include surgical byproducts. The suction flow passes from outside the suction assembly into the suction port, through the air flow amplifier, and exits the suction assembly via a positive pressure output (or exhaust) port.

The suction device may weigh less than about 10 kilograms (kg), 5 kg, 4.5 kg, 4 kg, 3.5 kg, 3 kg, 2.5 kg, 2 kg, 1.5 kg, 1 kg, or less. The device may weigh less than about 2 kg. The device may weigh between about 0.5 kg and about 2 kg.

The suction device may have a largest outer diameter of less than about 100 centimeters (cm), 75 cm, 50 cm, 45 cm, 40 cm, 35 cm, 30 cm, 25 cm, 20 cm, 15 cm, 14.5 cm, 14 cm, 13.5 cm, 13 cm, 12.5 cm, 12 cm, 11.5 cm, 11 cm, 10.5 cm, 10 cm, 5.5 cm, 5 cm, or less. A largest outer diameter may be less than about 15 cm. A largest outer diameter may be less than about 12 cm. A largest outer diameter may be less than about 11.5 cm. A largest outer diameter may be between about 5 cm and about 13 cm. A largest outer diameter may be between about 50 cm and 40 cm. A largest outer diameter may be between about 100 cm to about 50 cm.

The suction device may have a largest outer length of about 200 cm, 150 cm, 100 cm, 75 cm, 60 cm, 55 cm, 50 cm, 45 cm, 44 cm, 43 cm, 42 cm, 41 cm, 40 cm, 39 cm, 38 cm, 37 cm, 36 cm, 35 cm, 34 cm, 33 cm, 32 cm, 31 cm, 30 cm, 29 cm, 28 cm, 27 cm, 26 cm, 25 cm, 20 cm or less. The device may have a largest outer length of less than about 45 cm. The device may have a largest outer length of less than about 40 cm. The device may have a largest outer length of about 39 cm. The device may have a largest outer length of between about 40 cm and about 20 cm. The device may have a largest outer length of between about 200 cm and about 50 cm.

The suction device may have a largest outer width of about 50 cm, 45 cm, 40 cm, 35 cm, 30 cm, 25 cm, 24 cm, 23 cm, 22 cm, 21 cm, 20 cm, 19 cm, 18 cm, 17 cm, 16 cm, 15 cm, 14 cm, 13 cm, 12 cm, 11 cm, 10 cm, 9 cm, 8 cm, 7 cm, 6 cm, 5 cm, or less. The device may have a largest outer width of less than about 20 cm. The device may have a largest outer width of less than about 19 cm. The device may have a largest outer width of between about 20 cm and about 15 cm. The device may have a largest outer width of between about 50 cm and about 20 cm.

In some embodiments, a suction device comprises a hollow housing. In some embodiments, the hollow housing may comprise one or more metals, one or more polymers, one or more plastics, one or more ceramics, or one or more composites or any combination thereof. The device may comprise one or more FDA-approved materials. The device may comprise one or more materials with good machining properties or machinability. The device may comprise one or more materials with a low coefficient of friction, such as less than 0.25, less than 0.2, less than 0.15, less than 0.1, or less. The device may comprise one or more materials with a high tensile strength such as greater than 6,000 pounds per square inch (psi), greater than 7,000 psi, greater than 8,000 psi, greater than 9,000 psi or greater.

The device may comprise one or more polymers. The device may comprise one or more copolymers. The device may comprise acrylonitrile-butadiene-styrene (ABS). The device may comprise a polyacetal. For example, the device may comprise a polyacetal of formaldehyde, such as acetal (polyoxymethylene). The device may comprise one or more plastics. The device may comprise a polymer that comprises siloxane, such as silicone oil, silicone rubber, silicone resin, or silicone caulk, or any combination thereof. For example, one or more valves of a device may comprise silicone. The device may comprise polystyrene, polyethylene, sintered glass, borosilicate glass, glass fibers, nylon, polyamide (PA), polyethersufone (PES), polytetrafluoroethylene (PTFE), surfactant-free cellulose acetate (SFCA), regenerated cellulose (RC), polyvinylidene fluoride (PVDF) or any combination thereof. In some embodiments, the device may comprise one or more materials for sound deadening such as sound dampening (i.e. prevent vibrations), sound absorbing (i.e. absorbing the noise), sound attenuation (i.e. reduced sound energy), or any combination thereof. The device may comprise a geometry that aids in sound dampening, sound absorption, sound attenuation, or any combination thereof.

The device may comprise a laminate layer, surface microarchitecture, or combination thereof to aid in sound dampening, sound absorption, sound attenuation, or any combination thereof. The device may comprise an anechoic tile, fiber glass batting, a polyurethane foam, a porous foam (such as a rubber foam), a melamine foam (such as formaldehyde-melamine-sodium bisulfite copolymer), hair felt, a resonant absorber, a Helmholtz resonator, or any combination thereof. The device may comprise acoustic decoupling alone or in combination with one or more materials for sound dampening.

In some embodiments, a suction device housing comprises one or more hollow segments. In some embodiments, a suction device housing may comprise one or more hollow segments positioned essentially in line with one another. In some embodiments, one or more segments of a device may be positioned in multiple different orientations including as a stack or other similar conformation, for example, four hollow segments may be arranged in two stacks of two hollow segments. In some embodiments, one or more hollow segments are configured to communicate such that the one or more hollow segments are continuous. In some embodiments, one or more hollow segments are fluidly continuous such that, for example, a flow of suction may travel from one hollow segment to another. In some embodiments, one or more hollow segments are configured to communicate such that, for example, a flow of a suctioned gas, liquid, solid, or any combination thereof may travel from one hollow segment to another. In some embodiments, a hollow segment of the housing may further comprise other components including ports. For example, in some embodiments, a first hollow segment of a suction device housing comprises an inlet port, which may further comprises an external coupler or connector for coupling with, for example, suction tubing. In some embodiments, a first hollow segment of a device housing comprises an alarm port which comprises an alarm configured to sound when the device is not functioning properly due to, for example, a blockage. In some embodiments, one or more hollow segments comprise one or more holes configured and positioned to facilitate communication with one or more other hollow segments. In some embodiments, a first hollow segment is positioned in line with a second hollow segment, the first hollow segment comprises a first hole that is continuous with the interior of the first hollow segment, the second hollow segment comprises a second hole that is continuous with the interior of the second hollow segment, and the first hole is positioned so that it faces and is aligned or essentially aligned with the second hole. In some embodiments, one or more hollow segments may be tubular in shape. In some embodiments, one or more hollow segments may be in the shape of any polygon including, for example, cuboidal or spherical in shape. In some embodiments, a hole in a hollow segment may be round. In some embodiments, a hole in a hollow segment may comprise any shape including, for example, an oval, a square, a rectangle, or a triangle. In some embodiments, a housing further comprises one or more airflow amplifier mechanisms. A first segment, second segment, third segment, or any additional segment of the device may comprise, for example, a cylindrical shape, a square shape, a rectangular shape, a hexagonal shape, a triangular shape, a spiral shape, a trapezoidal shape, an elliptical shape, or any combination thereof. A portion of a hollow segment may comprise a cylindrical shape, a square shape, a rectangular shape, a hexagonal shape, a triangular shape, a spiral shape, a trapezoidal shape, an elliptical shape, or any combination thereof. A hollow segment may comprise more than one shape. A first hollow segment, second hollow segment, third hollow segment, or any additional segment of the device may comprise a geometry that aids in sound deadening or dampening. For example, a portion of an inner wall of the housing may comprise a surface microarchitecture to aid in sound deadening. A portion of an inner wall of the housing may comprise a laminate layer comprising a material with sound absorptive properties or a laminate layer comprising a surface microarchitecture to aid in sound deadening or a combination thereof. In some embodiments, a portion of the inner wall may comprise sound baffles. In some embodiments, portion of the inner wall may comprise a labyrinth geometry, a hexagonal geometry, convex-shaped geometry, honeycomb geometry, or any combination thereof.

In some embodiments, a suction device comprises an airflow amplifier mechanism. In some embodiments, an airflow amplifier mechanism is a component of one or more of the hollow segments. In some embodiments, an airflow amplifier is not part of a hollow segment. In some embodiments, a first hole in a first hollow segment is continuous with a second hole in a second hollow segment. In some embodiments, a first hole in a first hollow segment is in fluid continuity with a second hole in a second hollow segment and the first hollow segment and the second hollow segment are physically separated by a gap space. In some embodiments, a first hollow segment and a second hollow segment are in fluid continuity but separated by a gap space, and the first hole of the first segment does not cover the entire surface of the first hollow segment so that there is an area of solid surface on the outside of the first hollow segment that at least partially surrounds the first hole. Likewise, in some embodiments, a first hollow segment and a second hollow segment are in fluid continuity but separated by a gap space, and the second hole of the second segment does not cover the entire surface of the second hollow segment so that there is an area of solid surface on the outside of the second hollow segment that at least partially surrounds the second hole. In some embodiments, the gap space between the outer surface surrounding the first hole and the outer surface surrounding the second hole of the second hollow forms a conduit. In this embodiment, the conduit comprises a first wall comprising the outer surface surrounding the first hole, a second wall comprising the outer surface surrounding the second hole on of the second hollow, and a gap space between the two walls. In some embodiments, the conduit is part of an air flow amplifier mechanism that is configured to passively generate suction within the housing that may be further transmitted outside of the housing.

In some embodiments, an airflow amplifier is at least partially contained within a suction device housing. In some embodiments, an airflow amplifier comprises a mechanism for generating an area of low pressure within the housing relative to ambient pressure that then generates a suction force. In some embodiments, an airflow amplifier causes a jet stream of a pressurized gas to travel essentially entirely along one or more inner surfaces of a hollow segment of the device housing. When the airflow amplifier causes a jet stream of a pressurized gas to travel essentially entirely along one or more inner surfaces of a hollow segment of the device housing, a low pressure area is created within the interior of the hollow segment of the device. In some embodiments, when the low pressure area is created it generates a suction force directed essentially in the same direction as the jet stream. In some embodiments, a suction force generated by the jet stream creates suction at an inlet port in the housing. In some embodiments, the airflow amplifier comprises a mechanism for directing a pressurized gas flow stream. In some embodiments, an airflow amplifier comprises a conduit in continuity with a pressurized gas flow port, wherein the conduit is configured to receive a pressurized gas from the pressurized gas flow port. In some embodiments, the conduit is positioned between a first hollow segment and a second hollow segment within the housing, and said conduit is configured to be fluidly continuous with the a hole in the second hollow segment. In some embodiments, the conduit comprises a first wall comprising the outer surface surrounding the first hole, a second wall comprising the outer surface surrounding the second hole on of the second hollow, and a gap space between the two walls. In some embodiments, the gap space may comprise an annular shape. In non-limiting exemplary embodiments, the gap space may comprise any shape including a cuboidal shape, a rectangular shape, and a triangular shape. In some embodiments, the conduit of the air amplifier mechanism and the second hole are positioned relative to each other so that a pressurized gas flow travels from the conduit into second hole. In some embodiments, the conduit and the second hole are positioned relative to each other so that a pressurized gas flow travels through the conduit and into the second hollow space. In some embodiments, the conduit and the second hole are positioned relative to each other such that a pressurized gas flow travels through the conduit and then into the second hollow space, wherein the pressurized gas forms a jet flow that travels essentially entirely along one or more inner surfaces of the second hollow segment creating an area of low pressure adjacent to the jet stream in accordance with the Coanda effect. In this embodiment, the generated low pressure region within the second hollow segment draws a flow of higher pressure air into the second hollow segment from the first hollow segment and the environment outside of the suction device which comprises a suction flow or suction force. In this embodiment, the suction flow or force is transmitted through the second hollow segment, through the gap space (between the first hole and the second hole), through the first hollow segment, and through an inlet port. In some embodiments, the first hollow space includes an inlet or suction port through which suction generated by the air flow amplifier mechanism and the second hollow segment is transmitted outside of the device. In some embodiments, the device may be configured to provide a suction force that suctions gasses, liquids, solids, or any combination thereof including, for example, vapors. This suction force may pull or push a) a portion of matter, b) a portion of pressurized gas, or c) a combination thereof through the device. This suction force may pull or push a portion of matter, a portion of pressurized gas, or combination thereof through one or more filters. The pushing or pulling may depend on the placement of the conduit relative to the location of the suction flow or matter or pressurized gas.

In some embodiments, the conduit of the air amplifier mechanism is positioned at an angle between about 0 degrees and 90 degrees relative to the second hole of the air amplifier. In some embodiments, the conduit of the air amplifier mechanism is positioned at an angle between about 90 degrees and 180 degrees relative to the second hole of the air amplifier. In some embodiments, the conduit of the air amplifier mechanism is positioned at about a 180 degree angle relative to the second hole of the air amplifier. In some embodiments, the conduit of the air amplifier mechanism is positioned at about a 175 degree angle relative to the second hole of the air amplifier. In some embodiments, the conduit of the air amplifier mechanism is positioned at about a 170 degree angle relative to the second hole of the air amplifier. In some embodiments, the conduit of the air amplifier mechanism is positioned at about a 165 degree angle relative to the second hole of the air amplifier. In some embodiments, the conduit of the air amplifier mechanism is positioned at about a 160 degree angle relative to the second hole of the air amplifier. In some embodiments, the conduit of the air amplifier mechanism is positioned at about a 155 degree angle relative to the second hole of the air amplifier. In some embodiments, the conduit of the air amplifier mechanism is positioned at about a 150 degree angle relative to the second hole of the air amplifier. In some embodiments, the conduit of the air amplifier mechanism is positioned at about a 145 degree angle relative to the second hole of the air amplifier. In some embodiments, the conduit of the air amplifier mechanism is positioned at about a 140 degree angle relative to the second hole of the air amplifier. In some embodiments, the conduit of the air amplifier mechanism is positioned at about a 135 degree angle relative to the second hole of the air amplifier. In some embodiments, the conduit of the air amplifier mechanism is positioned at about a 130 degree angle relative to the second hole of the air amplifier. In some embodiments, the conduit of the air amplifier mechanism is positioned at about a 125 degree angle relative to the second hole of the air amplifier. In some embodiments, the conduit of the air amplifier mechanism is positioned at about a 120 degree angle relative to the second hole of the air amplifier. In some embodiments, the conduit of the air amplifier mechanism is positioned at about a 115 degree angle relative to the second hole of the air amplifier. In some embodiments, the conduit of the air amplifier mechanism is positioned at about a 110 degree angle relative to the second hole of the air amplifier. In some embodiments, the conduit of the air amplifier mechanism is positioned at about a 105 degree angle relative to the second hole of the air amplifier. In some embodiments, the conduit of the air amplifier mechanism is positioned at about a 100 degree angle relative to the second hole of the air amplifier. In some embodiments, the conduit of the air amplifier mechanism is positioned at about a 95 degree angle relative to the second hole of the air amplifier. In some embodiments, the conduit of the air amplifier mechanism is positioned at about a 90 degree angle relative to the second hole of the air amplifier. In some embodiments, the conduit of the air amplifier mechanism is positioned at about a 85 degree angle relative to the second hole of the air amplifier. In some embodiments, the conduit of the air amplifier mechanism is positioned at about a 80 degree angle relative to the second hole of the air amplifier. In some embodiments, the conduit of the air amplifier mechanism is positioned at about a 75 degree angle relative to the second hole of the air amplifier. In some embodiments, the conduit of the air amplifier mechanism is positioned at about a 70 degree angle relative to the second hole of the air amplifier. In some embodiments, the conduit of the air amplifier mechanism is positioned at about a 65 degree angle relative to the second hole of the air amplifier. In some embodiments, the conduit of the air amplifier mechanism is positioned at about a 60 degree angle relative to the second hole of the air amplifier. In some embodiments, the conduit of the air amplifier mechanism is positioned at about a 55 degree angle relative to the second hole of the air amplifier. In some embodiments, the conduit of the air amplifier mechanism is positioned at about a 50 degree angle relative to the second hole of the air amplifier. In some embodiments, the conduit of the air amplifier mechanism is positioned at about a 45 degree angle relative to the second hole of the air amplifier. In some embodiments, the conduit of the air amplifier mechanism is positioned at about a 40 degree angle relative to the second hole of the air amplifier. In some embodiments, the conduit of the air amplifier mechanism is positioned at about a 35 degree angle relative to the second hole of the air amplifier. In some embodiments, the conduit of the air amplifier mechanism is positioned at about a 30 degree angle relative to the second hole of the air amplifier. In some embodiments, the conduit of the air amplifier mechanism is positioned at about a 25 degree angle relative to the second hole of the air amplifier. In some embodiments, the conduit of the air amplifier mechanism is positioned at about a 20 degree angle relative to the second hole of the air amplifier. In some embodiments, the conduit of the air amplifier mechanism is positioned at about a 15 degree angle relative to the second hole of the air amplifier. In some embodiments, the conduit of the air amplifier mechanism is positioned at about a 10 degree angle relative to the second hole of the air amplifier. In some embodiments, the conduit of the air amplifier mechanism is positioned at about a 5 degree angle relative to the second hole of the air amplifier. In some embodiments, the conduit of the air amplifier mechanism is positioned at about a 0 degree angle relative to the second hole of the air amplifier.

A beveled end of one segment with an angle between about 0° and 90° can be placed adjacent to a flared end of second segment with an angle between about 90° and about 180° such that the gap space between the two forms a conduit. The beveled end of one segment and the flared end of the second segment may be substantially parallel to one another to enhance laminar flow within the conduit. The angle of the beveled end of a first segment may match the angle of the flared end of a second segment. The angle of the beveled end of a first segment may be similar to the angle of the flared end of a second segment. For example, the beveled end of the first segment may be about 90° and the flared end of the second segment may be about 90°. The beveled end of the first segment may be about 55° and the flared end of the second segment may be about 125°. The beveled end of the first segment may be about 35° and the flared end of the second segment may be about 145°. The flared end may comprise a smooth or rounded edge to enhance or permit laminar flow through the conduit.

A conduit may also be formed by placing a beveled end of one segment with an angle between 0° and 90° adjacent to a second segment with a beveled end angled at between about 90° and about 180°. For example, the beveled end of the first segment may be about 90° and the beveled end of the second segment may be about 90°. The beveled end of the first segment may be about 55° and the beveled end of the second segment may be about 125°. The beveled end of the first segment may be about 35° and the beveled end of the second segment may be about 145°.

A beveled end may be beveled at about a 90 degree)(° angle or less relative to a central axis. A beveled end may be beveled at 90°, 85°, 80°, 75°, 70°, 65°, 60°, 55°, 50°, 45°, 40°, 35°, 30°, 25°, 20°, 15°, 10°, 5° or less. A beveled end may be beveled at about 55° relative to a central axis. A beveled end may be beveled at about 35° relative to a central axis. A beveled end may be beveled at between about 55° to about 35° relative to a central axis. A beveled end may be beveled at between about 60° to about 20° relative to a central axis.

A beveled end may be beveled at about a 90 degree)(° angle or more relative to a central axis. A beveled end may be beveled at 90°, 95°, 100°, 105°, 110°, 115°, 120°, 125°, 130°, 135°, 140°, 145°, 150°, 155°, 160°, 165°, 170°, 175°, or about 180°. A beveled end may be beveled at about 125° relative to a central axis. A beveled end may be beveled at about 145° relative to a central axis. A beveled end may be beveled at between about 125° to about 145° relative to a central axis. A beveled end may be beveled at between about 120° to about 160° relative to a central axis.

A flared end may be flared at about a 90 degree)(° angle or more relative to a central axis. A flared end may be flared at about 90°, 95°, 100°, 105°, 110°, 115°, 120°, 125°, 130°, 135°, 140°, 145°, 150°, 155°, 160°, 165°, 170°, 175°, or about 180°. A flared end may be flared at about 125° relative to a central axis. A flared end may be flared at about 145° relative to a central axis. A flared end may be flared at between about 125° to about 145° relative to a central axis. A flared end may be flared at between about 120° to about 160° relative to a central axis.

A flared end may create an angle relative to a central axis that may be less than about 90 degree. A flared end may create an angle relative to a central axis that may be about 90°, 85°, 80°, 75°, 70°, 65°, 60°, 55°, 50°, 45°, 40°, 35°, 30°, 25°, 20°, 15°, 10°, 5° or less. A flared end may create an angle relative to a central axis that may be about 55°. A flared end may create an angle relative to a central axis that may be about 35°. A flared end may create an angle relative to a central axis that may be between about 55° to about 35°. A flared end may create an angle relative to a central axis that may be between about 60° to about 20°.

A bevel may begin at one end of a segment and continue to an opposite end of the segment. A bevel may comprise a portion of the length of the segment. For example, the portion of the length of the segment that is beveled may be less than about 1%, 2%, 3%, 4%, 5%, 6%, 7%, 8%, 9%, 10%, 15%, 20%, 25%, 30%, 35%, 40%, 45%, 50% or less. The portion of the length that is beveled may be less than about 25%. The portion of the length that is beveled may be less than about 15%. The portion of length that is beveled may be less than about 10%. The portion of length that is beveled may be less than about 5%. The portion of length that is beveled may be less than about 1%.

A flare may begin at one end of a segment and continue to an opposite end of the segment. A flare may comprise a portion of the length of the segment. For example, the portion of the length of the segment that is flared may be less than about 1%, 2%, 3%, 4%, 5%, 6%, 7%, 8%, 9%, 10%, 15%, 20%, 25%, 30%, 35%, 40%, 45%, 50% or less. The portion of the length that is flared may be less than about 25%. The portion of the length that is flared may be less than about 15%. The portion of length that is flared may be less than about 10%. The portion of length that is flared may be less than about 5%. The portion of length that is flared may be less than about 1%.

The angle of one or more beveled ends, one or more flared ends, or any combination thereof may be adjustable. A user may, for example, may adjust one or more angles. The angle may be adjusted automatically, for example, from a remote location. The angle may be adjusted according to a feedback mechanism such as the suction capacity at the inlet port. The user may mechanically rotate a tuner arm to adjust the angle.

One or both ends of a segment can be flared, beveled, angled, sloped, or graded. For example, a segment can have a first end and a second end, one of which or both of which can be beveled. A segment can have a first end and a second end, one of which or both of which can be flared. A segment can have a first beveled end and a second flared end. One or more segments can be placed adjacent to one another in series, for example, having a flared end placed adjacent to a beveled end or having a beveled end placed adjacent to a different beveled end. A segment having two flared ends can be placed in series with two additional segments, by placing a beveled end of each additional segment adjacent to one of the two flared ends of the segment.

In some embodiments, the pressurized gas port (such as a positive pressure intake) that provides the pressurized gas may be located adjacent to any point along the outside of the housing. In some embodiments, the pressurized gas port may be located at a point distal to the air amplifier along the housing (wherein the proximal end of the device comprises the end having the inlet port). In some embodiments, the pressurized gas port may be located at a point proximal to the air amplifier (wherein the proximal end of the device comprises the end having the inlet port. In some embodiments the gas port may be located adjacent to an inlet port (such as a nozzle). In some embodiments, the gas port may be located adjacent to an outlet port (such as a pressurized waste port). In some embodiments, the gas port may be located at any point along the length of a conduit.

In some embodiments, one or more components of an air amplifier mechanism are adjustable. A user may, for example, adjust the width of the gap space of the conduit of the air amplifier by, for example moving one or more of the first hollow segment and second hollow segment relative to each other (i.e. thus moving the walls of the conduit relative to each other). In some embodiments, the width of the gap space of the conduit may be adjusted automatically, for example, from a remote location. The width of the gap space of the conduit may be adjusted according to a feedback mechanism such as the amount of matter at the inlet port or the liquid suction capacity at the inlet port. The user may mechanically rotate a tuner arm to adjust the width of the gap space of the conduit. The tuner arm may be operatively coupled to a groove such as, for example a helical groove that may create a linear movement to adjust the width of the gap space of the conduit.

Reducing the width of the gap space of the conduit may increase the liquid suction capacity. Increasing the width of the gap space of the conduit may reduce the liquid suction capacity. Gas suction capacity may remain constant over the tuner arm adjustment range or over the range of adjustable widths for the one or more gap spaces of the conduits. A volumetric ratio of gas suction to liquid suction at the inlet port (such as a nozzle) may be adjustable over the range of widths for the gap space of the conduit or over the range of tuner arm adjustments. The tuner arm may comprise a continuous rotation or may comprise discrete groves that correspond to specific widths of the gap space of the conduit.

The length of the conduit may be less than about 40%, 35%, 30%, 25%, 20%, 15%, 14%, 13%, 12%, 11%, 10%, 9%, 8%, 7%, 6%, 5%, 4%, 3%, 2%, 1% or less than the length of the first segment or the second segment. The length of the conduit may be less than about 10% the length of the first or second segment. The length of the conduit may be less than about 20% the length of the first or second segment. The length of the conduit may be between about 1% and about 10% the length of the first or second segment. The length of the conduit may be between about 1% and about 5% the length of the first or second segment. The length of the conduit may be between about 1% and about 15% the length of the first or second segment. The length of the conduit may be between about 1% and about 20% the length of the first or second segment.

In some embodiments, the width of the gap space of the conduit may be less than about 10 centimeters (cm), 9.5 cm, 9 cm, 8.5 cm, 8 cm, 7.5 cm, 7 cm, 6.5 cm, 6 cm, 5.5 cm, 5 cm, 4.5 cm, 4 cm, 3.5 cm, 3 cm, 2.5 cm, 2 cm, 1.5 cm, 1 cm, or less. The width of the gap space of the conduit may be less than about 50 millimeters (mm), 45 mm, 40 mm, 35 mm, 30 mm, 25 mm, 20 mm, 15 mm, 10 mm, 9 mm, 8 mm, 7 mm, 6 mm, 5 mm, 4 mm, 3 mm, 2 mm, 1 mm, 0.5 mm, or less. The width of the gap space of the conduit may be less that about 5 mm. The width of the gap space of the conduit may be less that about 4 mm. The width of the gap space of the conduit may be less that about 3 mm. The width of the gap space of the conduit may be less that about 2 mm. The width of the gap space of the conduit may be less than about 1 cm. The width of the gap space of the conduit may be adjustable between 0 mm and about 2 mm.

The device may exert a liquid suction capacity at an inlet port of about 40 pounds per square inch (psi), 35 psi, 30 psi, 29 psi, 28 psi, 27 psi, 26 psi, 25 psi, 24 psi, 23 psi, 22 psi, 21 psi, 20 psi, 19 psi, 18 psi, 17 psi, 16 psi, 15 psi, 14 psi, 13 psi, 12 psi, 11 psi, 10 psi, or about 5 psi. The liquid suction capacity may be about 25 psi. The liquid suction capacity may be about 20 psi. The liquid suction capacity may be about 15 psi. The liquid suction capacity may be about 10 psi. The liquid suction capacity may be between about 25 psi and about 10 psi.

The liquid suction capacity of the device may be adjustable. The liquid suction capacity may be adjustable between about 25 psi and about 10 psi. The liquid suction capacity may be adjustable between about 40 psi and about 5 psi. The liquid suction capacity may be adjustable between about 30 psi and about 10 psi. The liquid suction capacity may be adjustable between about 25 psi and about 5 psi. The liquid suction capacity may be manually adjusted by a user, for example, by adjusting the gap space of the conduit, or the user may specify a liquid suction capacity that can be programmed into the device, for example, at a remote location.

Adjusting the gap space may be independent of gas suction capacity but may change the liquid suction capacity at the inlet port. The device may be able to maintain a constant gas suction capacity over a large range of adjustable liquid suction capacities. The device may be able to maintain a constant gas suction capacity over a range of adjustable liquid suctions capacities from about 10 pounds per square inch (psi) to about 25 psi. The device may be able to maintain a constant gas suction capacity over a range of adjustable liquid suctions capacities from about 5 psi to about 40 psi. The device may be able to maintain a constant gas suction capacity over a range of adjustable liquid suctions capacities from about 10 psi to about 30 psi. The device may be able to maintain a constant gas suction capacity over a range of adjustable liquid suctions capacities from about 5 psi to about 25 psi.

A volumetric flow rate at an inlet port may be about 4 cubic feet per minute (cfm), 4.5 cfm, 5 cfm, 5.5 cfm, 6 cfm, 6.5 cfm, 7 cfm, 7.5 cfm, 8 cfm, 8.5 cfm, 9 cfm, 9.5 cfm, 10 cfm, 10.5 cfm, 11 cfm, 11.5 cfm, 12 cfm, 12.5 cfm, 13 cfm, 13.5 cfm, 14 cfm, 14.5 cfm, 15 cfm, 15.5 cfm, 16 cfm, 17 cfm, 18 cfm, 19 cfm, or 20 cfm. A volumetric flow rate may be between about 4 cfm and about 6 cfm. A volumetric flow rate may be between about 12 cfm and about 15 cfm.

A liquid suction rate at an inlet port may be about 100 cubic centimeters per sec (cc/sec), 95 cc/sec, 90 cc/sec, 85 cc/sec, 80 cc/sec, 75 cc/sec, 70 cc/sec, 65 cc/sec, 60 cc/sec, 55 cc/sec, 50 cc/sec, 45 cc/sec, 40 cc/sec, 35 cc/sec, 30 cc/sec, 25 cc/sec, 20 cc/sec, 15 cc/sec, 10 cc/sec, or about 5 cc/sec. The liquid suction rate may be between about 60 cc/sec and about 5 cc/sec. The liquid suction rate may be at least about 30 cc/sec. The liquid suction rate may be at least 25 cc/sec.

The liquid suction rate may be adjustable. The liquid suction rate may be adjustable between about 60 cc/sec and about 5 cc/sec. The liquid suction rate may be adjustable between about 60 cc/sec and about 30 cc/sec. The liquid suction rate may be adjustable between about 100 cc/sec and about 30 cc/sec. The liquid suction rate may be manually adjusted by a user, for example, by adjusting the gap space of the conduit, or the user may specify a liquid suction rate that can be programmed into the device, for example, at a remote location.

An inner diameter of the inlet port may be adjustable. A user may adjust the inner diameter of the inlet port, for example, by rotating a third tuner arm on the device. The inner diameter of the inlet port may be adjusted automatically based on the volume of matter entering the inlet port. The inner diameter may be adjustable between about 5 millimeters (mm) and about 10 centimeters (cm). The inner diameter may be adjustable between about 5 mm and about 50 mm. The inner diameter may be adjustable between about 25 mm and about 100 mm. The inner diameter may be adjustable between about 0.5 cm and 5 cm. The inner diameter may be adjustable between about 0.5 cm and about 10 cm. The inner diameter may be manually adjusted by a user, for example, by adjusting a third tuner arm, or the user may specify an inlet port inner diameter that can be programmed into the device, for example, at a remote location.

The suction device described herein provides a suction while generating a minimal or no associated sound. Operation of the suction device described herein may generate one or more sounds. The one or more sounds may be equivalent to a background noise, such as about 43 decibels (dB). The one or more sounds may be less than 6 dB louder than a background noise. The one or more sounds may be less than 4 dB louder than a background noise. The one or more sounds may be less than about 40 dB, 35 dB, 30 dB, 29 dB, 28 dB, 27 dB, 26 dB, 25 dB, 24 dB, 23 dB, 22 dB, 21 dB, 20 dB, 19 dB, 18 dB, 17 dB, 16 dB, 15 dB, 14 dB, 13 dB, 12 dB, 11 dB, 10 dB, 5 dB or less. The one or more sounds may be less than about 40 dB. The one or more sounds may be less than about 30 dB. The one or more sounds may be less than about 20 dB. The one or more sounds may be between about 10 dB and about 30 dB. The one or more sounds may be between about 15 dB and about 35 dB.

One or more embodiments comprising a backflow alert or alarm may emit one or more sounds. The one or more sounds emitted from the backflow alert may be audible. The one or more sounds emitted from the backflow alert may be about 100 dB, 95 dB, 90 dB, 85 dB, 80 dB, 75 dB, 70 dB, 65 dB, 60 dB, 55 dB, 50 dB, or 45 dB. The one or more sounds emitted from the backflow alert may be about 80 dB. The one or more sounds emitted from the backflow alert may be about 70 dB. The one or more sounds emitted from the backflow alert may be about 60 dB. The one or more sounds emitted from the backflow alert may be about 50 dB. The one or more sounds emitted from the backflow alert may be between about 45 dB and about 60 dB. The one or more sounds emitted from the backflow alert may be between about 45 dB and about 75 dB.

One or more filters may be included in the device. For example, two, three, four, five or more filters may be included in the device. The one or more filters may be positioned before the gap space of the conduit, after the gap space of the conduit, or a combination thereof. The one or more filters may be positioned at the inlet port (such as at a nozzle), at the outlet port (such as a pressurized waste port), within the housing, or any combination thereof. The one or more filters may collect matter, such as solid matter. The one or more filters may collect bacterial particles, viral particles, solid surgical waste, or any combination thereof. The one or more filters may collect solid matter based on a pore size of the one or more filters. The pore size of a filter may be less than 100 micrometers (um), 70 um, 20 um, 10 um, 5 um, 2 um, 1 um, 0.7 um, 0.5 um, 0.4 um, 0.3 um, 0.2 um, 0.1 um, 0.02 um, 0.01 um or less. The pore size may be about 100 um or less. The pore size may be about 70 um or less. The pore size may be about 0.5 um or less. The pore size may be about 0.2 um or less. The one or more filters may be positioned in series.

The device may be used for collection, such as collection of a fluid sample, a cell sample, or a tissue sample. For example, the device may be used for collection of a tissue sample, such as collection of polyps during a colonoscopy. The device may be used for collection of a tumor biopsy sample. The device may be used for collection of a fluid sample, such as collection of a blood sample during a surgery.

One or more filters may be included in the device to collect the sample. One or more filter may be included in the device to sort a suction flow so that one or more samples may be collected from the suction flow. One or more filters may collect a tissue sample and permit filtration or removal of excess gas or liquid that may also be suctioned during collection. One or more filters may collect a cell sample and permit filtration or removal of excess gas or liquid that may also be suctioned during collection. One or more filters may collect a tissue sample and a cell sample into separate areas of the device and permit filtration or removal of excess gas or liquid that may also be suctioned during collection. One or more filters may separate the collection materials (i.e. tissues, cells, particles), using different pore size filters. One or more filters may separate the collection materials, such as a cell sample, using positive selection or negative selection based on one or more cell surface markers. In some embodiments, the device may include fluidic pathways of a particular geometry to sort the suction flow and collect samples of particular interest.

One or more gases or liquids or tissues, such as excess gas or liquid or tissue, may exit the device. Excess gas or liquid or tissue may be collected into collection units for further use, such as collecting excess blood for further analysis of a condition of the subject or for further research use. Excess gas or liquid or solid may be recycled for further use, such as collecting excess blood that may be recycled for use in a subject. The device may also comprise collection units for storing the collection materials, such as storing a tissue sample after collection. Collection units of the device may be separate from the device, such as a separate unit that can be attached to the device during use, or may be formed in the device. Collection units may be reusable.

In some embodiments, the device may be, for example, used to provide suction during a surgical procedure. In some embodiments, the device may be configured to suction, for example, smoke, blood, or surgical debris including, for example, stool, pus, irrigation, or bone fragments. In some embodiments, the suction device provides sufficient suction to entirely or In some embodiments, one or more filters either located within the device or positioned in series to the device may separate for example gasses, liquids, and solids suctioned from a surgical field. For example, a first filter may be positioned immediately before the inlet port of the device to filter solids and a second filter may be positioned within the device to filter liquids and smaller particles from a suctioned gas.

Surgical byproducts can include one or more of liquids (e.g., blood, saliva), smoke, tissue, and/or noxious chemicals. The suction flow may be passed through a filter before exiting the suction assembly. The suction flow may be passed through a second air amplifier (e.g., after the filter).

The suction flow may pass through a backflow preventer (e.g., one-way valve) to prevent the pressurized gas flow from exiting the suction assembly via the suction port (e.g., in the event of a blockage). A user may be alerted to an obstruction in the suction assembly. The pressurized gas may be diverted to activate an alert. The pressurized gas flow may be directed out of a diversion port of the suction assembly when the backflow preventer is activated thereby preventing the pressurized gas flow from exiting the suction assembly via the suction port.

In some embodiments, a suction assembly includes a low pressure port to receive surgical byproducts in a flow entering a low pressure port. The suction assembly also includes a positive pressure exit port to send the surgical byproducts out of the suction assembly for collection. A positive pressure gas port receives a pressurized gas flow. A first air amplifier creates a flow from the low pressure port to the positive pressure port. This flow propels surgical byproducts entrained in the suction flow from the suction port to the exit port.

In some embodiments, the suction assembly can include one or more valves. The one or more valves can be a one-way valve. The one or more valves can be a shuttle valve, a pressure relief valve, a backflow prevention valve, a check valve, or any combination thereof.

In some embodiments, a spring can be a source of energy used to seal one or more valves, such as shuttle valves. The spring may provide a force of between about 0 pounds (lbs) and about 30 lbs. The spring may provide a force of between about 2 lbs and about 4 lbs. The spring may provide a force of at least about 2.5 lbs. The spring may provide a force of at least about 2 lbs. The spring may provide a force of at least about 1.5 lbs. The spring may provide a force of at least about 1 lbs. The spring may provide a force of at least about 0.5 lbs. The spring may provide a force of between about 0.5 lbs and 1 lbs. The spring may provide a force of between about 0.5 lbs and about 0.8 lbs.

In some embodiments, the suction assembly can also include a backflow prevention valve. The backflow prevention valve blocks the pressurized gas flow from exiting via the low pressure port. In particular, the backflow prevention valve stop pressurized gas from flowing out of the low pressure port when an obstruction blocks the flow between the backflow valve and the exit port. The backflow prevention valve may also divert the pressurized gas flow out a diversion port of the suction assembly.

In some embodiments, an air amplifier device comprises a structure defining a generally cylindrical cavity having a first opening at a first end and a second opening at a second end. The cylindrical cavity is defined by an inner wall of the cavity. The structure has a gap space, such as an annular opening, in the inner wall near the first end that defines a jet opening. This jet opening is adapted to allow a pressurized gas to flow out of the annular opening such that a low pressure region is produced at the first end and an amplified flow is produced at the second end. Annular opening is configured such that the pressurized gas enters the cavity at an angle (e.g., 0°-90°) with respect to the inner wall of the cavity that is towards the second end. In some embodiments, a more acute angle (e.g., 30°-50°) may be desirable. The cavity is configured such that it is flared to a larger diameter where the annular opening communicates with the cavity.

In some embodiments, a dimension of the gap space, such as an annular opening, is adjustable to control a pressure difference between ambient air and the low pressure region at the first end. A portion of the structure may be rotatable to adjust the dimension of the annular opening to control the pressure difference. The annular opening may have a profile such that the pressurized gas entering the cavity attaches to a curved surface of the portion of the structure defining the annular opening, thereby creating the low pressure region which increases the overall mass flow rate of the amplified flow.

The dimension of the annular opening can be adjustable to control a ratio of gas suction to liquid suction provided by the air amplifier. In some embodiments, the suction device includes a rotatable member to adjust a dimension of the annular opening to control the pressure difference between ambient air and the low pressure region at the first end. In some embodiments, the annular opening has a profile such that the pressurized gas entering the cavity attaches to a curved surface of the portion of the structure defining the annular opening, thereby creating the low pressure region which increases the overall mass flow rate of the amplified flow. The annular opening may have a profile such that the pressurized gas entering the cavity attaches to a portion of the structure defining the annular opening, thereby creating the low pressure region and increasing the overall mass flow rate of the amplified flow.

In some embodiments, a device for creating suction comprises a housing defining a cavity having a first opening at a first end and a second opening at a second end. The device also has at least one opening in an inner surface of the housing that is adapted to allow a gas flow out of the at least one opening such that a low pressure region is produced at the first end, and a combined flow is produced at the second end. This combined flow comprises the gas flow and a suction flow that enters the first end as a result of the low pressure region. The device also has a control that manipulates the at least one opening to adjust an amount of pressure difference between the low pressure region and an ambient pressure.

In some embodiments, the at least one opening is configured to use the Coanda effect. In some embodiments, the at least one opening is configured to use the Venturi effect. The device may also have a blockage detector that stops the gas flow out of the at least one opening when the combined flow is obstructed.

In some embodiments, a medical suction device comprises a positive pressure input port to receive a flow of pressurized gas. The device also includes an input port to provide a low pressure region that entrains and receives matter into the suction device. The device also includes a positive pressure output port to output the flow of pressurized gas and a flow of matter received into the suction device via the input port. The device also has a check valve in communication with the input port to prevent at least the flow of pressurized gas from exiting via the suction port.

In some embodiments, the medical suction device also includes an alert to mechanically activate when the check valve is preventing flow from exiting via the suction port. The activation of the check valve can, in some embodiments, divert at least a portion of the flow of pressurized gas to activate the alert. This diverted portion of pressurized gas may create an audible alert. For example, the diverted portion may be passed through a whistle thereby creating an audible sound. The alert can be a visible indicator. The diverted portion of pressurized gas may move a member that makes an indicator visible to an operator of the medical suction device. The alert may include a mechanical gauge or electronic transducer to measure pressure within the medical suction device. The alert may be configured to activate in response to an internal pressure of the device reaching a threshold criteria. The alert may also notify a user of current internal pressure levels of the device and/or whether one or more internal pressure levels are within (or outside of) the desired operating range.

In some embodiments, a medical suction device comprises an internal lumen from an intake port to an exhaust port. An air amplifier assembly in fluid flow communication with the internal lumen. The air amplifier assembly is to receive a source of compressed air whereby the compressed air is directed by the air amplifier assembly to create a low pressure region at the input port and a flow out of the exhaust port. The medical suction device also includes a backflow prevention valve in the internal lumen between the input port and the air amplifier assembly.

In some embodiments, the medical suction device also includes an alert that mechanically activates when the backflow prevention valve is preventing a flow from exiting via the suction port. The activation of the backflow prevention valve to prevent flow from exiting via the input port can also divert at least a portion of a flow of the compressed air to activate the alert. The alert can be an audible sound created by the portion of the flow of compressed air. For example, the portion of the flow of compressed air can be passed through a whistle thereby creating the audible sound. The alert could be a visible indicator. The diverted portion of the flow of compressed air can move a member that makes the visible indicator visible to an operator of the medical suction device.

In some embodiments, the medical suction device can include a blockage clearing control that, in combination with backflow prevention valve, pressurizes at least a portion of the lumen in order to clear a blockage. For example, when the blockage clearing control is activated, the blockage can be forced out of the exhaust port by the compressed air.

In some embodiments, a method of operating a medical suction device includes receiving a pressurized gas flow. The method also includes using the pressurized gas flow to create a low pressure region at an input port to entrain and receive matter into the suction device. The method also includes exhausting, via an output port, the pressurized gas flow and a flow of matter received via the input port. The method also includes activating a valve to prevent at least the pressurized gas flow from exiting via the input port in response to a blockage that reduces the pressurized gas flow and the flow of matter exhausted via the output port below a first threshold criteria.

In some embodiments, the method further includes activating an alert in response to a blockage that reduces the pressurized gas flow and the matter flow exhausted via the output port below a second threshold criteria. In some embodiments, the first threshold criteria and the second threshold criteria are met by the same reduction in flow of the pressurized gas flow and the matter flow exhausted via the output port. The alert may be coupled to the valve to activate the alert when the valve is activated.

FIG. 1 is a block diagram illustrating suction system 100. In FIG. 1, suction system 100 comprises vacuum generator 110. Vacuum generator 110 includes vacuum generator 110, input port 111, suction port 112, and exhaust port 113. Vacuum generator 110 is configured to receive positive pressure gas supply 121 from input port 111. Vacuum generator 110 is configured to generate low pressure region 122 from positive pressure gas supply 121 near suction port 112. Low pressure region 122 has a pressure below an ambient air pressure. The ambient air pressure overcomes the pressure in low pressure region 122 thereby creating suction within suction device 100. Low pressure region 122 pulls matter (e.g., liquids, gasses, and solids) into vacuum generator 110 via suction port 112. The matter pulled into vacuum generator 110 is propelled by vacuum generator 110 out of exhaust port 113. Exhaust port 113 outputs an effluent of the collected matter and the gasses received via input port 111. This effluent may be output to a tube, pipe, etc. for collection, separation, and/or disposal.

It should be understood that the terms 'positive pressure' and 'low pressure' are relative terms. These terms should be understood to be relative to the ambient air/gas pressure in the vicinity of vacuum generator 110. For example, positive pressure gas supply 121 may be a flow of compressed air, nitrogen, carbon dioxide or some other gaseous pressure source. In this case, positive pressure gas supply 121 is pressured above the ambient air surrounding vacuum generator 110. Likewise, low pressure region 122 may be a region where the air pressure in the vicinity of suction port 112 is less than the ambient air. This low pressure region causes air in the vicinity of suction port 112 to flow into suction port 112—possibly entraining matter.

In some embodiments, vacuum generator 110 utilizes a fluid flow amplifier (a.k.a., flow multiplier) to generate low pressure region 122 from positive pressure gas supply 121. In another embodiment, vacuum generator 110 utilizes a mechanical pump or fan powered by positive pressure gas supply 121 to create low pressure region 122.

In some embodiments, vacuum generator 110 may be configured for handheld operation. In this configuration, vacuum generator 110 would be sized and shaped to be held by one or more hands while being operated. Thus, rather than being a permanently mounted (or portable, but large) suction pump, vacuum generator 110 can be a relatively small device that operates to suction matter into suction port 112, and propel matter out of exhaust port 113. It should be understood that while vacuum generator 110 may be configured for handheld operation, it may also be used with alternative procedures (e.g., laparoscopy, robotic, etc.).

It should be understood that by receiving positive pressure gas supply 121, and producing positive pressure effluent 123, tubes and/or pipes connected to input port 111 and exhaust port 113 can be thin walled and collapsible. The tubes and/or pipes connected to input port 111 and exhaust port 113 can be collapsible since the positive pressure of positive pressure gas supply 121 and positive pressure effluent 123 will 'push open' or 'inflate' the collapsible tubing. Thus, lighter weight and/or less expensive tubing can be used with vacuum generator 110 than is used with 'negative pressure' systems that rely on a supplied vacuum line or vacuum source (such as a vacuum pump and/or plumbed wall ports).

Input port 111 is disposed within a wall of suction device 100. Input port 111 is configured to receive positive pressure gas supply 121. Input port is coupled to vacuum generator 110. Input port 1110 is configured to direct positive pressure gas supply 121 to vacuum generator 110. Vacuum generator 110 is configured to receive positive pressure gas supply 121. In some embodiments, input port 111 is configured to direct positive pressure gas supply 121 at an angle in relation to an interior wall of vacuum generator 110.

Suction port 112 is disposed at the distal end of suction device 100. Suction port 112 is configured to receive a flow of matter via low pressure region 122. Suction port 112 is configured to couple to the distal end of vacuum generator 110. Suction port 112 is configured to direct a flow of matter into vacuum generator 110. Vacuum generator 110 is configured to receive a flow of matter from suction port 112.

Exhaust port 113 is disposed towards the proximal end of suction device 100. Exhaust port 113 is coupled to vacuum generator 110. Exhaust port 113 is configured to receive a combined flow of positive pressure gas supply 121 and a flow of matter received at suction port 112 from vacuum generator. Exhaust port 113 is configured to expel at least the combined flow out of suction device 100. In some embodiments, exhaust port 113 may include fittings to attaching tubing configured to receive positive pressure effluent 123.

Figure 2:
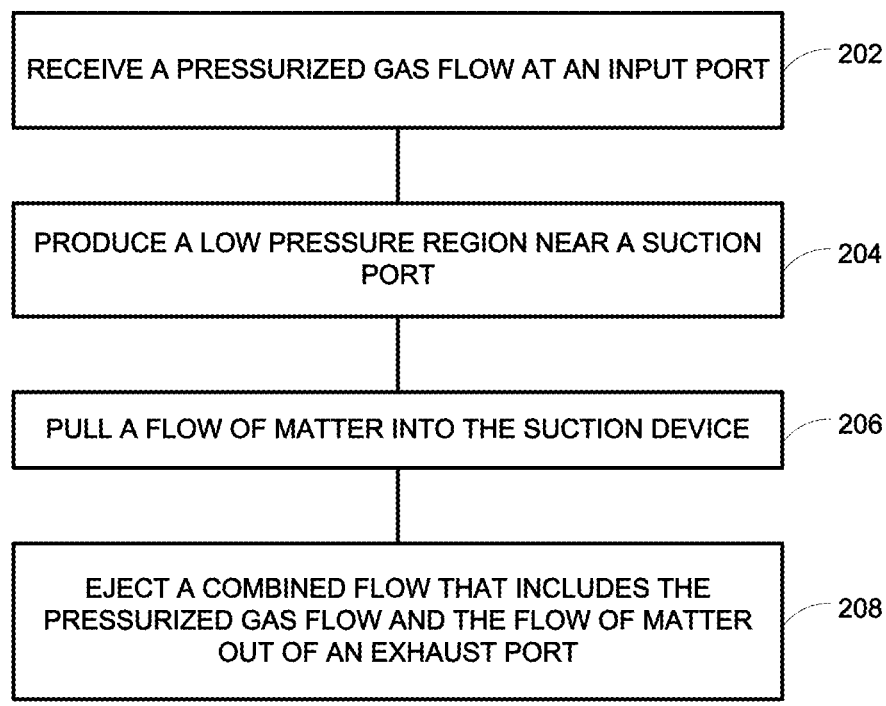
FIG. 2 is a block diagram illustrating a method of operating a suction system.

FIG. 2 is a block diagram illustrating a method of operating a suction system. The steps illustrated in FIG. 2 may be performed by one or more elements of suction system 100. A pressurized gas flow is received at an input port (202). For example, input port 111 is configured to receive positive pressure gas supply 121 and supply it to vacuum generator 110. Vacuum generator 110 is an example of an air flow amplifier. A low pressure region is produced near a suction port (204). For example, vacuum generator 110 is configured to produce a low pressure region near suction port 112 from positive pressure gas supply 121. A flow of matter is pulled into the suction device (206). For example, low pressure region 122 is less than an ambient air pressure. This causes a flow of matter to enter suction port 112. Suction port 112 is configured to receive this flow of matter. A combined flow that includes the pressurized gas flow and the flow of matter is ejected out of an exhaust port (208). For example, suction assembly 100 is configured to pass a combined flow (which can include positive pressure gas supply 121 and the flow of matter received at suction port 112) through vacuum generator 110 and out of exhaust port 113 as positive pressure effluent 123.

Figure 3:
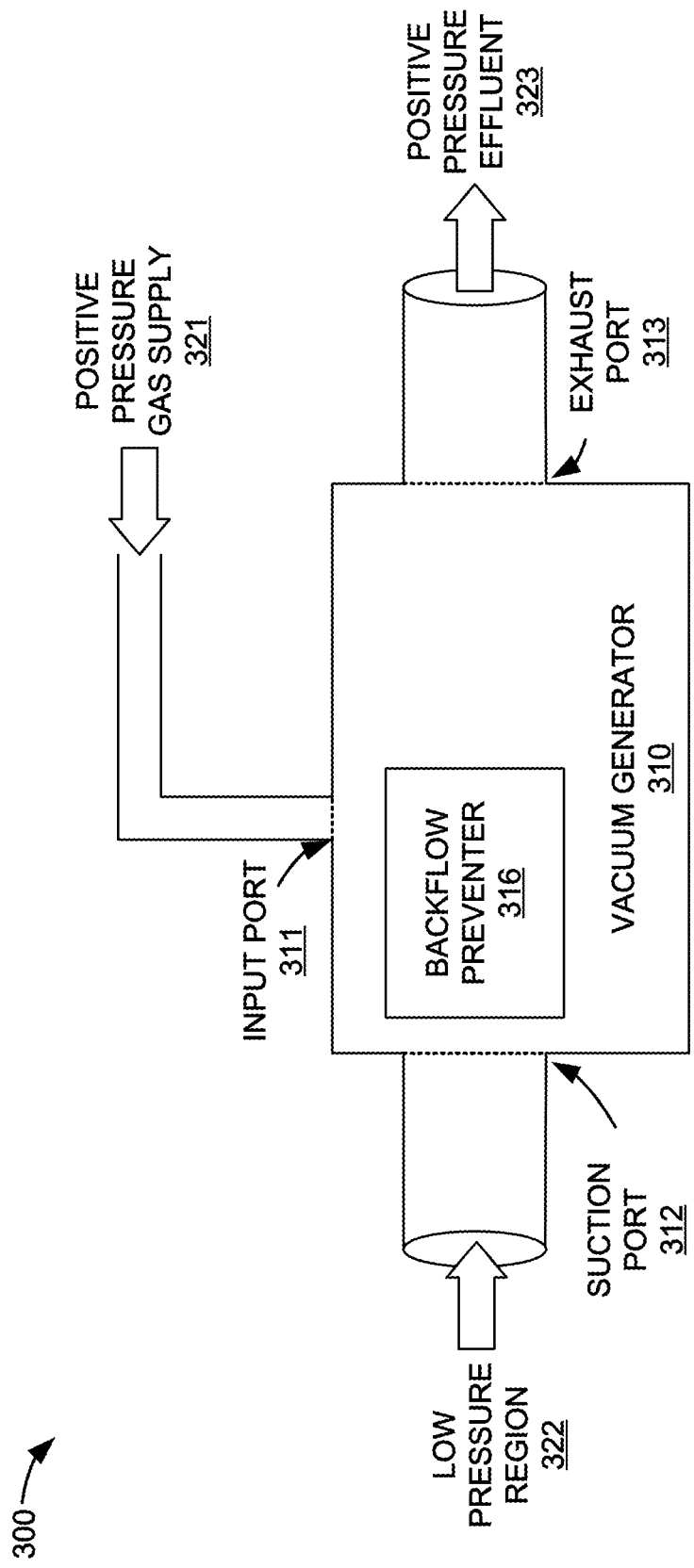
FIG. 3 is a block diagram illustrating a suction system with backflow prevention.

FIG. 3 is a block diagram illustrating suction system with backflow prevention 300. Suction system with backflow prevention 300 includes vacuum generator 310, includes input port 311, suction port 312, exhaust port 313 and backflow preventer 316. Suction system 300 is an example of suction system 100; however, suction system with backflow prevention 300 includes backflow preventer 316.

Vacuum generator 310 receives positive pressure gas supply 321 via input port 311 to generate low pressure region 322 at suction port 312. Low pressure region 322 entrains and receives matter into suction system with backflow prevention 300. Suction port 312 is configured to entrain and receive surgical byproducts (e.g., smoke, tissue, gasses, liquids, noxious chemicals, etc.) entering vacuum generator 310. In typical operation, the surgical byproducts pulled into vacuum generator 310 are propelled by vacuum generator 310 out of exhaust port 313 as positive pressure effluent 323. Exhaust port 313 outputs positive pressure effluent 323 comprising surgical byproducts entrained with positive pressure gas supply 321. Positive pressure effluent 323 may be output to a tube, pipe, etc. for collection, separation, and/or disposal.

Exhaust port 313 (or a tube connected to carry away positive pressure effluent 323), however, may become clogged or obstructed. When this happens, the obstruction can prevent all or a substantial portion of positive pressure effluent 323 from flowing out of exhaust port 313. Without backflow preventer 316, when positive pressure effluent 323 cannot flow out of exhaust port 313, positive pressure effluent 323 may instead be ejected out of suction port 312. The ejection of positive pressure effluent 323 (and of positive pressure gas supply 321, in particular) out of suction port 312 is undesirable and can cause damage or other problems to items in the vicinity of suction port 312 (e.g., a patient). However, backflow preventer 316 is configured to at least stop the flow of positive pressure effluent 323 from exiting via suction port 312.

Backflow preventer 316 can stop the operation of vacuum generator 310 by cutting off the supply of positive pressure gas supply 321 to one or more components of vacuum generator 310 that cause low pressure region 322 to be created. Backflow preventer 316 can stop the operation of vacuum generator 310 by preventing any 'reverse' flow of matter from exiting via suction port 312. For example, backflow preventer 316 may be placed in line with suction port 312. Backflow preventer 316 can activate when matter starts to flow in a manner that the flow would exit suction port 312. Backflow preventer 316 may be configured such that, once activated, it will stay activated thereby preventing any flow out of suction port 312 until positive pressure gas supply 321 is removed (i.e., turned off), or the blockage is cleared. Backflow preventer 316 may also divert positive pressure gas supply 321 to flow out of a diversion port when activated such that positive pressure gas supply 321 and positive pressure effluent 323 can flow out of vacuum generator 310.

Figure 4:
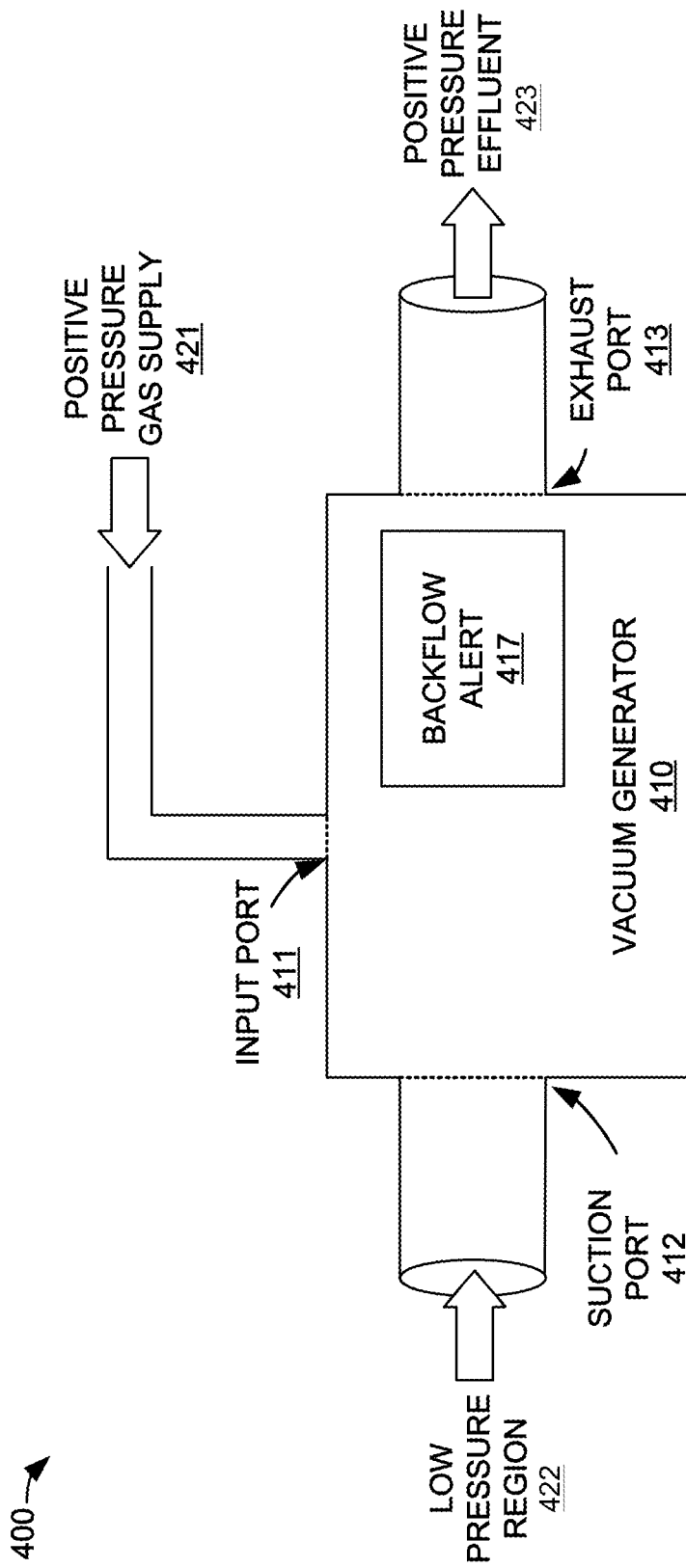
FIG. 4 is a block diagram illustrating a suction system with backflow alert.

FIG. 4 is a block diagram illustrating suction system with backflow alert 400. Suction system with backflow alert 400 is an example of suction system 100 and suction system 300; however, suction system with backflow alert 300 includes backflow alert 417. Suction system with backflow alert 400 comprises vacuum generator 410, positive pressure input port 411, suction port 412, exhaust port 413, a low pressure region 422, a positive pressure effluent 423, and backflow alert 417.

Backflow alert 417 is configured to alert a user of suction system 400 to the existence of a blockage. Once alerted to a blockage, the user can do one or more of: (1) discontinue use of vacuum generator 410; (2) clear the blockage thereby restoring normal operation; and (3) terminate the supply of positive pressure gas supply 421 thereby shutting off vacuum generator 410.

Backflow alert 417 can generate an audible alert (e.g., a whistle or other alarm type noise), a visible alert (e.g., a flag or other visible indicator), a tactile alert (e.g., vibration) or some other type of alert to notify the user to the existence of a blockage. Backflow alert 417 may use mechanical or electrical means to generate an alert. To provide examples of some mechanical means that may be used to generate an alert, backflow alert 417 may use air pressure to generate an audible alert using a whistle type apparatus, a visible alert by physically moving a flag or other visible indicator, or a tactile alert by physically moving a piece of mass. Similarly, various electronic components including transducers, mass airflow sensors and the like may be used by backflow alert 417 to detect backflow and signal circuitry to activate backflow alert 417.

In some embodiments, backflow alert 417 may include one or more a mechanical gauges or electronic transducers to measure pressure within vacuum generator 410. Backflow alert 417 may be configured to active in response to internal pressure within vacuum device 410 reaching a threshold criteria. Backflow alert 417 may also notify a user of the current internal pressure levels of vacuum generator 410 and/or whether the internal pressure levels are within the desired operating range. The various types of alerts described herein may be used individually or in combination. Likewise, backflow alert 417 may use both mechanical and electrical means to detect backflow individually or in combination.

In some examples, vacuum generator 410 may have a check valve, for example backflow preventer 310, in communication with input port 411 to prevent at least the flow of positive pressure gas supply 421 from exiting suction port 412. Backflow alert 417 may be configured to activate when the check valve is preventing positive pressure gas supply 421 from exiting suction port 412. Activation of the check valve to prevent positive pressure gas supply 421 from exiting suction port 412 may divert at least a portion of positive pressure gas supply 421 to activate backflow alert 417. Backflow alert 417 may generate an audible sound using a portion of positive pressure gas supply 421. For example, backflow alert 417 may direct a portion of positive pressure gas supply through a whistle thereby creating an audible sound. Alternatively, backflow alert 417 may use a visible indicator to notify the use to the existence of a blockage. Backflow alert 417 may divert a portion of positive pressure gas supply 421 to move a member that makes a visible indicator visible to an operator of suction system with backflow alert 400.

Figure 5:
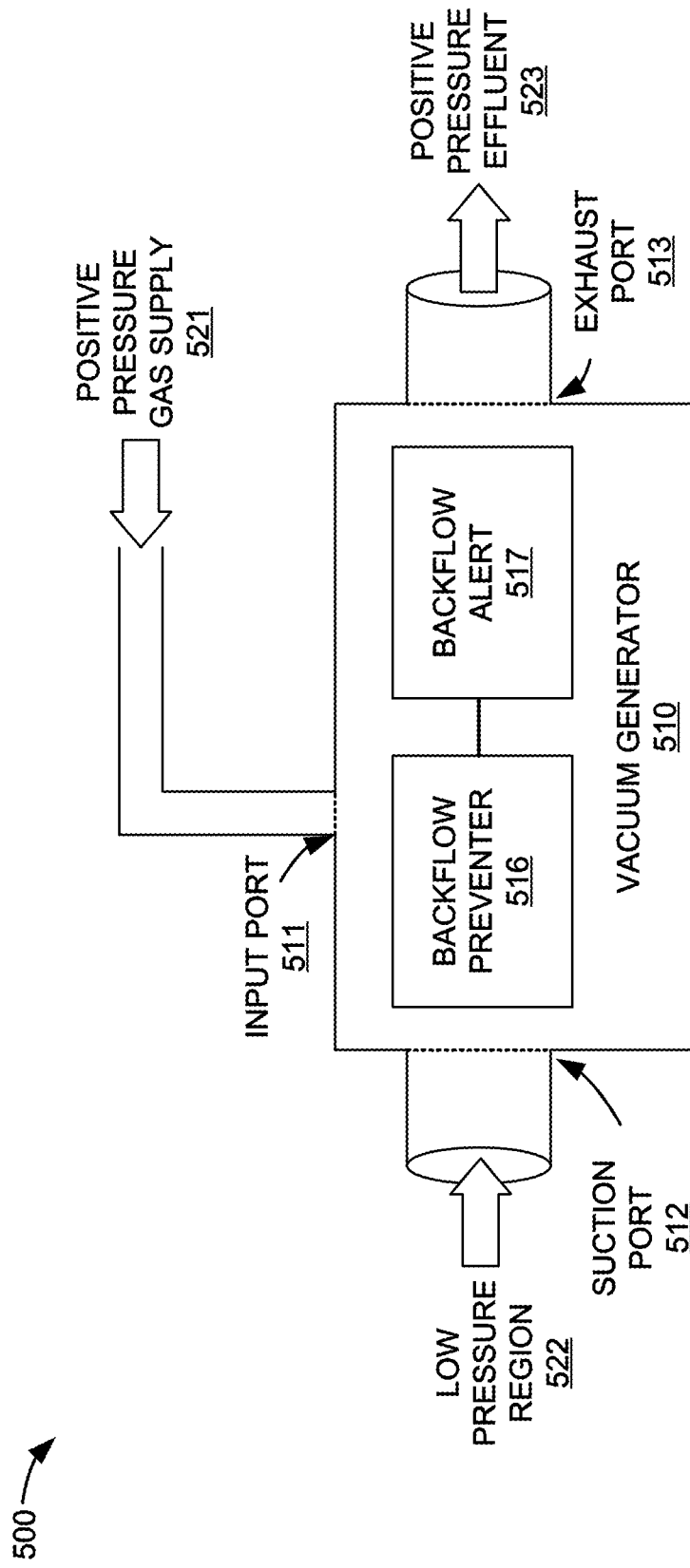
FIG. 5 is a block diagram illustrating a suction system with safety features.

FIG. 5 is a block diagram illustrating suction system with safety features 500. Suction system with safety features 500 can be an example of suction system 100, suction system with backflow prevention 300, and suction system with backflow alert 400; however, suction system with safety features 500 may have alternative configurations and methods of operation. Suction system with safety features 500 comprises vacuum generator 510, positive pressure input port 511, suction port 512, exhaust port 513, backflow preventer 516 and backflow alert 517. Backflow preventer 516 is operatively coupled to backflow alert 517.

Backflow preventer 516 can stop the operation of vacuum generator 510 by cutting off the supply of positive pressure gas supply 521 to one or more components of vacuum generator 510 that cause low pressure region 522 to be created. Backflow preventer 516 can stop the operation of vacuum generator 510 by preventing any 'reverse' flow of matter from exiting via suction port 512. Backflow preventer 516 can activate when matter starts to flow in a manner that the flow would exit suction port 512. Backflow preventer 516 may be configured such that, once activated, it will stay activated thereby preventing any flow out of suction port 512 until positive pressure gas supply 521 is removed (i.e., turned off), or the blockage is cleared.

Backflow preventer 516 may be operatively coupled to backflow alert 517 in order to activate backflow alert 517 in response to the activation of backflow preventer 516. In this manner, in response to a blockage, vacuum generator 510 both stops (i.e., prevents) the reverse flow of effluent out of suction port 512 as well as alerts the user to the blockage.

Backflow alter 517 is operatively coupled to backflow preventer 516. Backflow alert 517 is configured to alert a user of vacuum generator 510 to the existence of a blockage. Once alerted to a blockage, the user can do one or more of: (1) discontinue use of vacuum generator 510; (2) clear the blockage thereby restoring normal operation; and (3) terminate the supply of positive pressure gas supply 521 thereby shutting off vacuum generator 510.

Backflow alert 517 can generate an audible alert (e.g., a whistle or other alarm type noise), a visible alert (e.g., a flag or other visible indicator), a tactile alert (e.g., vibration) or some other type of alert to notify the user to the existence of a blockage. Backflow alert 517 may use mechanical or electrical means to generate an alert. To provide examples of some mechanical means that may be used to generate an alert, backflow alert 517 may use air pressure to generate an audible alert using a whistle type apparatus, a visible alert by physically moving a flag or other visible indicator, or a tactile alert by physically moving a piece of mass. Similarly, various electronic components including transducers, mass airflow sensors and the like may be used by backflow alert 517 to detect backflow and signal circuitry to activate backflow alert 517. The various types of alerts described herein may be used individually or in combination. Likewise, backflow alert 517 may use both mechanical and electrical means to detect backflow individually or in combination.

In some embodiments, backflow alert 517 may include one or more a mechanical gauges or electronic transducers to measure pressure within vacuum generator 510. Backflow alert 517 may be configured to active in response to internal pressure within vacuum device 510 reaching a threshold criteria, such as an increase in the internal pressure, indicating a possible obstruction. Backflow alert 517 may also notify a user of the current internal pressure levels of vacuum generator 510 and/or whether the internal pressure levels are within the desired operating range. The various types of alerts described herein may be used individually or in combination. Likewise, backflow alert 517 may use both mechanical and electrical means to detect backflow individually or in combination.

Vacuum generator 510 includes backflow preventer 516 in communication with input port 511 to prevent at least the flow of positive pressure gas supply 521 from exiting suction port 512. Backflow alert 517 may be configured to activate when backflow preventer 516 is preventing positive pressure gas supply 521 from exiting suction port 512. Activation of backflow preventer 516, to prevent positive pressure gas supply 521 and positive pressure effluent 523 from exiting suction port 512, may divert at least a portion of positive pressure gas supply 521 to activate backflow alert 517. Backflow alert 517 may generate an audible sound using a portion of positive pressure gas supply 521. For example, backflow alert 517 may direct a portion of positive pressure gas supply through a whistle thereby creating an audible sound. Alternatively, backflow alert 517 may use a visible indicator to notify the use to the existence of a blockage. Backflow alert 517 may divert a portion of positive pressure gas supply 521 to move a member that makes a visible indicator visible to an operator of suction system with backflow alert 500.

Figure 6:
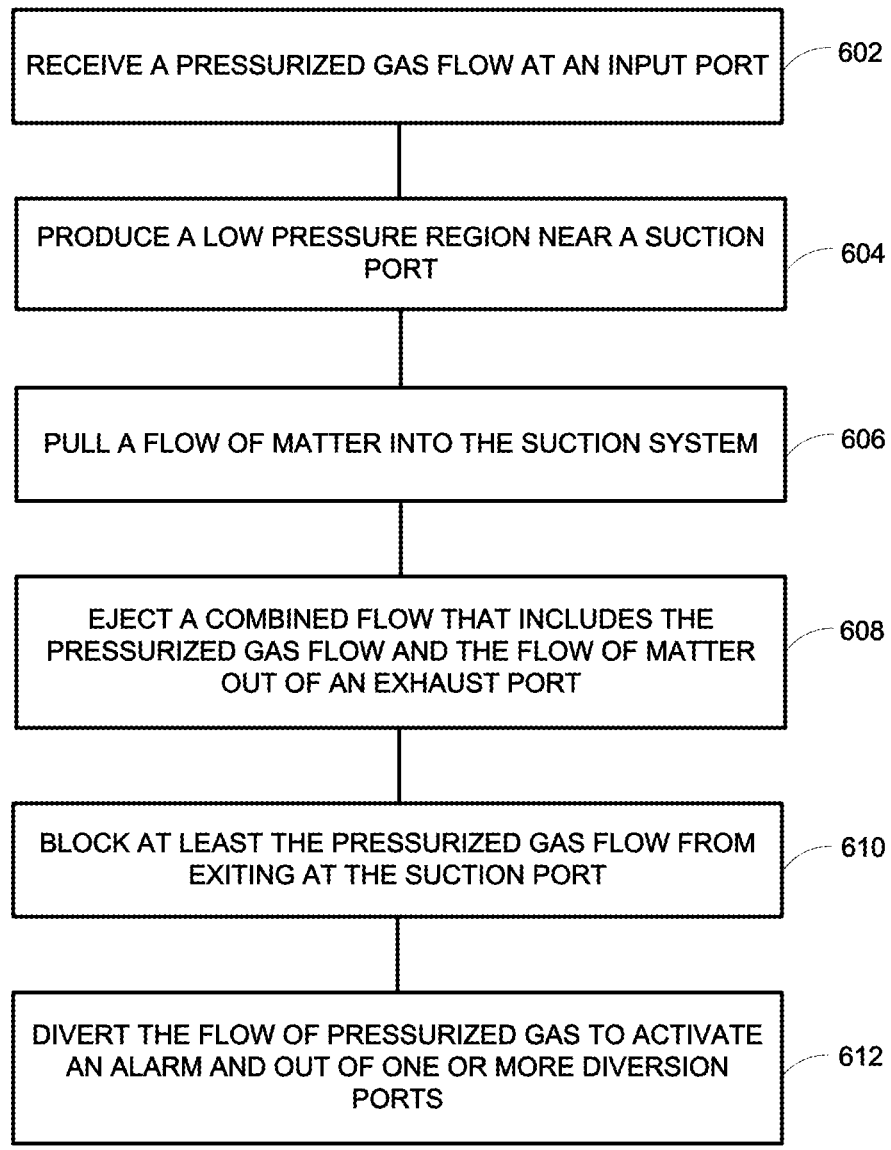
FIG. 6 is a block diagram illustrating a method of operating a suction system with safety features.

FIG. 6 is a block diagram illustrating a method of operating a suction system with safety features. The steps illustrated in FIG. 6 may be performed by one or more elements of suction system 500. A pressurized gas flow is received at an input port (602). For example, input port 511 is configured to receive positive pressure gas supply 521 and supply it to vacuum generator 510. Vacuum generator 510 is an example of an air flow amplifier. A low pressure region is produced near a suction port (604). For example, vacuum generator 510 is configured to produce low pressure region 522 near suction port 512 by directing positive pressure gas supply 521 through vacuum generator 510. A flow of matter is pulled into the suction system (606). For example, low pressure region 522 is less than an ambient air pressure. This causes a flow of matter to enter suction port 512. Suction port 512 is configured to receive this flow of matter. A combined flow that includes the pressurized gas flow and the flow of matter received at the suction port is ejected out of an exhaust port (608). For example, suction system with safety features 500 is configured to eject a combined flow (which can include positive pressure gas supply 521 and the flow of matter received at suction port 512) out of exhaust port 513 as positive pressure effluent 523. At least the pressurized gas flow is blocked from exiting at the suction port (610). For example, backflow preventer 516 is configured prevent at least positive pressure gas supply 521 from exiting suction port 512. Backflow preventer 516 may be activated when a portion of suction system with safety features 500 becomes obstructed by a blockage. The flow of pressurized gas is diverted to activate an alarm and out one or more diversion ports (612). For example, backflow preventer 516 is configured to divert positive pressure gas supply 521 to activate alert 517 and out one or more diversion ports.

Figure 7:
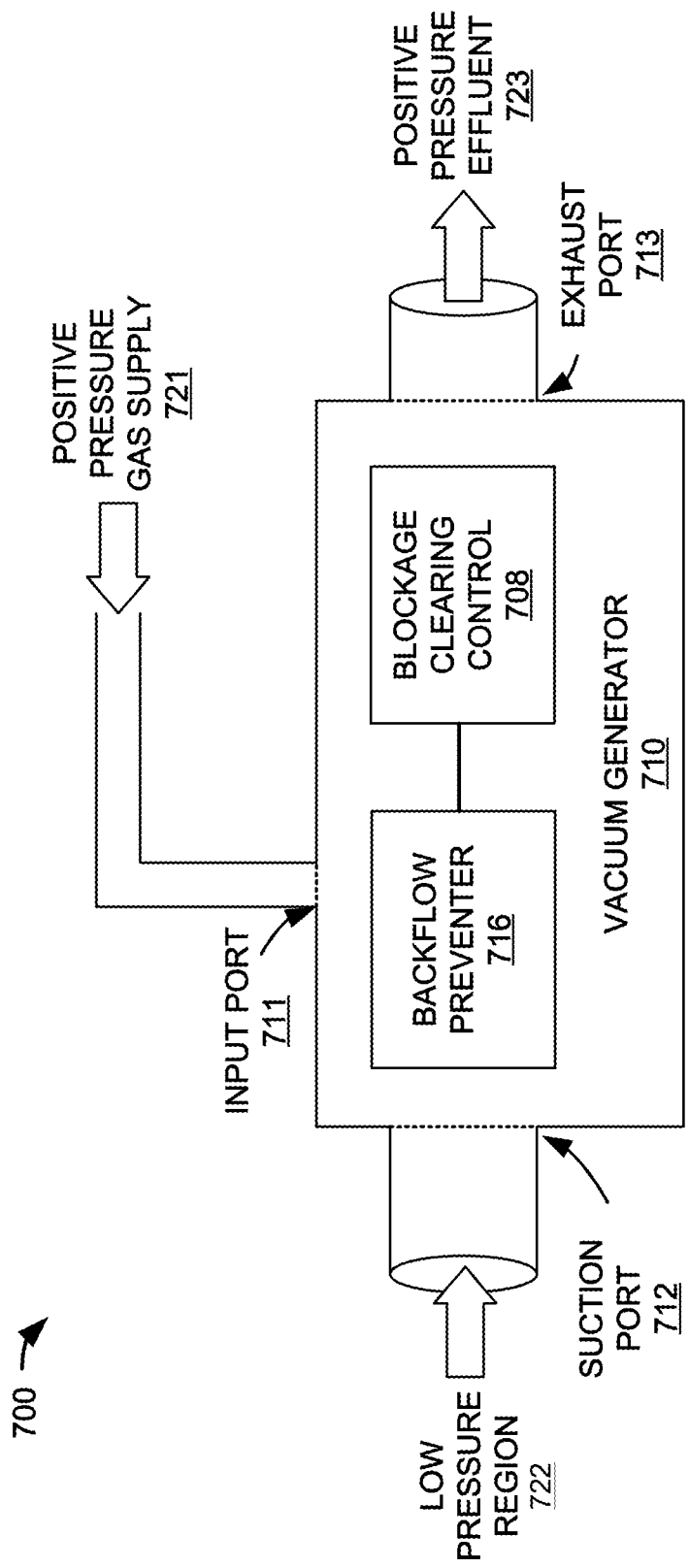
FIG. 7 is a block diagram illustrating a suction system with blockage clearing control.

FIG. 7 is a block diagram illustrating suction system with blockage clearing control 700. Suction system with blockage clearing control 700 is an example of suction system 100, suction system with backflow prevention 300, suction system with backflow alert 400, and suction system with safety features 500; however, suction system with blockage clearing control 700 includes blockage clearing control 708. Suction system with blockage clearing control 700 includes backflow clearing control 708, vacuum generator 710, input port 711, suction port 712, exhaust port 713, a low pressure region 722, and backflow preventer 716.

Blockage clearing control 708 is configured to increase pressure within vacuum generator 710 received from positive pressure gas supply 721 responsive to a user input. In operation, pressure within vacuum generator 710 received from positive pressure gas supply 721 is increased when blockage clearing control 708 is activated. This increase in pressure within vacuum generator 710 may force a blockage out of exhaust port 713. The blockage may be carried away as positive pressure effluent 723. In some embodiments, vacuum generator 710 may include one or more diversion ports configured to divert positive pressure gas supply 721 from exiting suction port 712 in the event that suction system with blockage clearing controls 700 becomes obstructed. In some embodiments, blockage clearing control 708 may be configured to block the one or more diversion ports allowing pressure to increase within vacuum generator 710. In some embodiments, blockage clearing control 708 may work in conjunction with backflow preventer 716 to increase pressure. In such embodiments, backflow preventer 716 may be configured to block positive pressure gas supply 721 from exiting suction port 712 and blockage clearing control 708 may simultaneously block one or more diversion ports to cause an increase in pressure within vacuum generator 710.

Figure 8:
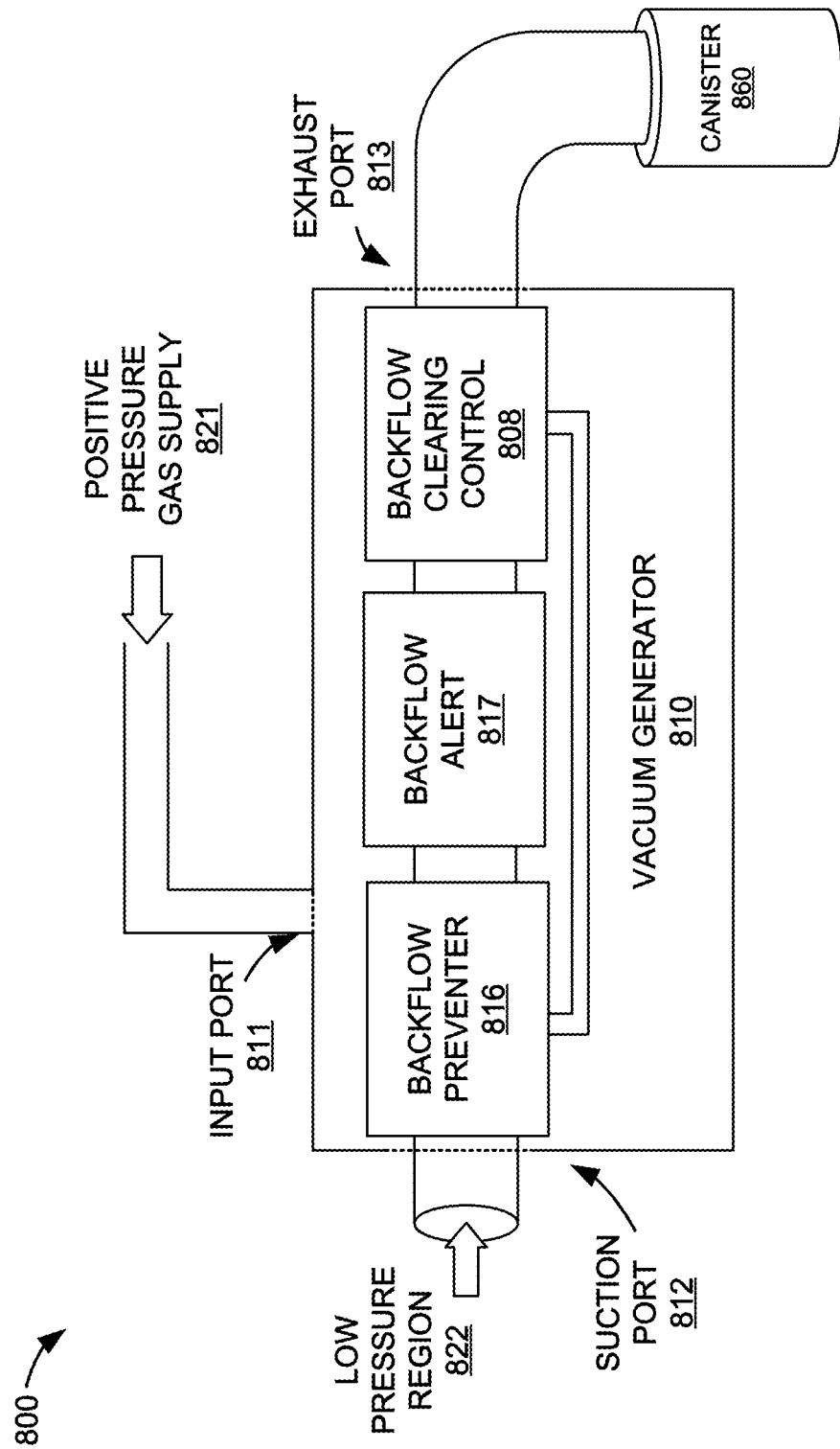
FIG. 8 is a block diagram illustrating a suction system with safety features and blockage clearing control.

FIG. 8 is a block diagram illustrating suction system with safety features and blockage clearing control 800. Suction system with safety features and blockage clearing control 800 is an example of suction system 100, suction system with backflow prevention 300, suction system with backflow alert 400, suction system with safety features 500 and suction system with backflow clearing control 700; however, suction system with safety features and blockage clearing control 800 may include alternative configurations and methods of operation. In FIG. 8, suction system with safety features and blockage clearing control 800 includes backflow clearing control 808, vacuum generator 810, input port 811, suction port 812, exhaust port 813, backflow preventer 816, backflow alert 817 and canister 860.

Backflow clearing control 808 is configured to eject an obstruction or a blockage from vacuum generator 810 out exhaust port 813. Backflow clearing control 808 is configured to increase pressure supplied from positive pressure gas supply 821 within vacuum generator 810. This increase in pressure may force an obstruction or blockage out exhaust port 813. In some embodiments, backflow clearing control 808 may work in conjunction with backflow preventer 816. In such an example, backflow preventer 816 may block positive pressure gas supply 821 from exiting at suction port 812 and divert positive pressure gas supply 821 out one or more diversion ports. Blockage clearing control may be configured to block the one or more diversion ports allowing pressure from positive pressure gas supply 821 to increase within vacuum generator 810.

Vacuum generator 810 is configured to receive positive pressure gas supply 821 from input port 811. Vacuum generator 810 is configured to generate low pressure region 822 near suction port 812 from positive pressure gas supply 821. In some embodiments, input port 811 is configured to supply positive pressure gas supply to vacuum generator 810 at an angle in relation to an interior wall of vacuum generator 810. Vacuum generator 810 may be configured to take advantage of the Coanda effect to generate low pressure region 822.

Input port 811 is configured to receive positive pressure gas supply 821 and supply it to vacuum generator 810. In some embodiments, input port 811 may be configured to supply positive pressure gas supply 821 to vacuum generator 810 at an angle in relation to an interior wall of vacuum generator 810. Tubing may be used to supply positive pressure gas supply 821 to input port 811. In some embodiments, input port 811 may include fittings for coupling tubing to input port 811. Some types of fittings that may be used include: barbed, quick-disconnect, or compression fittings.

Suction port 812 is disposed towards the distal end of vacuum generator 810. Suction port 812 is configured to receive a flow of matter and supply it to vacuum generator 810. In operation, low pressure region 822 pulls a flow of matter into suction port 812. Suction port 812 supplies the flow of matter to vacuum generator 810. In some embodiment, suction port 812 may include openings radially arrayed in the wall of suction port 812. The openings provide additional suction near suction port 812. The openings may be configured to take advantage of the Venturi effect. The openings may be configured to open and close in response to user input.

Exhaust port 813 is configured to direct a positive pressure effluent from vacuum generator 810 to a collection source. Canister 860 is an example of a collection source. In some embodiments, exhaust port 813 may include fittings for coupling to tubing. Some types of fittings that may be used include barbed, quick-disconnect, or compression fittings. Tubing may be used to couple exhaust port 813 to canister 860.

Backflow preventer 816 can stop the operation of vacuum generator 810 by cutting off the supply of positive pressure gas supply 821 to one or more components of vacuum generator 810 that cause low pressure region 822 to be created. Backflow preventer 816 can stop the operation of vacuum generator 810 by preventing any 'reverse' flow of matter from exiting via suction port 812. For example, backflow preventer 816 may be placed in line with suction port 812. Backflow preventer 816 can activate when matter starts to flow in a manner that the flow would exit suction port 812. Backflow preventer 816 may be configured such that, once activated, it will stay activated thereby preventing any flow out of suction port 812 until positive pressure gas supply 821 is removed (i.e., turned off), or the blockage is cleared. Backflow preventer 816 may be operatively coupled to backflow alert 817 in order to activate backflow alert 817 in response to the activation of backflow preventer 816. In this manner, in response to a blockage, vacuum generator 810 both stops (i.e., prevents) the reverse flow of effluent out of suction port 812 as well as alerts the user to the blockage.

Backflow alert 817 is configured to alert a user of vacuum generator 810 to the existence of a blockage. Once alerted to a blockage, the user can do one or more of: (1) discontinue use of vacuum generator 810; (2) clear the blockage thereby restoring normal operation; and (3) terminate the supply of positive pressure gas supply 821 thereby shutting off vacuum generator 810. In operation, backflow alert 817 may be configured to activate when backflow preventer 816 is preventing positive pressure gas supply 821 from exiting suction port 812. Backflow alert 817 may be configured to active in response to internal pressure within vacuum device 810 reaching a threshold criteria. One example of a threshold criteria includes a pre-determined pressure level within vacuum generator 810 that may be indicative of an obstruction. Backflow alert 817 can generate an audible alert (e.g., a whistle or other alarm type noise), a visible alert (e.g., a flag or other visible indicator), a tactile alert (e.g., vibration) or some other type of alert to notify the user to the existence of a blockage. Backflow alert 817 may use mechanical or electrical means to generate an alert. Backflow alert 817 may generate an audible sound using a portion of positive pressure gas supply 821. For example, backflow alert 817 may direct a portion of positive pressure gas supply through a whistle thereby creating an audible sound. Alternatively, backflow alert 817 may use a visible indicator to notify the use to the existence of a blockage. Backflow alert 817 may divert a portion of positive pressure gas supply 821 to move a member that makes a visible indicator visible to an operator. Similarly, various electronic components including transducers, mass airflow sensors and the like may be used by backflow alert 817 to detect backflow and signal circuitry to activate backflow alert 817. Backflow alert 817 may use one or a combination of alerts described herein to notify the user of vacuum generator 810 to the existence of a blockage.

Canister 860 is configured to receive waste output from exhaust port 813 for collection, separation, and/or disposal. In some embodiments, canister 860 may be coupled to an output to a tube, pipe, etc. for collection, separation, and/or disposal. In some embodiments, canister 860 may be a suction canister connected to a vacuum source. Canister 860 may contain a filter. Canister 860 may be manufactured from plastic, glass, metal or some other material having desirable properties. Some desirable properties may include: cost, ability to be sterilized, manufacturing method, application or some other metric.

Figure 9:
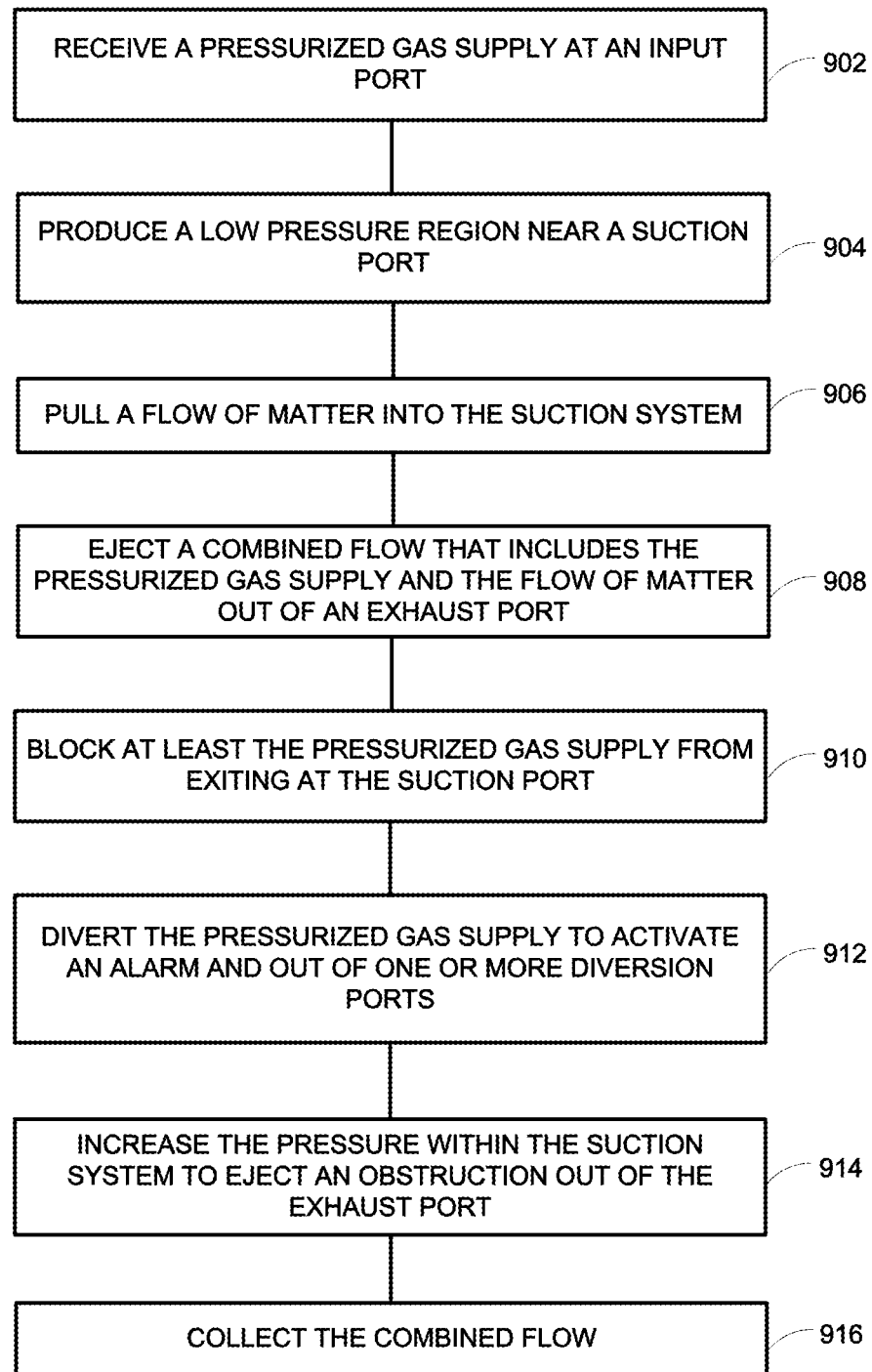
FIG. 9 is a block diagram illustration a method of operating a suction system with safety features and blockage clearing control.

FIG. 9 is a block diagram illustrating a method of operating a suction system with safety features and blockage clearing control. The steps illustrated in FIG. 9 may be performed by one or more elements of suction system with safety features and blockage clearing control 800. A pressurized gas supply is received at an input port (902). For example, input port 811 is configured to receive positive pressure gas supply 821 and supply it to vacuum generator 810. Vacuum generator 810 is an example of an air flow amplifier. A low pressure region is produced near a suction port (904). For example, vacuum generator 810 is configured to produce a low pressure region near suction port 812 by directing positive pressure gas supply 821 through vacuum generator 810. A flow of matter is pulled into the suction system (906). For example, low pressure region 822 is less than an ambient air pressure. This causes a flow of matter to enter suction port 812. Suction port 812 is configured to receive a flow of matter into suction system with safety features and blockage clearing control 800. A combined flow that includes the pressurized gas supply and the flow of matter is ejected out of an exhaust port (908). For example, suction assembly with safety features and blockage clearing control 800 is configured to exhaust a combined flow (which includes positive pressure gas supply 821 and the flow of matter received at suction port 812) out of exhaust port 813. At least the pressurized gas flow is blocked from exiting at the suction port (910). For example, backflow preventer 816 is configured to activate when a portion of suction system with safety features and blockage clearing control 800 becomes obstructed. Backflow preventer 816 is configured to prevent at least positive pressure gas supply 821 from exiting via suction port 812. The flow of pressurized gas is diverted to activate an alarm and out of one or more diversion ports (912). For example, backflow preventer 516 is configured to divert at least a portion of pressurized gas supply 521 to activate alert 517 and the remaining our of a diversion port. The pressure within the suction system is increased until an obstruction is ejected out of the exhaust port (914). For example, blockage clearing control 808 is configured to increase pressure from positive pressure gas supply 821 until a blockage is ejected out of exhaust port 813. The combined flow is collected (916). For example, canister 860 is coupled to exhaust port 813. Exhaust port 813 is configured to direct the combined flow into canister 860. Canister 860 is configured to collect at least the combined flow.

Figure 10A:
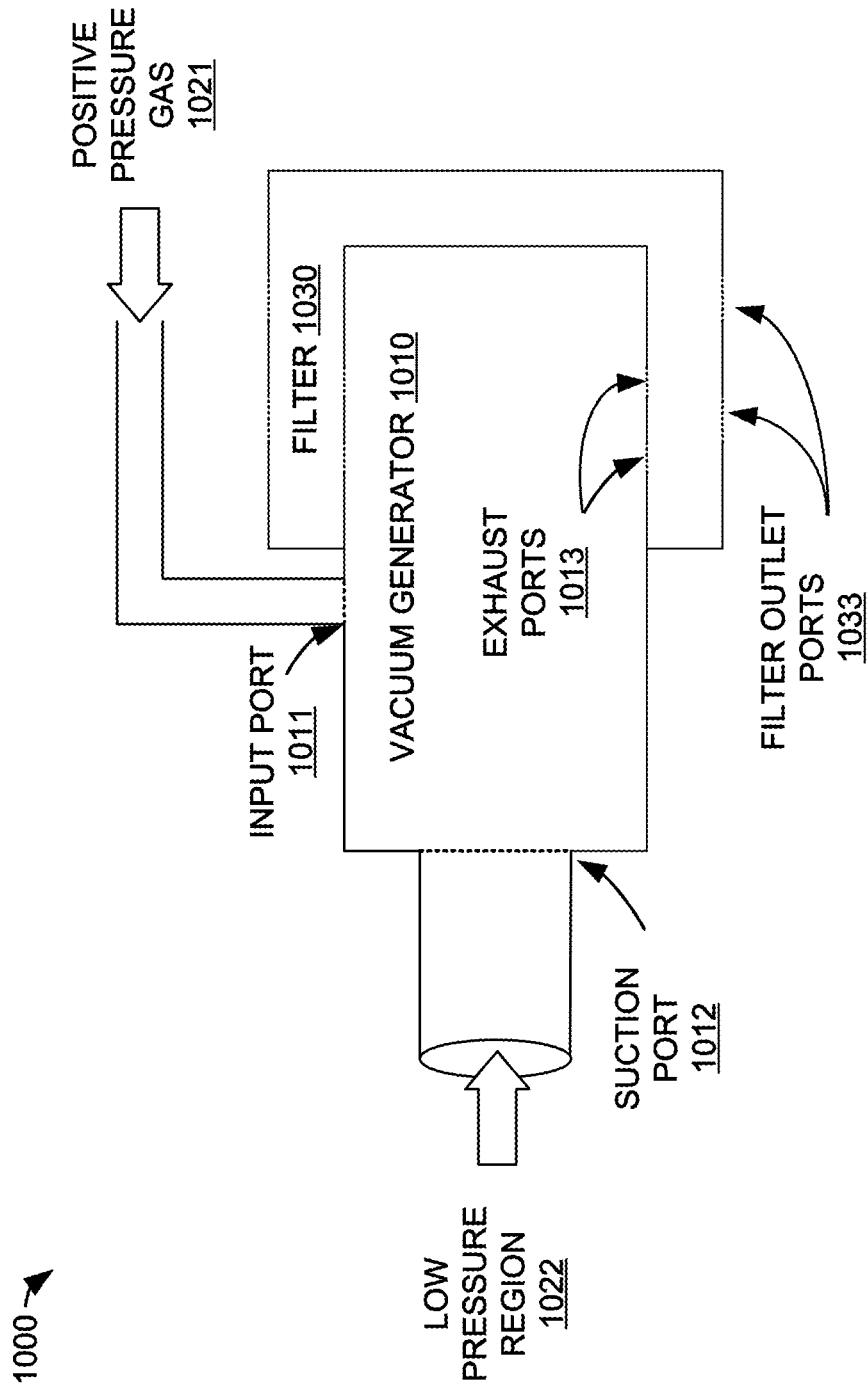
FIG. 10A is a block diagram illustrating a filtering suction system.

FIG. 10A is a block diagram illustrating filtering suction system 1000. Filtering suction system 1000 is an example of suction system 100, suction system with backflow prevention 300, suction system with backflow alert 400, suction system with safety features 500, suction system with backflow clearing control 700 and suction system with safety features and blockage clearing control 800; however, filtering suction system 1000 includes filter 1030. As illustrated in FIG. 10A, filtering suction system 1000 includes vacuum generator 1010, input port 1011, suction port 1012, exhaust ports 1013 and filter 1030.

Vacuum generator 1010 is configured to receive positive pressure gas 1021 to generate low pressure region 1022 at suction port 1012. Low pressure region 1022 entrains and receives matter into filtering suction system 1000. Matter can include surgical byproducts (e.g., smoke, tissue, gasses, liquids, noxious chemicals, etc). In typical operation, the surgical byproducts pulled into vacuum generator 1010 are propelled by vacuum generator 1010 out of exhaust ports 1013 through filter 1030.

Filter 1030 is configured to trap matter included in a combined flow (which can include positive pressure gas 1021 and surgical byproducts). Various embodiments of filter 1030 may trap different types of matter using different operations. Filter 1030 includes one or more filter inlet ports (exhaust ports 1013 are integral to filter inlet ports in this example) and one or more filter output ports 1033. The one or more filter inlet ports are configured to receive a combined flow from vacuum generator 1010. Filter 1030 traps matter contained in the combined flow and passes a filtrate to filter outlet ports 1030. Filter 1030 may be contained inside filtering suction system 1000 configured for hand-held operation. Alternatively, filter 1030 may also be located some distance from the hand-held portion of vacuum generator 1010. Surgical byproducts and positive pressure gas 1021 may be output to a tube, pipe, etc. for transport to filter 1030.

Filter 1030 may comprise mechanical, biological, chemical or other types of filters including any combination thereof. Mechanical filtration may include physical barrier or filter media type filters, vortex filters or cyclonic type filters or a combination thereof.

Filters using a physical barrier or filter media retain particles by physically blocking particulates from passing through the filter media. Filter media mechanically or physically strains solids from the effluent passing through it. Filter media is available in a variety of materials and porosities, which may be selected to limit the size of the particulate they can extract. The larger the pores in the filter media, the larger the particulate matter must be in order for the filter to extract it. Combinations of different materials and porosities of filter media may be used to separate specific elements comprising an effluent of the collected matter and the gasses received via suction port 1012 out exhaust ports 1013 into filter 1030.

Vortex or cyclonic filters operate by cyclonic separation methods to remove particulates from an effluent without the need for a physical barrier or filter media. Rotational effects and gravity are used to separate mixtures of solids and fluids. This method can also be used to separate fine droplets of liquid from a gaseous stream.

Biological filtration uses living microorganisms, such as bacteria and fungi, to capture and biologically degrade pollutants, harmful chemicals and other undesirable content from an effluent. Biological filtration can be used with gases and liquids. Biological filters comprise a filter media on which beneficial microorganisms grow. Biological filter media can be made from sand, plastic, metals, ceramics and other materials. Materials having a large surface area to volume ratio typically provide the best performance in biological filters.

Chemical filtration removes dissolved particulates from an effluent via activated carbons, resins, and other adsorbents. Chemical filtration media causes unwanted dissolved matter to adhere to it. Two popular forms of chemical media include activated carbon and resins. Activated carbon has microscopic pores that allow certain organic or inorganic materials to stick to them. Carbon removes many harmful elements from an effluent. Ion exchange resins work by attracting a specific molecule to adhere to them. Resins can be combined with carbon. The resins often strengthen the filtering ability of the carbon. Protein foam skimming or oxidation with ozone may also be used for chemical filtration.

Figure 10B:
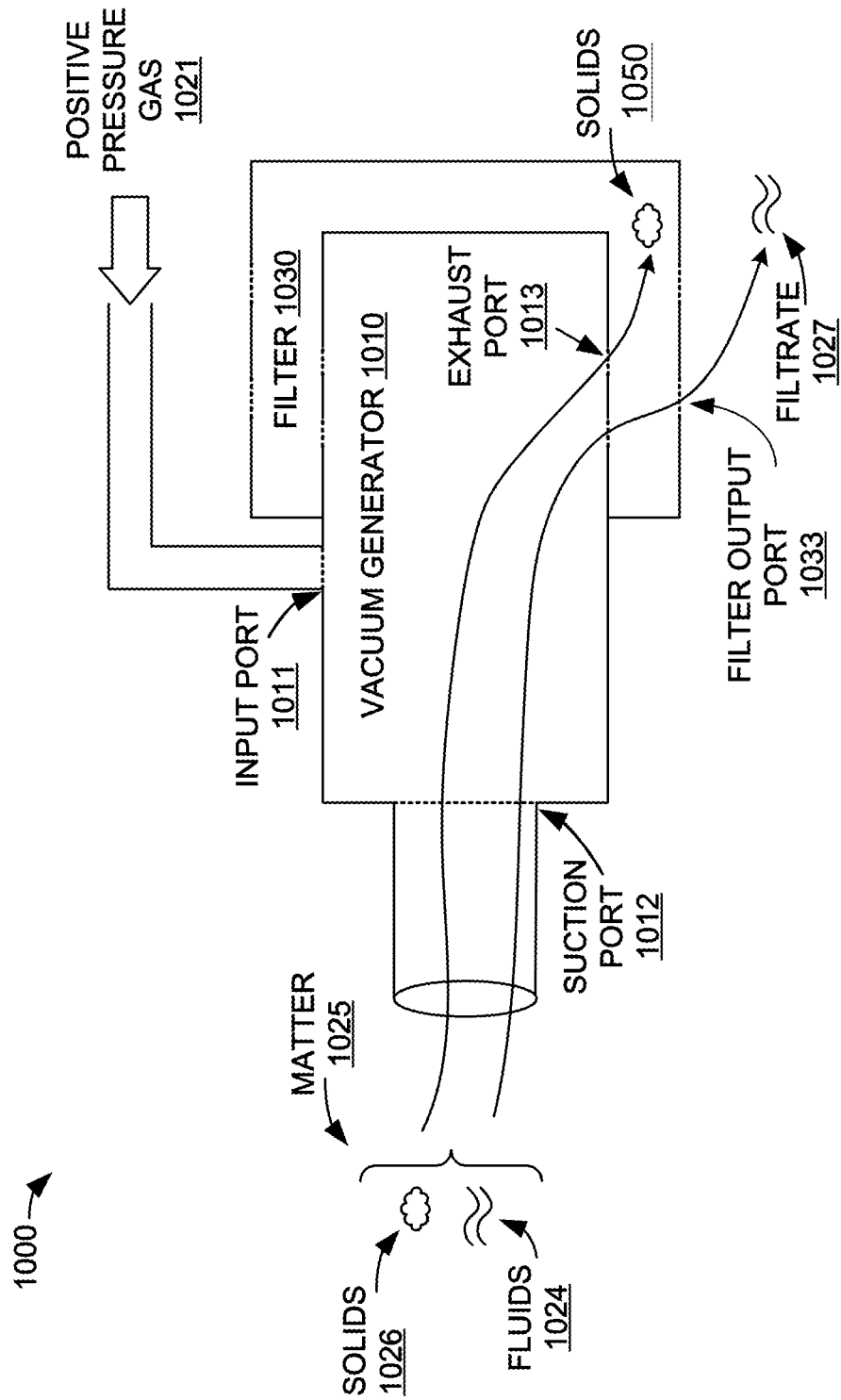
FIG. 10B is a block diagram illustrating the operation of a filtering suction system.

FIG. 10B is a block diagram illustrating the operation of filtering suction system 1000. In operation, vacuum generator 1010 receives positive pressure gas 1021 to generate a low pressure region at suction port 1012 and positive pressure effluent at exhaust port 1013. Vacuum generator 1010 is an example of a flow multiplier. Suction port 1012 pulls matter 1025 (e.g., fluids 1024 and solids 1026) into vacuum generator 1010 by the low pressure region. Matter 1025 pulled into vacuum generator 1010 is propelled by vacuum generator 1010 out of exhaust ports 1013 through filter 1030. Filter 1030 removes solids 1050 and passes filtrate 1027 to exit filter 1030 at filter outlet ports 1033.

Figure 11:
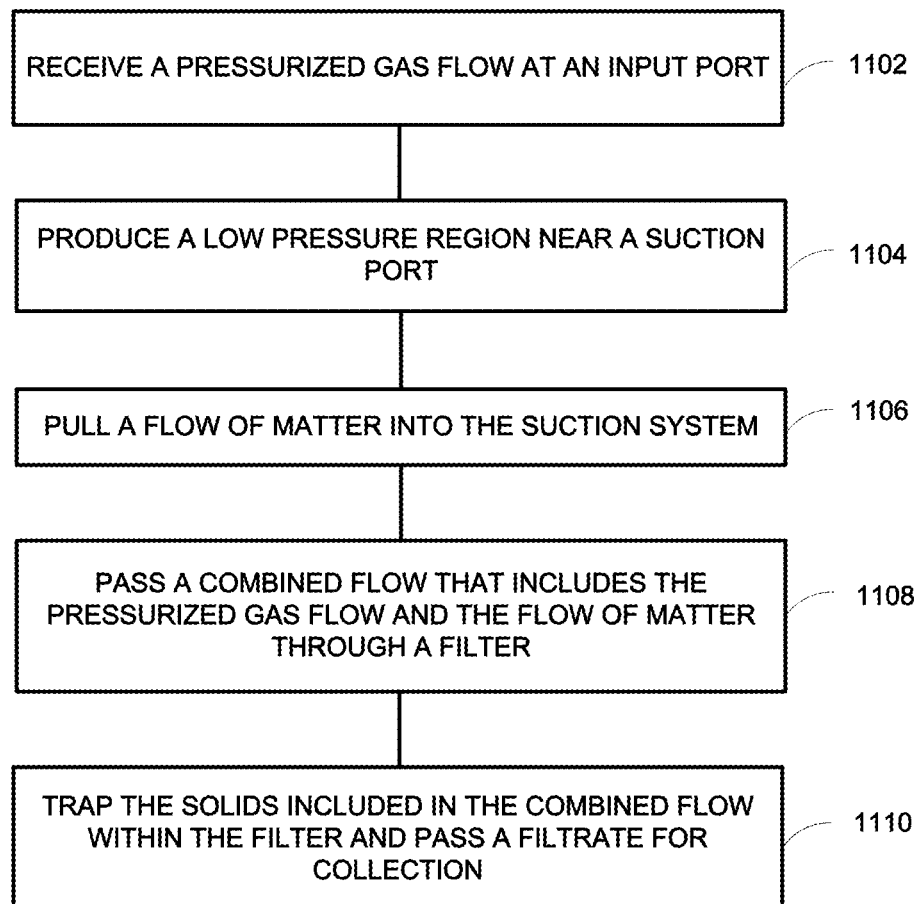
FIG. 11 is a block diagram illustrating a method of operating a filtering suction system.

FIG. 11 is a block diagram illustrating a method of operating a filtering suction system. The steps illustrated in FIG. 11 may be performed by one or more elements of filtering suction system 1000. A pressurized gas flow is received at an input port (1102). For example, input port 1011 is configured to receive positive pressure gas 1021 and supply it to vacuum generator 1010. Vacuum generator 1010 is an example of an air flow multiplier. A low pressure region is produced near a suction port (1104). For example, vacuum generator 1010 is configured to produce low pressure region 1022 near suction port 1012 using positive pressure gas 1021. A flow of matter is pulled into the suction system (1106). For example, low pressure region 1022 is less than an ambient air pressure. This causes a flow of matter to enter suction port 1012. Suction port 1012 is configured to direct the flow of matter through filtering suction system 1000. A combined flow that includes the pressurized gas flow and the flow of matter received at the suction port is passed through a filter (1108). For example, vacuum generator 1010 is configured to pass a combined flow (which can include positive pressure gas 1021 and the flow of matter received at suction port 1012) through filter 1030. The solids included in the combined flow are trapped within a filter and the filtrate is passed through the filter for collection (1110). For example, filter 1030 is configured to trap solids 1050 and pass filtrate 1027 for collection.

Figure 12:
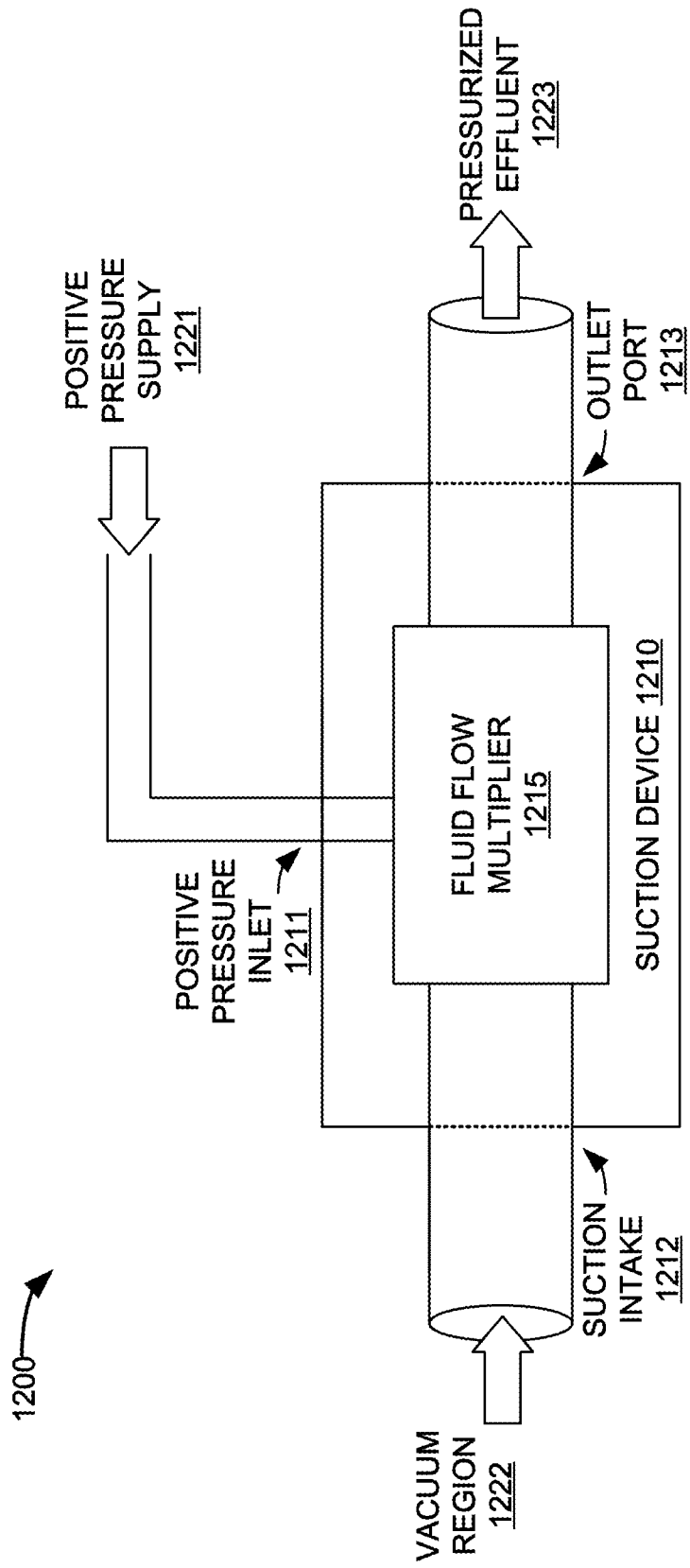
FIG. 12 is a block diagram illustrating a positive pressure operated suction device.

FIG. 12 is a block diagram illustrating positive pressure operated suction device 1200. Positive pressure suction device 1200 is an example of suction system 100; however, positive pressure operated suction device 1200 may have alternative configurations and methods of operation. As illustrated in FIG. 12, positive pressure operated suction device 1200 includes suction device 1210, positive pressure inlet 1211, suction intake 1212, outlet port 1213 and fluid flow multiplier 1215.

Suction device 1210 is configured generate vacuum region 1222 near suction intake 1212 to pull matter into suction device 1210 and expel pressurized effluent out outlet port 1213. Matter may include solids, liquids, and gasses in combination and in variable ratios. In some embodiments, matter may include surgical byproducts. Suction device 1210 is configured to generate vacuum region 1222 from positive pressure supply 1221. In some embodiments, suction device 1210 may take advantage of the Coanda effect to generate vacuum region 1222 from positive pressure supply 1221.

Positive pressure inlet 1211 is configured to receive positive pressure supply 1221 and supply it to fluid flow multiplier 1215. In some embodiments, positive pressure inlet 1211 is configured to supply positive pressure supply 1221 to fluid flow multiplier 1215 at an angle in relation to an interior wall of fluid flow multiplier 1215. Tubing may be used to supply positive pressure supply 1221 to positive pressure inlet 1211. In some embodiments, positive pressure inlet 1211 may include fittings for coupling tubing to positive pressure inlet 1211. Some types of fittings that may be used include barbed, quick-disconnect, or compression fittings.

Suction intake 1212 is disposed towards the distal end of suction device 1210. Suction intake 1212 is configured to receive a flow of matter and supply it to suction device 1210. In operation, vacuum region 1222 pulls a flow of matter into suction intake 1212. Suction intake 1212 supplies the flow of matter to fluid flow multiplier 1215. In some embodiment, suction intake 1212 may include a plurality of openings radially arrayed in the wall of suction intake 1212. The openings provide additional suction near suction intake 1212. In some embodiments, the openings may be configured to take advantage of the Venturi effect. In some embodiments, the openings may be configured to open and close in response to user input.

Outlet port 1213 is configured to direct pressurized effluent 1223 from suction device 1210 to a collection source. In some embodiments, outlet port 1213 may include fittings for coupling to tubing. Some types of fittings that may be used include barbed, quick-disconnect, or compression fittings.

Fluid flow multiplier 1215 is configured to receive positive pressure supply 1221 from positive pressure inlet 1211. In some embodiments, positive pressure inlet 1211 may supply positive pressure supply 1221 to fluid flow multiplier 1215 at an angle in relation to an interior wall of fluid flow multiplier 1215. Fluid flow multiplier 1215 is configured to generate vacuum region 1222 from positive pressure supply 1221 near suction intake 1212. Vacuum region 1222 has a pressure below an ambient air pressure. The ambient air pressure overcomes the pressure in vacuum region 1222 thereby creating suction within suction device 1210. Vacuum region 1222 pulls matter (e.g., liquids, gasses, and solids) into suction intake 1212. Suction intake 1212 is configured to supply the matter to suction device 1210. The matter pulled into suction device 1210 is propelled by fluid flow multiplier 1215 out of outlet port 1213. Outlet port 1213 outputs pressurized effluent 1223 (which can include positive pressure supply 1221 and matter collected at suction intake 1212). Pressurized effluent 1223 may be output to a tube, pipe, etc. for collection, separation, and/or disposal.

It should be understood that the terms 'positive pressure' and 'low pressure' are relative terms. These terms should be understood to be relative to the ambient air/gas pressure in the vicinity of suction device 1210. For example, positive pressure supply 1221 may be a flow of compressed air, nitrogen, carbon dioxide or some other gaseous pressure source. In this case, positive pressure supply 1221 is pressured above the ambient air surrounding suction device 1210. Likewise, vacuum region 1222 may be a region where the air pressure in the vicinity of suction intake 1212 is less than the ambient air. Vacuum region 1222 causes air in the vicinity of suction intake 1212 to flow into suction intake 1212—possibly entraining matter.

In some embodiments, suction device 1210 may be configured for handheld operation. In this configuration, suction device 1210 would be sized and shaped to be held by one or more hands while being operated. Thus, rather than being a permanently mounted (or portable, but large) suction pump, suction device 1210 can be a relatively small device that operates to suction matter into suction intake 1212, and propel matter out of outlet port 1213. It should be understood that while suction device 1210 may be configured for handheld operation, it may also be used with alternative procedures (e.g., laparoscopy, robotic, etc.).

It should be understood that by receiving positive pressure supply 1221, and producing pressurized effluent 1223, tubes and/or pipes connected to positive pressure inlet 1211 and outlet port 1213 can be thin walled and collapsible. The tubes and/or pipes connected to positive pressure inlet 1211 and outlet port 1213 can be collapsible since the positive pressure of positive pressure supply 1221 and pressurized effluent 1223 will 'push open' or 'inflate' the collapsible tubing. Thus, lighter weight and/or less expensive tubing can be used with suction device 1210 than is used with 'negative pressure' systems that rely on a supplied vacuum line or vacuum source (such as a vacuum pump and/or plumbed wall ports).

In some embodiments, fluid flow multiplier 1215 may comprise a structure defining a generally cylindrical cavity having suction intake 1212 at a first end and outlet port 1213 at a second end. The cylindrical cavity is defined by an inner wall of the cavity. Furthermore, the structure may have an annular opening in the inner wall near suction intake 1212 that defines a jet opening adapted to allow positive pressure supply 1221 to flow out of the annular opening such that vacuum region 1222 is produced at suction intake 1212 and a multiplied flow is produced at outlet port 1213. The annular opening may be configured such that positive pressure supply 1221 enters the cavity at an angle with respect towards the inner wall of the cavity near outlet port 1213, the cavity being flared to a larger diameter where the annular opening communicates with the cavity. The annular opening is also configured such that the pressurized gas enters the cavity at an angle (e.g., 0°-90°) with respect to the inner wall of the cavity that is towards the second end. In some embodiments, a more acute angle (e.g., 30°-50°) may be desirable.

A dimension of the gap space, such as an annular opening, may be adjustable to control a pressure difference between ambient air and vacuum region 1222. The annular opening may be configured to include a profile such that positive pressure supply 1221 entering the cavity attaches to a curved surface of the portion of the structure defining the annular opening thereby creating vacuum region 1222, which increases the overall mass flow rate of the multiplied flow. In addition, fluid flow multiplier 1215 may include a structure that is rotatable to adjust the dimension of the annular opening to control the pressure difference. Adjustment of the annular opening allows an operator or user to control a ratio of gas suction to liquid suction provided by fluid flow multiplier 1215.

Figure 13:
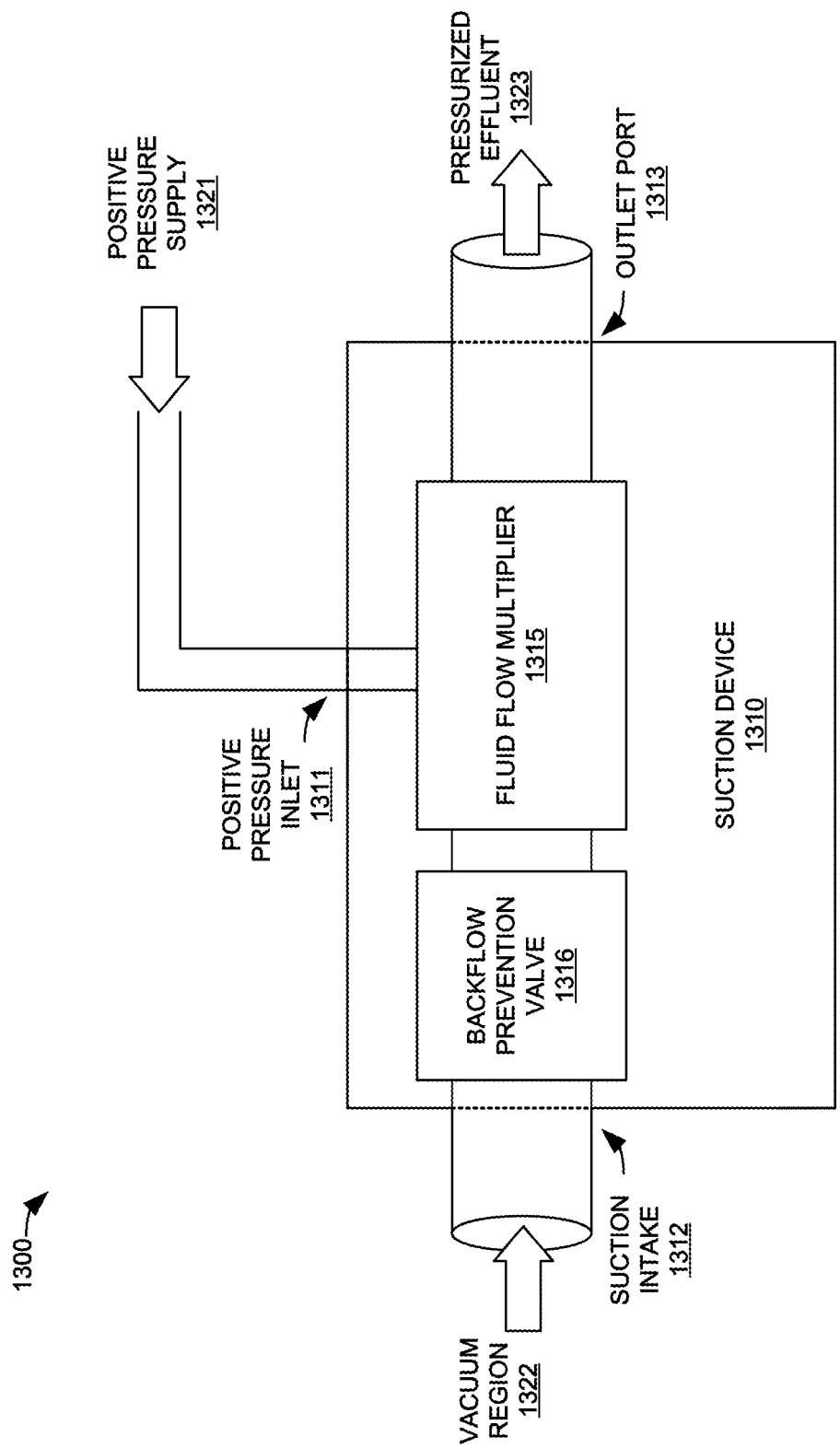
FIG. 13 is a block diagram illustrating a positive pressure operated suction device with backflow prevention.

FIG. 13 is a block diagram illustrating positive pressure operated suction device with backflow prevention 1300. Positive pressure operated suction device with backflow prevention 1300 is an example of positive pressure operation suction device 1200; however, positive pressure operated suction device with backflow prevention 1300 includes backflow prevention valve 1316. Positive pressure operated suction device with backflow prevention 1300 includes suction device 1310, positive pressure inlet 1311, suction intake 1312, outlet port 1313, fluid flow multiplier 1315 and backflow prevention valve 1316.

In operation, suction device 1310 receives positive pressure supply 1321 at positive pressure inlet 1311 and directs positive pressure supply 1321 to fluid flow multiplier 1315 thereby generating vacuum region 1322 near suction intake 1312. Vacuum region 1322 has a pressure below ambient air pressure. The ambient air pressure overcomes the pressure in vacuum region 1322 thereby creating suction within suction device 1310. Vacuum region 1322 pulls matter (e.g., liquids, gasses, and solids) into suction device 1310 via suction intake 1312. In typical operation, the matter pulled into suction device 1310 is propelled by fluid flow multiplier 1315 out outlet port 1313 for collection.

Outlet port 1313 (or a tube connected to carry away pressurized effluent 1323), however, may become clogged or obstructed. When this happens, the obstruction can prevent all or a substantial portion of pressurized effluent 1323 from flowing out of outlet port 1313. Without backflow prevention valve 1316, when pressurized effluent 1323 cannot flow out of outlet port 1313, pressurized effluent 1323 may instead be ejected out of suction intake 1312. The ejection of pressurized effluent 1323 (and of positive pressure supply 1321, in particular) is undesirable and can cause damage or other problems to items in the vicinity of suction intake 1312 (e.g., a patient). However, backflow prevention valve 1316 is configured to at least stop the flow of positive pressure supply 1321 from exiting via suction intake 1312.

Backflow prevention valve 1316 is configured to stop the operation of suction device 1310. Backflow prevention valve 1316 can stop the operation of suction device 1310 by cutting off the supply of positive pressure supply 1321 to one or more components of suction device 1310 that cause vacuum region 1322 to be created. Backflow prevention valve 1316 can stop the operation of suction device 1310 by preventing any 'reverse' flow of matter from exiting via suction intake 1312. For example, backflow prevention valve 1316 may be placed in line with suction intake 1312. Backflow prevention valve 1316 can activate when matter starts to flow in a manner that the flow would exit suction intake 1312. Backflow prevention valve 1316 may be configured such that, once activated, it will stay activated thereby preventing any flow out of suction intake 1312 until positive pressure supply 1321 is removed (i.e., turned off), or the blockage is cleared.

Figure 14:
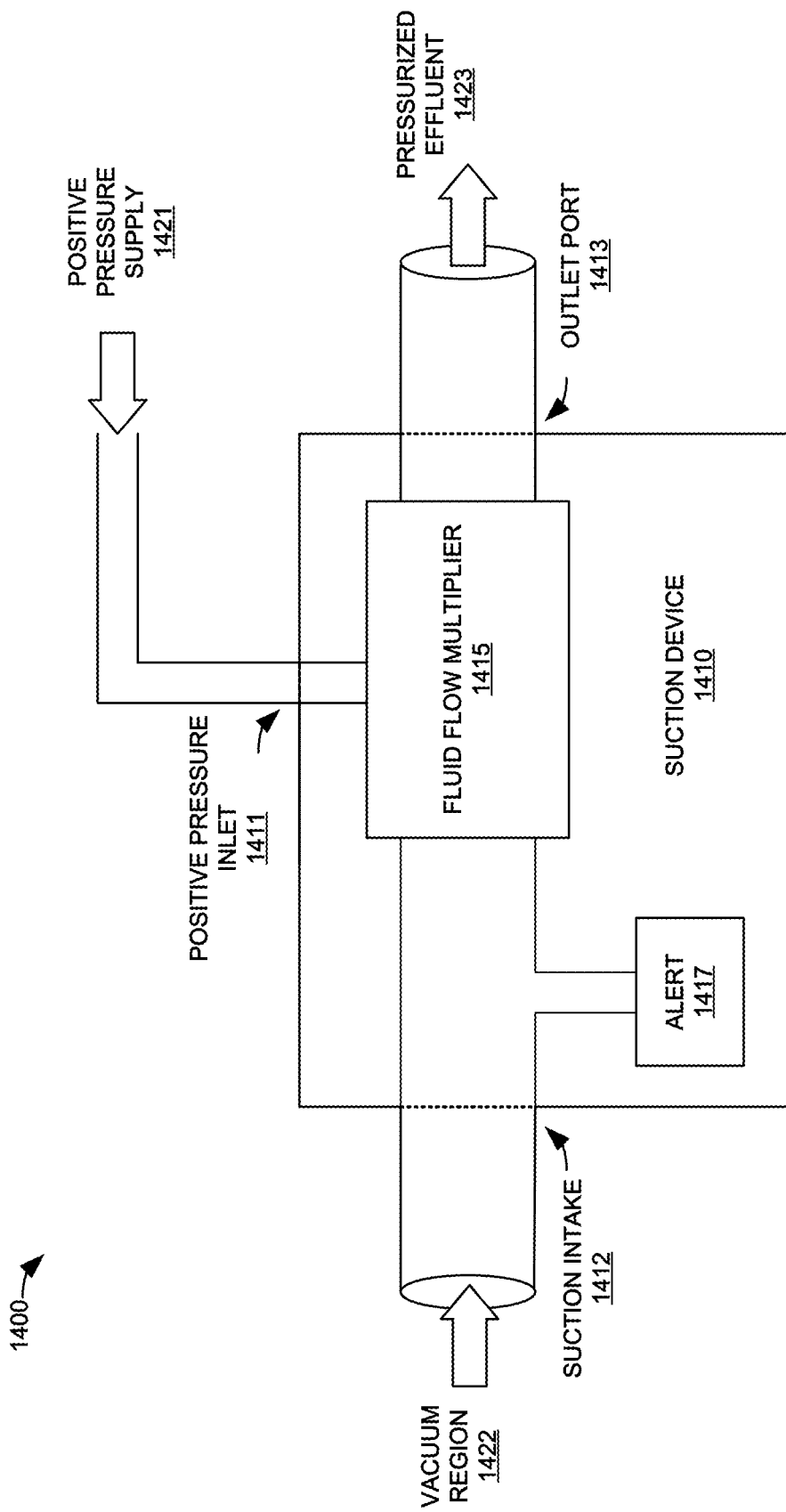
FIG. 14 is a block diagram illustrating a positive pressure operated suction device with backflow alert.

FIG. 14 is a block diagram illustrating positive pressure operated suction device with backflow alert 1400. Positive pressure operated suction device with backflow alert 1400 is an example of positive pressure operated suction device 1200; however, positive pressure operated suction device with backflow alert 1400 includes alert 1417. Positive pressure operated suction device with backflow alert 1000 includes suction device 1410, positive pressure inlet 1411, suction intake 1412, outlet port 1413, fluid flow multiplier 1415 and alert 1417.

In operation, suction device 1410 receives positive pressure supply 1421 to generate vacuum region 1422 at suction intake 1412. Vacuum region 1422 entrains and receives matter into positive pressure operated suction device with backflow alert 1400. Suction port 1412 is configured to entrain and receive surgical byproducts (e.g., smoke, tissue, gasses, liquids, noxious chemicals, etc.) entering suction device 1410. In typical operation, the surgical byproducts pulled into suction device 1410 are propelled by fluid flow multiplier 1415 out of outlet port 1413 as pressurized effluent 1423. Outlet port 1413 is configured to output pressurized effluent 1423 comprising surgical byproducts entrained with positive pressure supply 1421. Pressurized effluent 1423 may be output to a tube, pipe, etc. for collection, separation, and/or disposal.

Outlet port 1413 (or a tube connected to carry away pressurized effluent 1423), however, may become clogged or obstructed. When this happens, the obstruction can prevent all or a substantial portion of pressurized effluent 1423 from flowing out of outlet port 1413. When pressurized effluent 1423 cannot flow out of outlet port 1413, pressurized effluent 1423 may instead be ejected out of suction intake 1412.

Alert 1417 is configured to notify an operator or user of suction device 1410 to the existence of the blockage. Once alerted to a blockage, the user can do one or more of: (1) discontinue use of suction device 1410; (2) clear the blockage thereby restoring normal operation; and (3) terminate the supply of positive pressure supply 1421 thereby shutting off suction device 1410.

Alert 1417 can generate an audible alert (e.g., a whistle or other alarm type noise). Alert 1417 can generate a visible alert (e.g., a flag or other visible indicator). Alert 1417 can generate a tactile alert (e.g., vibration) or some other type of alert to notify the user to the existence of a blockage. Alert 1417 may use mechanical or electrical means to generate an alert. To provide examples of some mechanical means that may be used to generate an alert: Alert 1417 may use positive pressure supply 1421 to generate an audible alert using a whistle type apparatus, a visible alert by physically moving a flag or other visible indicator, or a tactile alert by physically moving a piece of mass. Similarly, various electronic components including transducers, mass airflow sensors and the like may be used by alert 1417 to detect an obstruction or backflow and signal circuitry to activate alert 1417. The various types of alerts described herein may be used individually or in combination.

Figure 15:
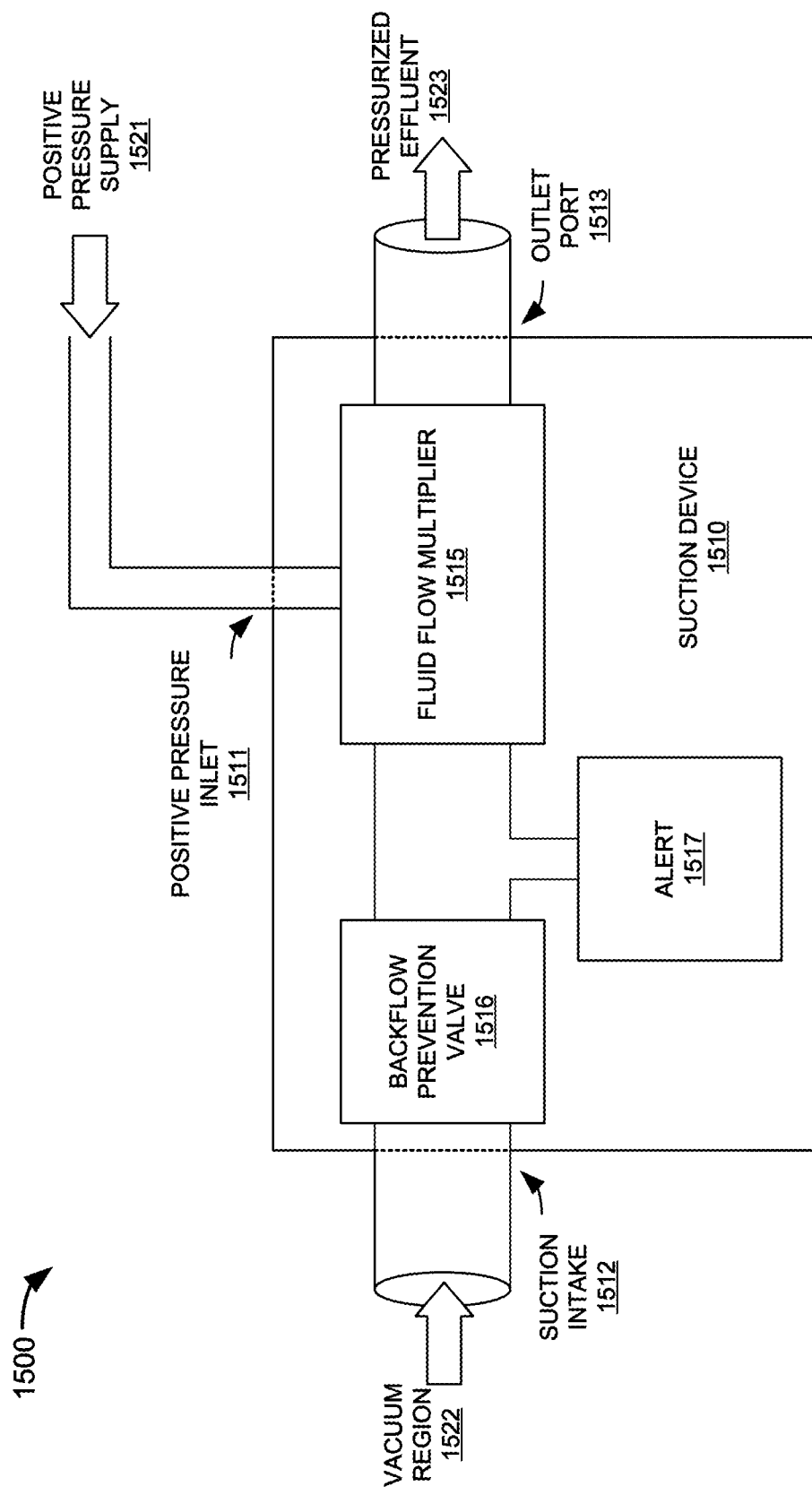
FIG. 15 is a block diagram illustrating a positive pressure operated suction device with safety features.

FIG. 15 is a block diagram illustrating positive pressure operated suction device with safety features 1500. Positive pressure operated suction device with safety features 1100 is an example of positive pressure operated suction device 1200, positive pressure operated suction device with backflow prevention 1300 and positive pressure operated suction device with backflow alert 1400; however, positive pressure operated suction device with safety features 1500 may include alternative configurations and methods of operation.

Positive pressure operated suction device with safety features 1500 includes suction device 1510, positive pressure inlet 1511, suction intake 1512, outlet port 1513, fluid flow multiplier 1515, backflow prevention valve 1516 and alert 1517.

In operation, suction device 1510 receives positive pressure supply 1521 at positive pressure inlet 1511 and directs positive pressure supply 1521 to fluid flow multiplier 1515 thereby generating vacuum region 1522 near suction intake 1512. Vacuum region 1522 has a pressure below ambient air pressure. The ambient air pressure overcomes the pressure in vacuum region 1522 thereby creating suction within suction device 1510. Vacuum region 1522 pulls matter (e.g., liquids, gasses, and solids) into suction device 1510 via suction intake 1512. In typical operation, the matter pulled into suction device 1510 is propelled by fluid flow multiplier 1515 out of outlet port 1513.

Fluid flow multiplier 1115 takes advantage of fluidic dynamic principals including, but not limited to: the Coanda effect, the Venturi effect, fluidic entrainment and fluidic inducement to multiply an effluent flow through suction device 1510. Outlet port 1513 outputs pressurized effluent 1523 of the collected matter and the gasses received via suction intake 1512. Pressurized effluent 1523 may be output to a tube, pipe, etc. for collection, separation, and/or disposal.

Outlet port 1513 (or a tube connected to carry away pressurized effluent 1523), however, may become clogged or obstructed. When this happens, the obstruction can prevent all or a substantial portion of pressurized effluent 1523 from flowing out of outlet port 1513. When pressurized effluent 1523 cannot flow out of outlet port 1513, pressurized effluent 1523 may instead be ejected out of suction intake 1512.

Backflow prevention valve 1516 can stop the operation of suction device 1510 by cutting off the supply of positive pressure supply 1521 to one or more components of suction device 1510 that cause vacuum region 1522 to be created. Backflow prevention valve 1516 can stop the operation of suction device 1510 by preventing any 'reverse' flow of matter from exiting via suction intake 1512. For example, backflow prevention valve 1516 may be placed in line with suction intake 1512. Backflow prevention valve 1516 can activate when matter starts to flow in a manner that the flow would exit suction intake 1512. Backflow prevention valve 1516 may be configured such that, once activated, it will stay activated thereby preventing any flow out of suction intake 1512 until positive pressure supply 1521 is removed (i.e., turned off), or the blockage is cleared.

Alert 1517 is configured to alert a user of suction device 1510 to the existence of a blockage. Once alerted to a blockage, the user can do one or more of: (1) discontinue use of suction device 1510; (2) clear the blockage thereby restoring normal operation; and (3) terminate the supply of positive pressure supply 1521 thereby shutting off suction device 1510.

Backflow prevention valve 1516 may be operatively coupled to alert 1517 in order to activate alert 1517 in response to the activation of backflow prevention valve 1516. In this manner, in response to a blockage, suction device 1510 both stops (i.e., prevents) the reverse flow of pressurized effluent 1523 out of suction intake 1512 as well as alerts the user to the blockage.

Alert 1517 can generate an audible alert (e.g., a whistle or other alarm type noise), a visible alert (e.g., a flag or other visible indicator), a tactile alert (e.g., vibration) or some other type of alert to notify the user to the existence of a blockage. Alert 1517 may use mechanical or electrical means to generate an alert. The various types of alerts described herein may be used individually or in combination.

Figure 16:
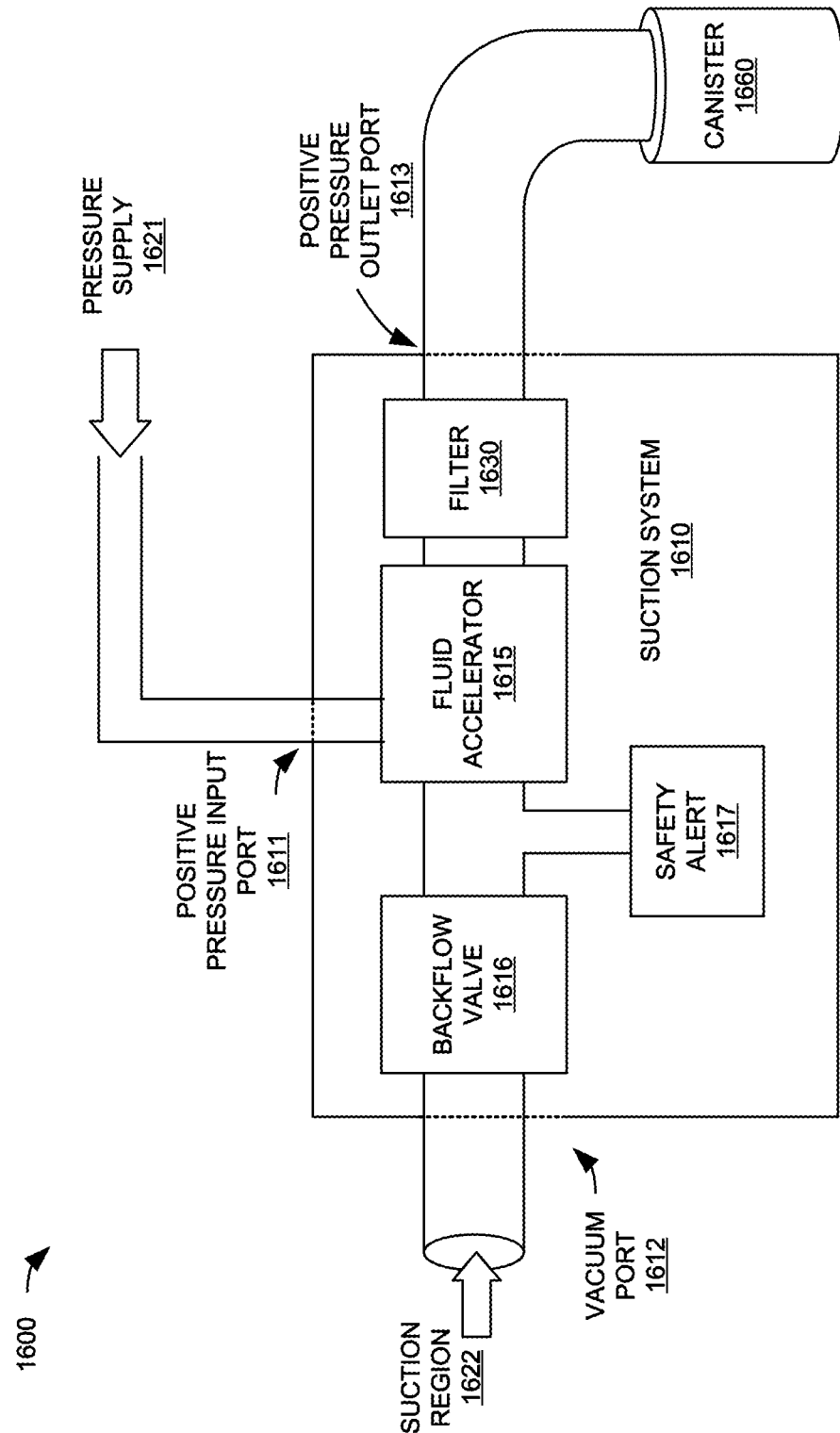
FIG. 16 is a block diagram illustrating a filtering suction device with safety features.

FIG. 16 is a block diagram illustrating filtering suction device with safety features 1600. Positive pressure operated suction device with safety features 1600 is an example of positive pressure operated suction device 1200, positive pressure operated suction device with backflow prevention 1300, positive pressure operated suction device with backflow alert 1400 and Positive pressure operated suction device with safety features 1500; however, filtering suction device with safety features 1600 includes filter 1630 and canister 1660. Filtering suction device with safety features 1600 includes suction system 1610, positive pressure input port 1611, vacuum port 1612, positive pressure outlet port 1613, fluid accelerator 1615, backflow valve 1616, safety alert 1617, filter 1630 and canister 1660.

Canister 1660 is configured to receive waste output from positive pressure outlet port 1613 for collection, separation, and/or disposal. In some embodiments, canister 1660 may be a suction canister connected to a vacuum source. In some embodiments, canister 1660 may include a filter. Canister 1660 may be manufactured from plastic, glass, metal or some other material having desirable properties. Some desirable properties may include: cost, ability to be sterilized, manufacturing method, application or some other metric.

In operation, suction system 1610 receives pressure supply 1621 at positive pressure input port 1611 and directs pressure supply 1621 to fluid accelerator 1615 thereby generating suction region 1622 at vacuum port 1612. Suction region 1622 has a pressure below ambient air pressure. The ambient air pressure overcomes the pressure in suction region 1622 thereby creating suction within suction system 1610. Suction region 1622 pulls matter (e.g., liquids, gasses, and solids) into suction system 1610 via vacuum port 1612. In typical operation, the matter pulled into suction system 1610 is propelled by fluid accelerator 1615 through filter 1630 and a filtrate is directed out positive pressure outlet port 1613. Positive pressure outlet port 1613 directs a filtrate to canister 1660.

Fluid accelerator 1615 is configured to couple to filter 1630. Fluid accelerator 1615 uses pressure supply 1621 to push an effluent through filter 1630. Filter 1630 is configured to trap matter and pass a filtrate to positive pressure outlet port 1612. Positive pressure output 1613 is configured to couple to canister 1660. Positive pressure output 1613 supplies a filtrate from suction system 1610 to canister 1660. In some embodiments, canister 1660 may be connected to a vacuum supply.

Positive pressure outlet port 1613, filter 1630 or canister 1660, however, may become clogged or obstructed. When this happens, the obstruction can prevent all or a substantial portion of an effluent from flowing out of positive pressure outlet port 1613. When the effluent cannot flow out of positive pressure outlet port 1613, the effluent may instead be ejected out of vacuum port 1612.

Backflow valve 1616 can stop the operation of suction system 1610 by cutting off the supply of pressure supply 1621 to one or more components of suction system 1610 that cause suction region 1622 to be created. Backflow valve 1616 can stop the operation of suction system 1610 by preventing any 'reverse' flow of matter from exiting via vacuum port 1612. For example, backflow valve 1616 may be placed in line with vacuum port 1612. Backflow valve 1616 can activate when matter starts to flow in a manner that the flow would exit vacuum port 1612. Backflow valve 1616 may be configured such that, once activated, it will stay activated thereby preventing any flow out of vacuum port 1612 until pressure supply 1621 is removed (i.e., turned off), or the blockage is cleared.

Safety alert 1617 is configured to alert a user of suction system 1610 to the existence of a blockage. Once alerted to a blockage, the user can do one or more of: (1) discontinue use of suction system 1610; (2) clear the blockage thereby restoring normal operation; and (3) terminate the supply of pressure supply 1621 thereby shutting off suction system 1610.

Safety alert 1617 may be operatively coupled to backflow valve 1616 in order to activate safety alert 1617 in response to the activation of backflow valve 1616. In this manner, in response to a blockage, suction system 1610 both stops (i.e., prevents) the reverse flow of an effluent out of vacuum port 1612 as well as alerts the user to the blockage.

Figure 17:
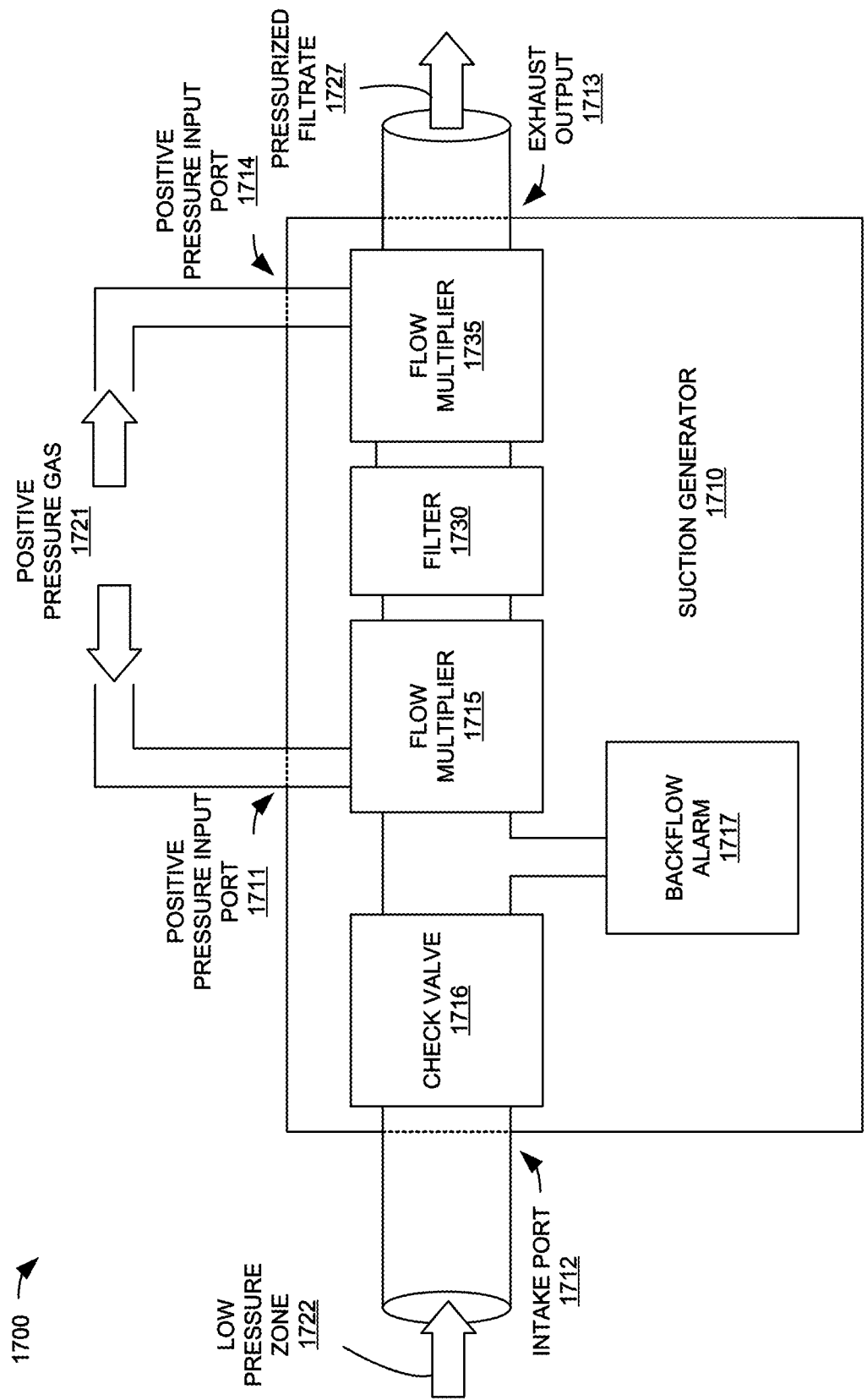
FIG. 17 is a block diagram illustrating a compensated filtering suction device.

FIG. 17 illustrates compensated filtering suction device 1700. Compensated filtering suction device 1700 is an example of positive pressure operated suction device 1200, positive pressure operated suction device with backflow prevention 1300, positive pressure operated suction device with backflow alert 1400, positive pressure operated suction device with safety features 1500 and filtering suction device with safety features 1600; however, compensated filtering suction device 1700 includes flow multiplier 1735. Compensated filtering suction device 1700 includes suction generator 1710, positive pressure input port 1711, intake port 1712, exhaust output 1713, flow multiplier 1715, check valve 1716, backflow alarm 1717, filter 1730 and flow multiplier 1735. Flow multiplier 1735 is configured to compensate for flow resistance through filter 1730 by creating a low pressure region between filter 1730 and flow multiplier 1735.

In operation, suction generator 1710 receives positive pressure gas 1721 at positive pressure input ports 1711, 1714 and directs positive pressure gas 1721 to flow multipliers 1715, 1735, respectively. Flow multipliers 1715, 1735 are configured to generate low pressure regions distal to flow multipliers 1715, 1735 from positive pressure gas 1721. The combined low pressure regions produce low pressure zone 1722 near intake port 1712. Low pressure zone 1722 has a pressure below ambient air pressure. The ambient air pressure overcomes the pressure in low pressure zone 1722 thereby creating suction within suction generator 1710. Low pressure zone 1722 pulls matter (e.g., liquids, gasses, and solids) into suction generator 1710 via intake port 1712. In typical operation, the matter pulled into suction generator 1710 is propelled by flow multipliers 1715, 1735 through filter 1730 and out exhaust output 1713.

Flow multipliers 1715, 1735 may each take advantage of fluidic dynamic principals including, but not limited to: the Coanda effect, the Venturi effect, fluidic entrainment and fluidic inducement to create and accelerate an effluent flow through suction generator 1710. The Coanda effect may be used by flow multipliers 1715, 1735 on either side of filter 1730. While FIG. 17 only illustrates flow multipliers 1715 and 1735, it should be understood that a plurality of flow multipliers, similar to flow multipliers 1715 and 1735, may be combined in series or parallel operation before or after filter 1730.

Exhaust output 1713 and/or filter 1730 (or a tube connected to carry away pressurized filtrate 1727), however, may become clogged or obstructed. When this happens, the obstruction can prevent all or a substantial portion of an effluent from flowing out of exhaust output 1713. When the effluent cannot flow out of exhaust output 1713, the effluent may instead be ejected out of intake port 1712. The flow of positive pressure gas 1721 may be reversed to flow out of intake port 1712 if an obstruction blocks exhaust output 1713—thereby giving positive pressure gas 1721 nowhere else to flow but out of intake port 1712.

Check valve 1716 can stop the operation of suction generator 1710 by cutting off the supply of positive pressure gas 1721 to one or more components of suction generator 1710 that cause low pressure zone 1722 to be created. Check valve 1716 can stop the operation of suction generator 1710 by preventing any 'reverse' flow of matter from exiting via intake port 1712. For example, check valve 1716 may be placed in line with intake port 1712. Check valve 1716 can activate when matter starts to flow in a manner that the flow would exit intake port 1712. Check valve 1716 may be configured such that, once activated, it will stay activated thereby preventing any flow out of intake port 1712 until positive pressure gas 1721 is removed (i.e., turned off), or the blockage is cleared.

Backflow alarm 1717 is configured to alert a user of suction generator 1710 to the existence of a blockage. Backflow alarm 1717 may be operatively coupled to check valve 1716 to activate backflow alarm 1717 in response to the activation of check valve 1716. In this manner, in response to a blockage, suction generator 1710 both stops (i.e., prevents) the reverse flow of an effluent out of intake port 1712 as well as alerts the user to the blockage.

Filter 1730 may comprise mechanical, biological, chemical or other types of filters including any combination thereof. Filter 1730 includes at least one filter inlet port and at least one filer output port. The at least one filter inlet port is coupled to flow multiplier 1715 so that surgical byproducts and positive pressure gas 1721 pass through filter 1730. The at least one filter output port is coupled to flow multiplier 1735.

Suction generator 1710 includes flow multiplier 1735. Flow multiplier 1735 is in fluid communication with an input port of filter 1730. In operation, flow multiplier 1735 receives positive pressure gas 1721 at positive pressure input port 1714 to produce a low pressure zone between filter 1730 and flow multiplier 1735. Flow multiplier 1735 may be configured to compensate for flow and/or pressure (suction) losses attributable to the flow resistance of filter 1730. For example, flow multiplier 1735 may compensate for a portion (e.g., ½, etc.) of the flow resistance of filter 1730. Flow multiplier may be configured to compensate for more of the flow resistance (e.g., 1.25×, 1.5× or 2×) of filter 1730. Flow multiplier 1735 is coupled to exhaust output 1713. Flow multiplier 1735 is configured to exhaust a filtrate from filter 1730 out exhaust output 1713.

Figure 18:
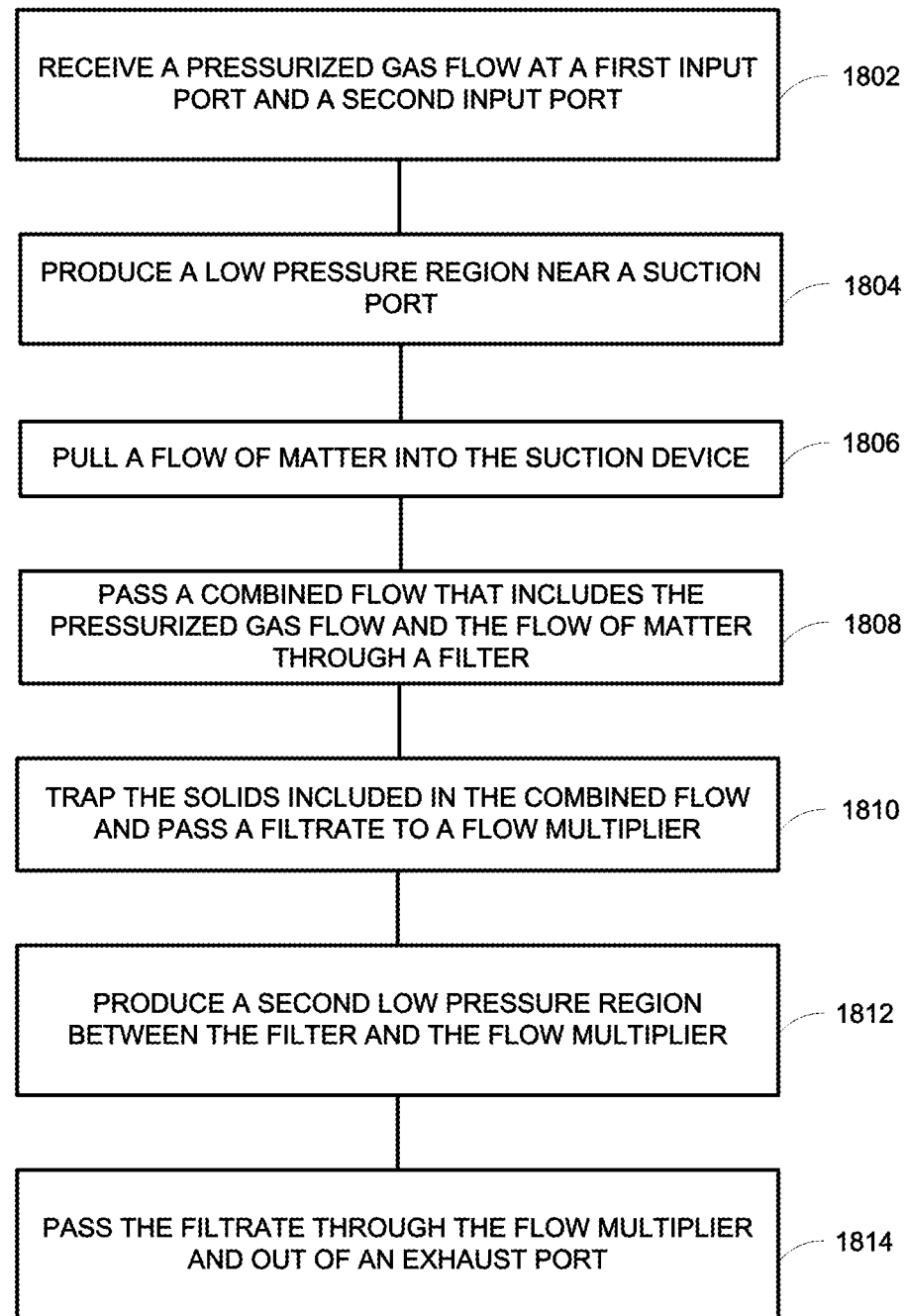
FIG. 18 is a block diagram illustrating a method of operating a compensated filtering suction device.

FIG. 18 is a block diagram illustrating a method of operating a compensated filtering suction device. The steps illustrated in FIG. 18 may be performed by one or more elements of compensated filtering suction device 1700. A pressurized gas flow is received at a first input port and a second input port (1802). For example, positive pressure input port 1711 is configured to receive positive pressure gas 1721 and supply it to flow multiplier 1715. Positive pressure input port 1714 is configured to receive positive pressure gas 1721 and supply it to flow multiplier 1735. A low pressure region is produced near a suction port (1804). For example, suction generator 1710 is configured to produce low pressure zone 1722 near intake port 1712 by directing positive pressure gas 1721 through flow multipliers 1715, 1735. A flow of matter is pulled into the suction device (1806). For example, low pressure zone 1722 is less than an ambient air pressure. This causes a flow of matter to enter intake port 1712. Intake port 1712 is configured to receive a flow of matter and direct the flow of matter through suction generator 1710. A combined flow that includes the pressurized gas flow and the flow of matter is passed through a filter (1808). For example, flow multiplier 1715 is configured to direct a combined flow (which can include positive pressure gas 1721 and the flow of matter received at intake port 1712) through filter 1730. Particles included in the combined flow are trapped in the filter and a filtrate is passed through the filter to a second flow multiplier (1810). For example, filter 1730 is disposed between flow multiplier 1715 and flow multiplier 1735. Filter 1730 is configured to trap particles and direct a filtrate to flow multiplier 1735. A low pressure region is produced between the filter and a flow multiplier (1812). For example, flow multiplier 1735 is disposed between filter 1730 and exhaust output 1713. Flow multiplier 1735 is configured to produce a low pressure region between filter 1730 and flow multiplier 1735. The filtrate is passed through a flow multiplier and out of an exhaust port (1814). Flow multiplier 1735 is configured to receive a filtrate from filter 1730 and pass the filtrate out exhaust port 1713.

Figure 19:
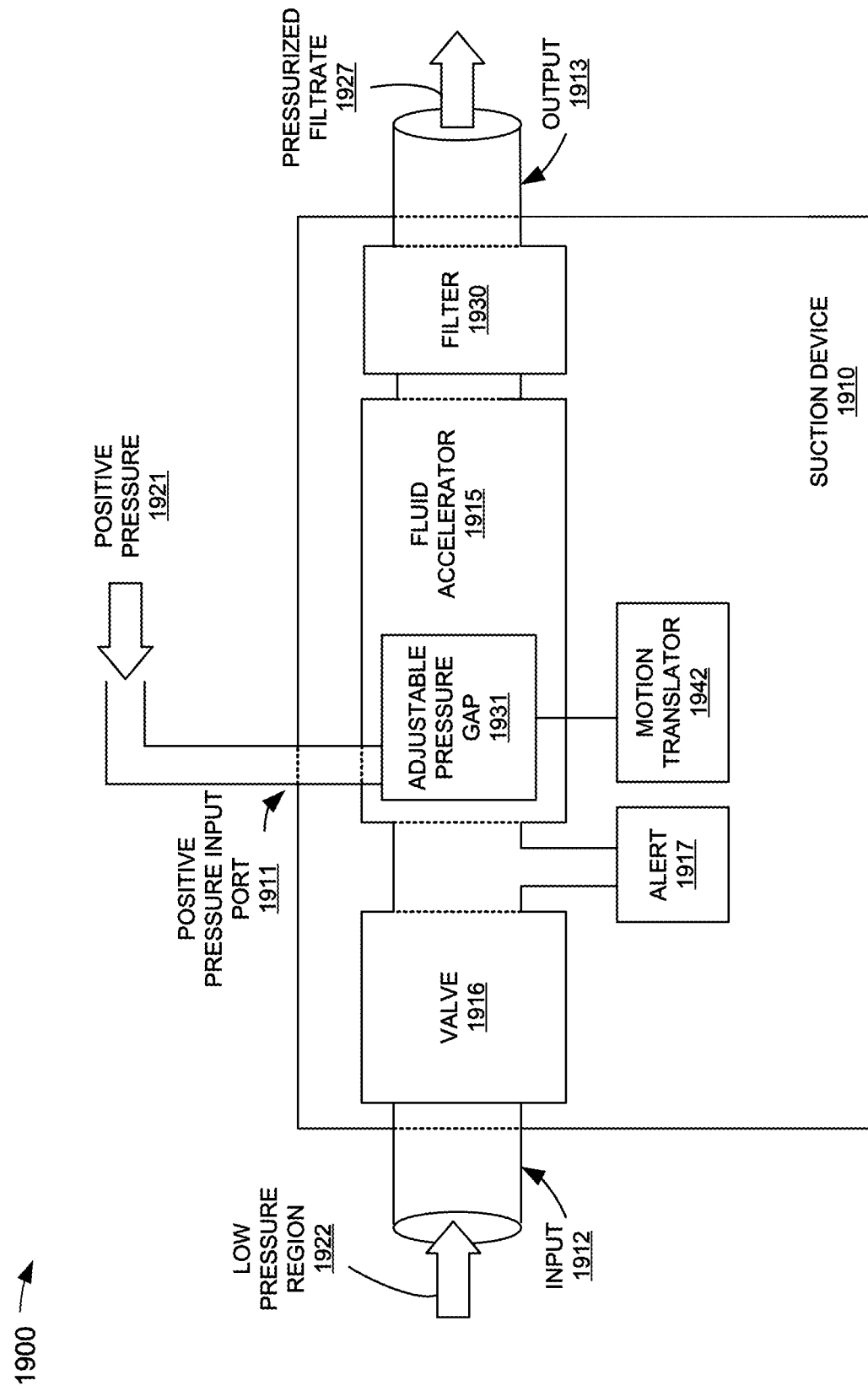
FIG. 19 is a block diagram illustrating a suction device with adjustable pressure gap.

FIG. 19 is a block diagram illustrating suction device with adjustable pressure gap 1900. Suction device with adjustable pressure gap is an example of suction system 100, suction system with backflow prevention 300, suction system with backflow alert 400, suction system with safety features 500, filtering suction system 1000, positive pressure operated suction device 1200, positive pressure operated suction device with backflow prevention 1300, positive pressure operated suction device with backflow alert 1400, positive pressure operated suction device with safety features 1500 and filtering suction device with safety features 1600; however, suction device with adjustable pressure gap 1900 includes adjustable pressure gap 1931 and motion translator 1942. Suction device with adjustable pressure gap 1900 includes suction device 1910, positive pressure input port 1911, input 1912, output 1913, fluid accelerator 1915, valve 1916, alert 1917, filter 1930, adjustable pressure gap 1931 and motion translator 1942.

Positive pressure input port 1911 is configured to receive positive pressure 1921. Positive pressure input port includes a means for coupling to a positive pressure source. In operation, positive pressure input port 1911 directs positive pressure 1921 to adjustable pressure gap 1931.

Adjustable pressure gap 1931 includes an annular opening that directs positive pressure 1921 into fluid accelerator 1915. A dimension of adjustable pressure gap 1931 may be adjusted in response to motion translator 1942 receiving a user input. The pressure difference between low pressure region 1922 and an ambient air pressure may be controlled by adjustable pressure gap 1931. For example, increasing the dimension of adjustable pressure gap 1931 can increase the pressure difference between low pressure region 1922 and an ambient air pressure. Decreasing the dimension of adjustable pressure gap 1931 can decrease the pressure difference between low pressure region 1922 and an ambient air pressure. A user may choose to vary the pressure difference between low pressure region 1922 and an ambient air pressure depending upon the type of matter the user would like to suction. For example, a user may adjust the pressure difference between low pressure region 1922 and an ambient air pressure to suction more smoke than liquids. Alternatively, a user may adjust the pressure difference between low pressure region 1922 and an ambient air pressure to suction liquids.

Motion translator 1942 is configured to translate a user input into an adjustment of adjustable pressure gap 1931. In some embodiments, motion translator 1942 is configured to translate a large motion from a user input into a smaller motion for adjusting a dimension of adjustable pressure gap 1931. In some embodiments, motion translator 1942 is configured to include a rotatable element that translates a rotational user input into a linear adjustment of a dimension of adjustable pressure gap 1931. In some embodiments, motion translator may include a sliding member to adjust a dimension of adjustable pressure gap 1931. In some embodiments, motion translator 1931 may include a lever to convert a larger user input motion into a smaller user input motion to adjust a dimension of adjustable pressure gap 1931.

Figure 20:
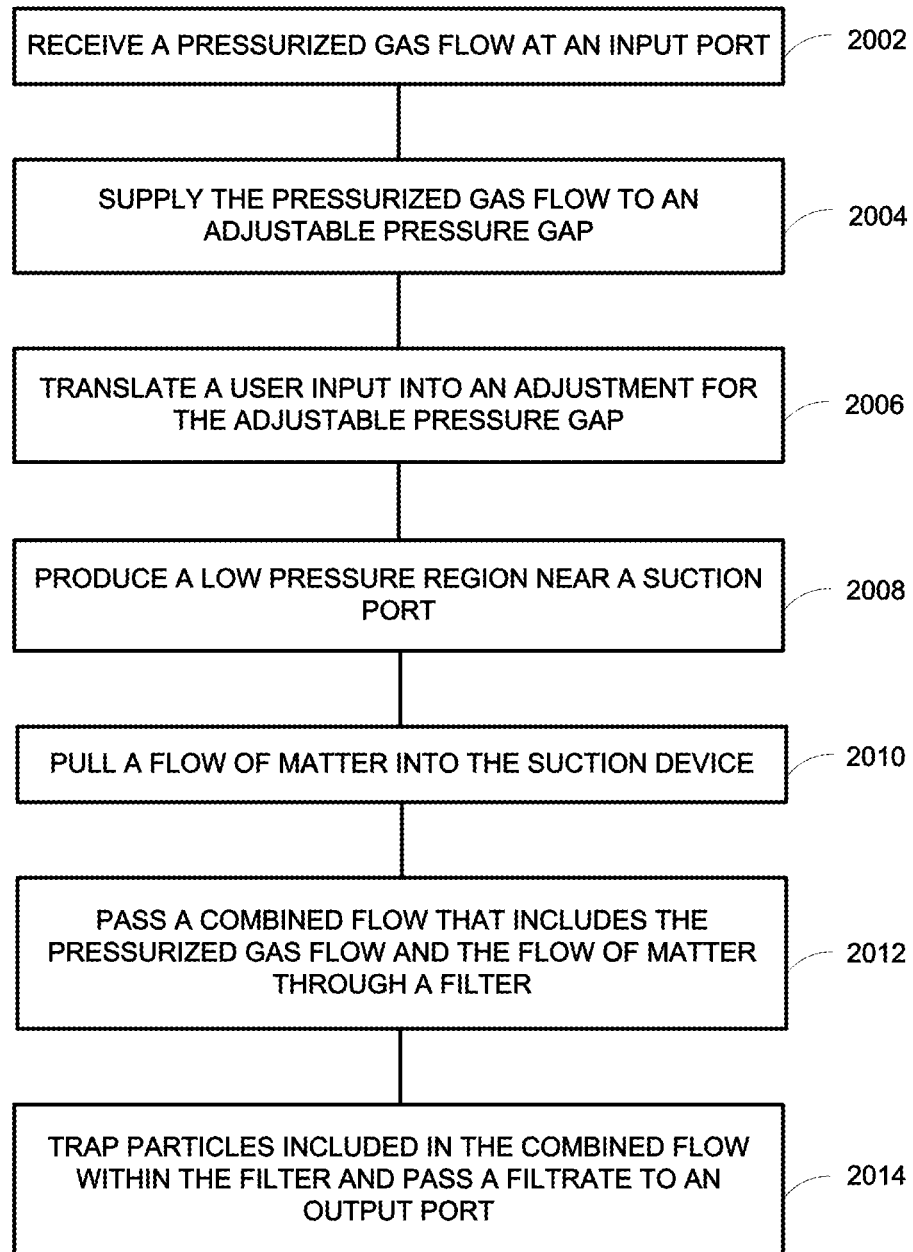
FIG. 20 is a diagram illustrating a method of operating a suction device with adjustable pressure gap.

FIG. 20 is a diagram illustrating a method of operating a suction device with adjustable pressure gap. The steps illustrated in FIG. 20 may be performed by one or more elements of suction device with adjustable pressure gap 1900. A pressurized gas flow is received at an input port (2002). For example, suction device with adjustable pressure gap 1900 includes input port 1911 configured to receive positive pressure 1921 and supply it to adjustable pressure gap 1931. The pressurized gas flow is supplied to an adjustable pressure gap (2004). For example, positive pressure input port 1911 is coupled to adjustable pressure gap 1931. Positive pressure input port 1911 is configured to supply positive pressure 1921 to adjustable pressure gap 1931. A user input is translated into an adjustment for the adjustable pressure gap (2006). For example, motion translator 1942 is configured to receive a user input and translate the user input into an adjustment for adjustable pressure gap 1931. A low pressure region is produced near a suction port (2008). For example, fluid accelerator 1915 is configured produce low pressure region 1922 near input 1012 from positive pressure 1921. Adjustable pressure gap 1931 is configured to be adjustable to change the pressure difference between low pressure region 1922 and an ambient air pressure. A flow of matter is pulled into the suction device (2010). For example, fluid accelerator 1915 produces low pressure region 1922 below an ambient air pressure. This causes a flow of matter to be pulled into suction device 1910. A combined flow that includes the pressurized gas flow and the flow of matter received at the suction port is passed through a filter (2012). For example, fluid accelerator 1915 is coupled to filter 1930. Fluid accelerator 1915 is configured to pass a combined flow (which can include positive pressure 1921 and a flow of matter received at input 1912) through filter 1930. Particles included in the combined flow are trapped within the filter and a filtrate is passed through the filter to an output port (2014). For example, filter 1930 is configured to trap solids and pass pressurized filtrate 1927 to output 1913.

Figure 21A:
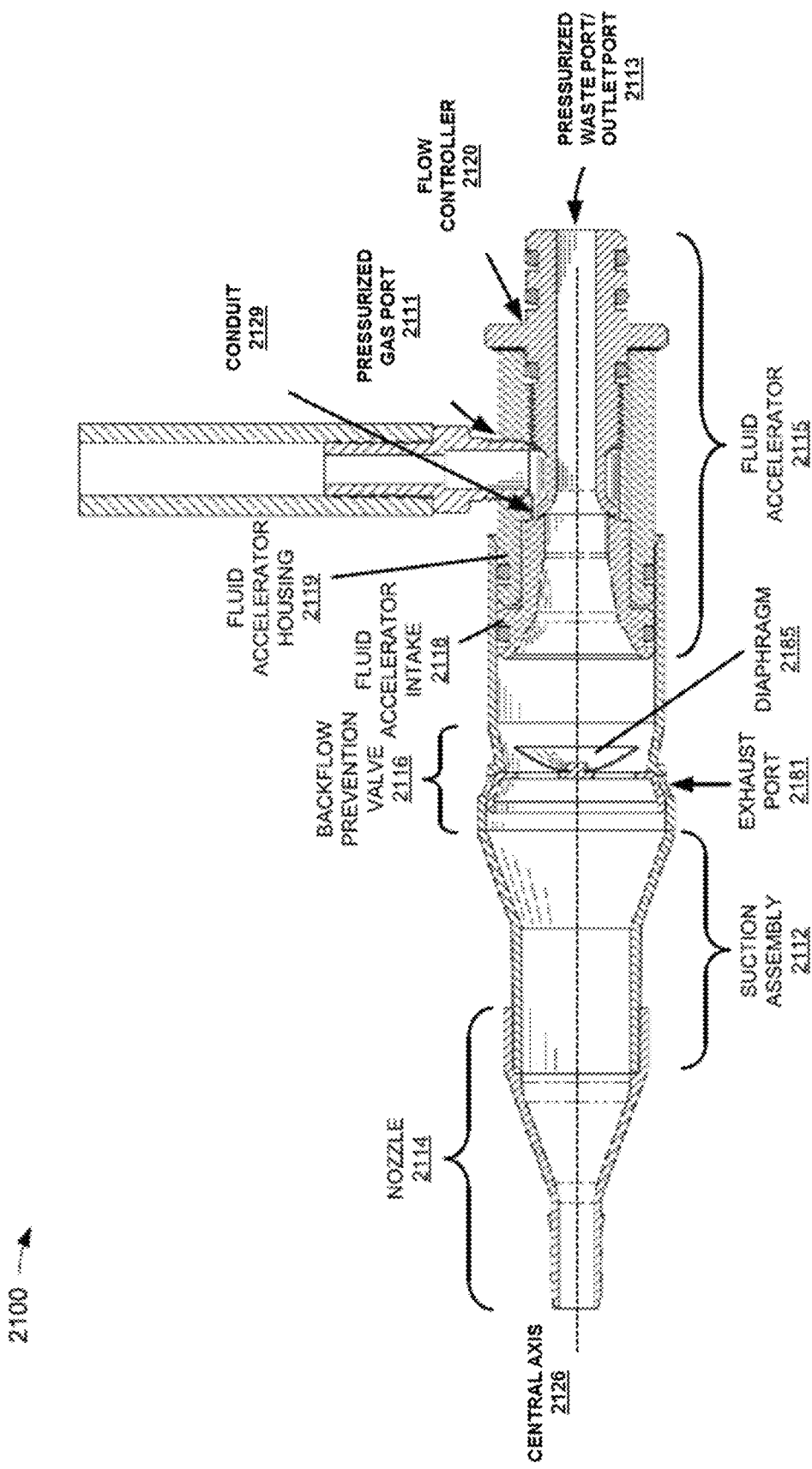
FIG. 21A is a diagram illustrating a suction device with backflow prevention valve.

FIG. 21A is a block diagram illustrating suction device with backflow prevention valve 2100. Suction device with backflow prevention valve 2100 is an example of suction device 100, suction system with backflow prevention 300, positive pressure operated suction device 1200, positive pressure operated suction device with backflow prevention 1300 and suction device with adjustable pressure gap 1900; however, suction device with backflow prevention valve 2100 may include alternative configurations and methods of operation. As illustrated in FIG. 21A, suction device with backflow prevention valve 2100 includes pressurized gas port (such as a positive pressure intake) 2111, suction assembly 2112, nozzle 2114, fluid accelerator 2115, and backflow prevention valve 2116.

Suction device with backflow prevention valve 2100 uses a Coanda effect based fluid accelerator 2115 to create suction near nozzle 2114. The suction is primarily created by suction device with backflow prevention valve 2100 from a flow of positive pressure supply 2121 (typically pressurized above ambient) that is provided to fluid accelerator 2115—not an external suction pump (although the device may be used in conjunction with a suction pump). Suction device with backflow prevention 2100 may be used for removing medical or surgical byproducts, such as smoke, tissue, and body fluids. Suction device with backflow prevention valve 2100 includes backflow prevention valve 2116 that prevents the flow of pressurized gas from 'reversing' direction and flowing out of nozzle 2114 in the wrong direction. In other words, suction device with backflow prevention valve 2100 is configured to prevent the pressurized gas from flowing out nozzle 2114—which may cause problems or injure a patient.

Suction device with backflow prevention valve 2100 includes pressurized gas port 2111. Pressurized gas port 2111 is configured to receive positive pressure supply 2121 and supply it to conduit 2129 (such as an annular opening). A dimension of conduit 2129 is adjustable via flow controller 2120 to control the difference between a low pressure region generated near nozzle 2114 and an ambient air pressure. Tubing may be used to supply positive pressure supply 2121 to pressurized gas port 2111. In some embodiments, pressurized gas port 2111 may include fittings for coupling tubing to pressurized gas port 2111. Some types of fittings that may be used include barbed, quick-disconnect, or compression fittings.

Suction device with backflow prevention valve 2100 includes suction assembly 2112. Suction assembly 2112 is disposed towards the distal end of suction device with backflow prevention valve 2100. Suction assembly 2112 is configured to house backflow prevention valve 2116. Suction assembly includes exhaust ports 2181 configured to direct at least the flow of positive pressure supply 2121 out exhaust ports 2181 when backflow prevention valve is activated.

Suction device with backflow prevention valve 2100 includes nozzle 2114. FIG. 21A illustrates an embodiment of nozzle 2114 including a conical cavity having a narrow distal end and a wide proximal end. The narrow distal end may be configured to include press-fit friction fittings, barbs, threads, Luer fittings or some other means to attach accessories (e.g., tubing, needles, etc.) to nozzle 2114. Nozzle 2114 includes a proximal end configured to couple to suction assembly 2112. Nozzle 2114 is configured to receive flow of matter/suction flow 2124 and supply it to suction assembly 2112. Nozzle 2114 is configured to be replaceable. Different embodiments of nozzle 2114 configured for specific applications may be used with suction device with backflow prevention valve 2100. In some embodiment, nozzle 2114 may include openings radially arrayed in the wall of nozzle 2114. The openings provide additional suction near nozzle 2114. In some embodiments, the openings may be configured to take advantage of the Venturi effect. In some embodiments, the openings may be configured to open and close in response to a user input.

Suction device with backflow prevention valve 2100 includes fluid accelerator 2115. Fluid accelerator 2115 includes fluid accelerator intake 2118, fluid accelerator housing 2119, flow control 2120 and conduit 2129. Fluid accelerator 2115 is configured to generate a low pressure region near nozzle 2114 from positive pressure supply 2121. Fluid accelerator 2115 may be configured to take advantage of the Coanda effect. Fluid accelerator 2115 is configured to receive positive pressure supply 2121 to produce a first low pressure region near nozzle 2114. Fluid accelerator is configured to accelerate flow of matter/suction flow 2124 received at nozzle 2114 and eject positive pressure effluent 2123 (which can include positive pressure supply 2121 and flow of matter/suction flow 2124) out pressurized waste port/outlet port 2113. The pressure difference between the low pressure region generated near nozzle 2114 and an ambient air pressure may be adjusted by flow controller 2120. Flow controller 2120 may be adjusted to suction more gasses than liquids. Flow controller 2120 may be adjusted to suction liquids.

Fluid accelerator 2115 includes fluid accelerator intake 2118. Fluid accelerator intake 2118 is disposed between backflow prevention valve 2116 and fluid accelerator 2115. Fluid accelerator intake 2118 is configured to supply a flow of matter received at nozzle 2114 to fluid accelerator 2115. Fluid accelerator intake 2118 includes a plurality of conical cavities having variable dimensions. The conical cavities each include a wide distal end and a narrow proximal end. In some embodiments, the conical cavities may be configured to take advantage of the Venturi effect. Fluid accelerator intake 2118 is configured to couple fluid accelerator 2115. Fluid accelerator intake 2118 may include geometry comprising a tapered-section disposed at the proximal end. The tapered-section of fluid accelerator intake 2118 may be configured, in combination with flow controller 2120, to form conduit 2129. The geometry of the tapered-section disposed at the proximal end of fluid accelerator intake 2118 may be configured to supply positive pressure supply 2121 to fluid accelerator 2115 at an angle in relation to an interior wall of fluid accelerator 2115.

Fluid accelerator 2115 includes fluid accelerator housing 2119. Fluid accelerator housing 2119 is disposed near the proximal end of suction device with backflow prevention valve 2100. Fluid accelerator housing 2119 is configured to couple to pressurized gas port 2111 and flow controller 2120. Fluid accelerator housing 2119 may include threads configured to couple to flow controller 2120. The threads may be configured to translate rotational motion of flow controller 2120 to a linear motion that adjusts a dimension of conduit 2129. Fluid accelerator housing 2119 includes a generally cylindrical cavity having a first opening at a first end and a second opening at a second end. The cylindrical cavity is defined by the inner wall of fluid accelerator housing 2119. Fluid accelerator housing 2119 includes a conduit 2129 in the inner wall near the first end. Conduit 2129 may be configured to supply positive pressure supply 2121 at an angle in relation to the inner wall of fluid accelerator 2115.

Fluid accelerator 2115 includes flow controller 2120. Flow controller includes pressurized waste port/outlet port 2113. Flow controller 2120 is configured to couple to fluid accelerator housing 2119. Flow controller 2120 includes pressurized waste port 1913. Flow controller 2120 may include a flared element disposed at the distal end of flow controller 2120. The flared element may be configured, in combination with fluid accelerator intake 2118, to supply positive pressure at an angle in relation to an interior wall of fluid accelerator 2115. Flow controller is rotatable to adjust conduit 2129. Conduit 2129 is adjustable to control a pressure difference between ambient air and the low pressure region at the nozzle 2114. The dimension of conduit 2129 can be adjustable to control a ratio of gas suction to liquid suction to solid suction provided by fluid accelerator 2115. Conduit 2129 has a profile such that the pressurized gas entering the cavity attaches to a curved surface of the portion of the structure defining conduit 2129, thereby creating the low pressure region which increases the overall mass flow rate of the accelerated flow. Flow controller 2120 may include O-rings to provide a seal between flow controller 2120 and fluid accelerator housing 2119.

Flow controller 2120 includes pressurized waste port/outlet port 2113. Pressurized waste port/outlet port 2113 is disposed at the distal end of flow controller 2120. Pressurized waste port/outlet port 2113 is configured to direct positive pressure effluent 2123 a waste repository. The waste repository may include a collection canister, waste drain, tubing or piping configured to carry away positive pressure effluent. In some embodiments, pressurized waste port/outlet port 2113 may include fittings for coupling to tubing. Some types of fittings that may be used include barbed, quick-disconnect, or compression fittings. In the embodiment illustrated in FIG. 21A, pressurized waste port/outlet port 2113 includes O-rings for coupling pressurized waste port/outlet port 2113 to tubing.

Fluid accelerator 2115 includes conduit 2129. Annular opening is disposed between fluid accelerator intake 2118 and fluid accelerator housing 2119. Conduit 2129 defines a jet opening adapted to allow positive pressure supply 2121 to flow through conduit 2129 such that a low pressure region is produced near nozzle 2114. Conduit 2129 is configured to receive positive pressure supply 2121 from pressurized gas port 2111 and supply it to fluid accelerator 2115. The proximal end of fluid accelerator intake 2118 and the distal end of flow controller 2120 may be configured to form conduit 2129. Conduit 2129 may be configured such that positive pressure supply 2121 enters fluid accelerator 2115 at an angle (e.g., 0°-90°) with respect to the inner wall of the cylindrical cavity. In some embodiments, a more acute angle (e.g., 30°-50°) may be desirable.

Suction device with backflow prevention valve 2100 includes backflow prevention valve 2116. Backflow prevention valve 2116 includes backflow prevention valve body 2180 and diaphragm 2185. Backflow prevention valve 2116 resides along the airflow path inside suction device with backflow prevention valve 2100. During normal operation, backflow prevention valve 2116 is configured to block exhaust ports 2181 to provide maximum suction near nozzle 2114. Backflow prevention valve 2116 can stop the operation of fluid accelerator 2115 by cutting off positive pressure supply 2121 to one or more components of fluid accelerator 2115 that cause a low pressure region to be created. Backflow prevention valve 2116 is configured to stop any 'reverse' flow of matter from exiting via suction assembly 2112 or nozzle 2114. Backflow prevention valve 2116 may be configured such that, once activated, it will stay activated thereby preventing any flow out of suction assembly 2112 or nozzle 1214 until positive pressure gas supply is removed (i.e., turned off), or a blockage is cleared.

Backflow prevention valve 2114 may be configured to divert at least positive pressure supply 2121 out exhaust ports 2181 when activated to prevent positive pressure supply 2121 from increasing beyond a desired limit within suction device with backflow prevention valve 2100. In this example, exhaust ports 2181 are integral to suction assembly 2112. In the event of an obstruction or blockage within a portion of suction device with backflow prevention valve 2100, backflow prevention valve 2116 is configured to move within suction assembly 2112 to open exhaust ports 2181. Opening exhaust ports 2181 allows positive pressure gas 2121 to escape from suction device with backflow prevention valve 2100.

Backflow prevention valve 2116 includes diaphragm 2185. Diaphragm 2185 is comprised of a flexible material. Diaphragm 2185 is configured to flex in response to a flow. Diaphragm 2185 is configured to permit a flow in a first direction through backflow prevention valve 2116 during normal operation by flexing in the direction of a flow. Diaphragm 2185 is configured to prevent positive pressure supply 2121 from passing through backflow prevention valve body 2180 in a second direction. Backflow prevention valve body 2180 includes structural elements configured to limit the flexure of diaphragm 2185 in a second direction. Backflow prevention valve 2116 is configured to activate in the event that suction device with backflow prevention valve 2100 or a portion thereof becomes obstruction or blocked. When activated, positive pressure supply 2121 causes diaphragm 2185 to flex until the flexure is limited by backflow prevention valve body 2180. When the flexure of diaphragm 2185 is limited by backflow prevention valve body 2180, positive pressure supply 2121 applies force to diaphragm 2185. Diaphragm 2185 transfers the force form positive pressure supply 2121 to backflow prevention valve 2116, thereby causing backflow prevention valve body 2180 to slide within suction assembly 2112. When backflow prevention valve body 2180 is activated, at least the flow of positive pressure supply 2121 is prevented from exiting at suction assembly 2112 or nozzle 2114. Diaphragm 2185 may be configured to directed positive pressure supply through exhaust ports 2181 when backflow prevention valve 2116 is activated.

FIG. 21B1 illustrates the central axis 2126 of the device, from which the angle 2128 is measured. The inlet port 2117 is located on one end of the fluid accelerator 2115 and the outlet port 2113 is located on an opposite end. The low pressure chamber 2127 is an internal volume of the fluid accelerator 2115 where the flow of matter/suction flow 2124 is generated.

FIGS. 21B and 21C are close-up diagrams illustrating conduit 2129 of a suction device with backflow prevention valve 2100. First hollow segment 2122, fluid accelerator housing 2119 and second hollow segment 2125 are configured to form conduit 2129. First hollow segment 2122 may comprise a first opening 2133 that may be adjacent to a second opening 2134 of the second hollow segment 2125. A first facing surface 2130 may at least partially surround the first opening 2133. A second facing surface 2132 may at least partially surround the second opening 2134. The first facing surface 2130 may face the second facing surface 2132. The first facing surface 2130 or the second facing surface 2132 may be beveled, flared, angled, or any combination thereof. Conduit 2129 includes pressure gap 2131. Pressure gap 2131 is configured to be adjustable. Adjusting the dimensions of pressure gap 2131 adjusts the flow rate of positive pressure supply 2121 through conduit 2129. Adjusting the flow rate of positive pressure supply 2121 through conduit 2129 adjusts a pressure difference between a low pressure region generated near nozzle 2114 and an ambient air pressure, thereby adjusting flow through suction device with backflow prevention 2100. Pressure gap 2131 is adjustable to control a ratio of gas suction to liquid suction to solid suction provided by fluid accelerator 2115. Adjusting the fluid flow allows the user to tune suction device with backflow prevention valve 2100 to intake desired ratios of gas (e.g., smoke), liquids and solids, or a combination of all three. Conduit 2129 may be configured such that positive pressure supply 2121 enters fluid accelerator 2115 at an angle (e.g., 0°-90°) with respect to an inner wall of fluid accelerator 2115. In some embodiments, a more acute angle (e.g., 30°-50°) may be desirable.

Conduit 2129 is partially comprised of first hollow segment 2122. The proximal end of first hollow segment 2122 and the distal end of second hollow segment 2125 define a jet opening adapted to allow positive pressure supply 2121 to flow through conduit 2129. The proximal end of first hollow segment 2122 may include geometry configured to direct the flow of positive pressure supply 2121.

Conduit 2129 is partially comprised of fluid accelerator housing 2119. Fluid accelerator housing 2119 is coupled to pressurized gas port 2111. Fluid accelerator housing is configured to receive positive pressure supply 2121 and supply it to conduit 2129. Fluid accelerator housing 2119 may include threads configured to couple to second hollow segment 2125. The threads allow pressure gap 2131 to be adjusted by rotating second hollow segment 2125. Second hollow segment 2125 may be configured to translate rotational motion into linear motion to adjust pressure gap 2131.

Conduit 2129 is partially comprised of second hollow segment 2125. The distal end of second hollow segment 2125 may be flared to direct positive pressure supply 2121 to enter fluid accelerator at an angle in relation to an interior wall of fluid accelerator 2115. Second hollow segment 2125 may include threads configured to mate with fluid accelerator housing 2119. The threads may be configured to translate rotational motion of second hollow segment 2125 to a linear motion that adjusts pressure gap 2131. Adjustment of pressure gap 2131 adjusts a difference between a low pressure region generated near nozzle 2114 and an ambient air pressure.

FIG. 21B is a diagram illustrating conduit 2129. As illustrated in FIG. 21B, pressure gap 2131 is adjusted to allow an increased flow of positive pressure supply 2121 through conduit 2129 with respect to pressure gap 2131 as illustrated in FIG. 21C. Pressure gap 2131 as illustrated in FIG. 21B generates a larger difference between a low pressure region generated near nozzle 2114 and an ambient air pressure thereby generating more flow through suction device with backflow prevention valve 2100 than pressure gap 2131 as illustrated in FIG. 21C.

Conduit 2129 includes angle 2128 relative to the central axis 2126. Angle 2128 relative to the central axis 2126 is configured to supply pressure received from pressurized gas port 2111 at an angle with respect to fluid accelerator 2115. In some embodiments, angle 2128 relative to the central axis 2126 may be configured to take advantage of the Coanda effect to generate suction. In some embodiments, angle 2128 relative to the central axis 2126 may be an acute angle (e.g., 0°-90°). In some embodiments, angle 2128 relative to the central axis 2126 may be between 30°-60°. In some embodiments, angle 2128 relative to the central axis 2126 may be 55°.

FIG. 21C is a diagram illustrating conduit 2129. As illustrated in FIG. 21C, pressure gap 2131 is adjusted to allow a decreased flow of positive pressure supply 2121 through conduit 2129 with respect to pressure gap 2131 as illustrated in FIG. 21B. Pressure gap 2131 as illustrated in FIG. 21C generates a smaller difference between a low pressure region generated near nozzle 2114 and an ambient air pressure thereby generating less flow through suction device with backflow prevention valve 2100 than pressure gap 2131 as illustrated in FIG. 21B.

Figure 21D:
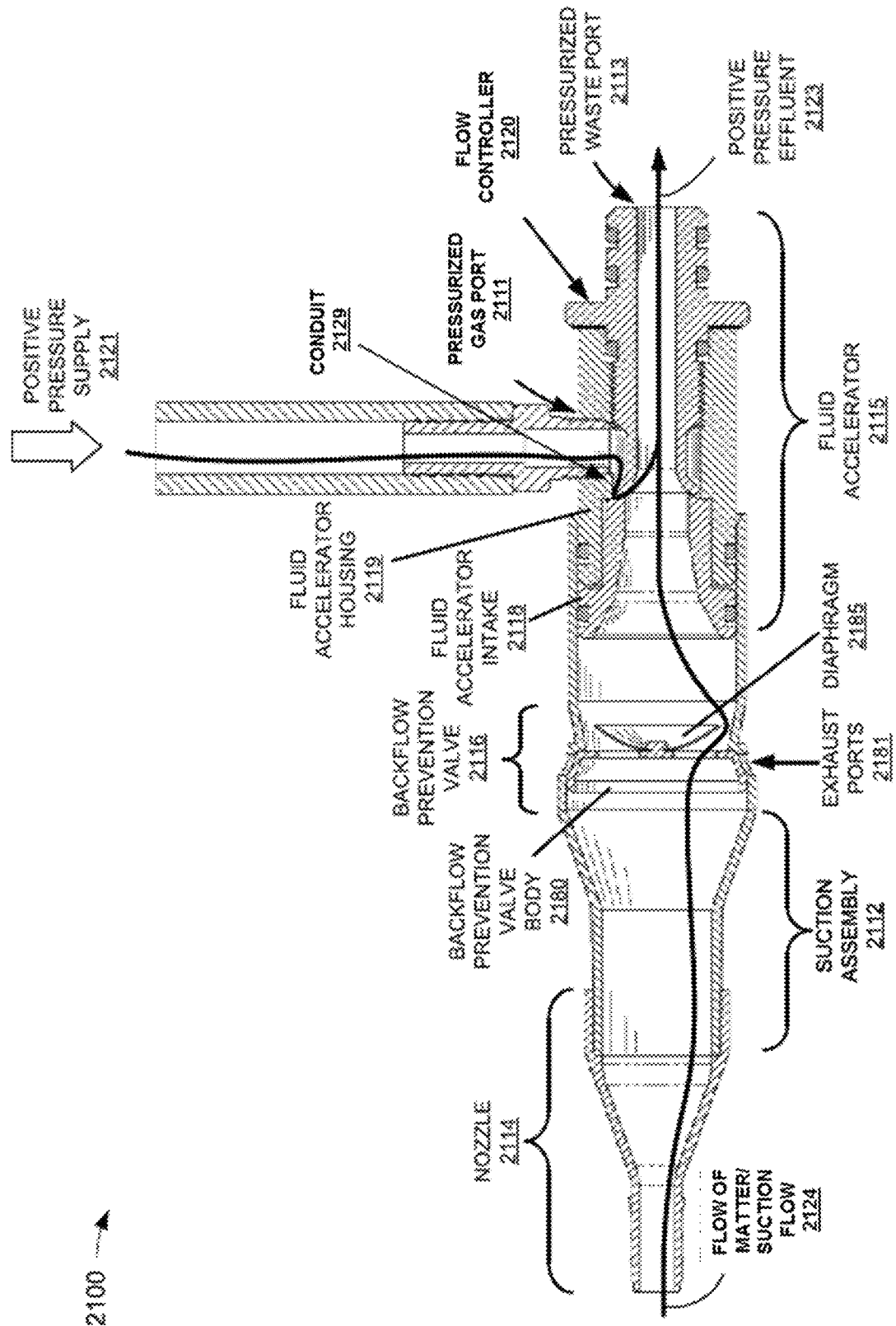
FIG. 21D is a diagram illustrating the operation of a suction device with backflow prevention valve during normal operation.

FIG. 21D is a diagram illustrating the operation of suction device with backflow prevention valve 2100 during normal operation. Backflow prevention valve 2116 is configured to move in proximal and distal directions within suction assembly 2112. During normal operation, backflow prevention valve 2116 slides to a proximal position within suction assembly 2112 blocking exhaust ports 2181 and allowing flow through suction device with backflow prevention valve 2100. In the event of a blockage, backflow prevention valve 2116 slides to a distal position within suction assembly 2112 to prevent backflow through suction assembly 2112 or nozzle 2114. In the distal position, backflow prevention valve opens exhaust ports 2181 to exhaust at least positive pressure supply 2121.

In operation, positive pressure supply 2121 is introduced to pressurized gas port 2111. Pressurized gas port 2111 supplies positive pressure supply 2121 through conduit 2129 to fluid accelerator 2115. The amount of flow through conduit 2129 is controlled by adjusting flow controller 2120. Portions of suction device with backflow prevention valve 2100, particularly in fluid accelerator 2115, create a low pressure region near nozzle 2114 to entrain and induce flow of matter/suction flow 2124 through suction device with backflow prevention valve 2100.

In operation, fluid accelerator 2115 receives positive pressure supply 2121 at pressurized gas port 2111 and directs positive pressure supply 2121 to fluid accelerator 2115 thereby generating a low pressure region at nozzle 2114. The low pressure region at nozzle 2114 has a pressure below ambient air pressure. The ambient air pressure overcomes the pressure in the low pressure region thereby creating suction at nozzle 2114. A low pressure region generated near nozzle 2114 pulls flow of matter/suction flow 2124 into suction assembly 2112. Flow of matter/suction flow 2124 can include liquids, gasses, and solids. Flow of matter/suction flow pulled 2124 is propelled by fluid accelerator 2115 out pressurized waste port/outlet port 2113 as positive pressure effluent 2123. Positive pressure effluent 2123 can include a combined flow of positive pressure supply 2121 and flow of matter/suction flow 2124.

Figure 21E:
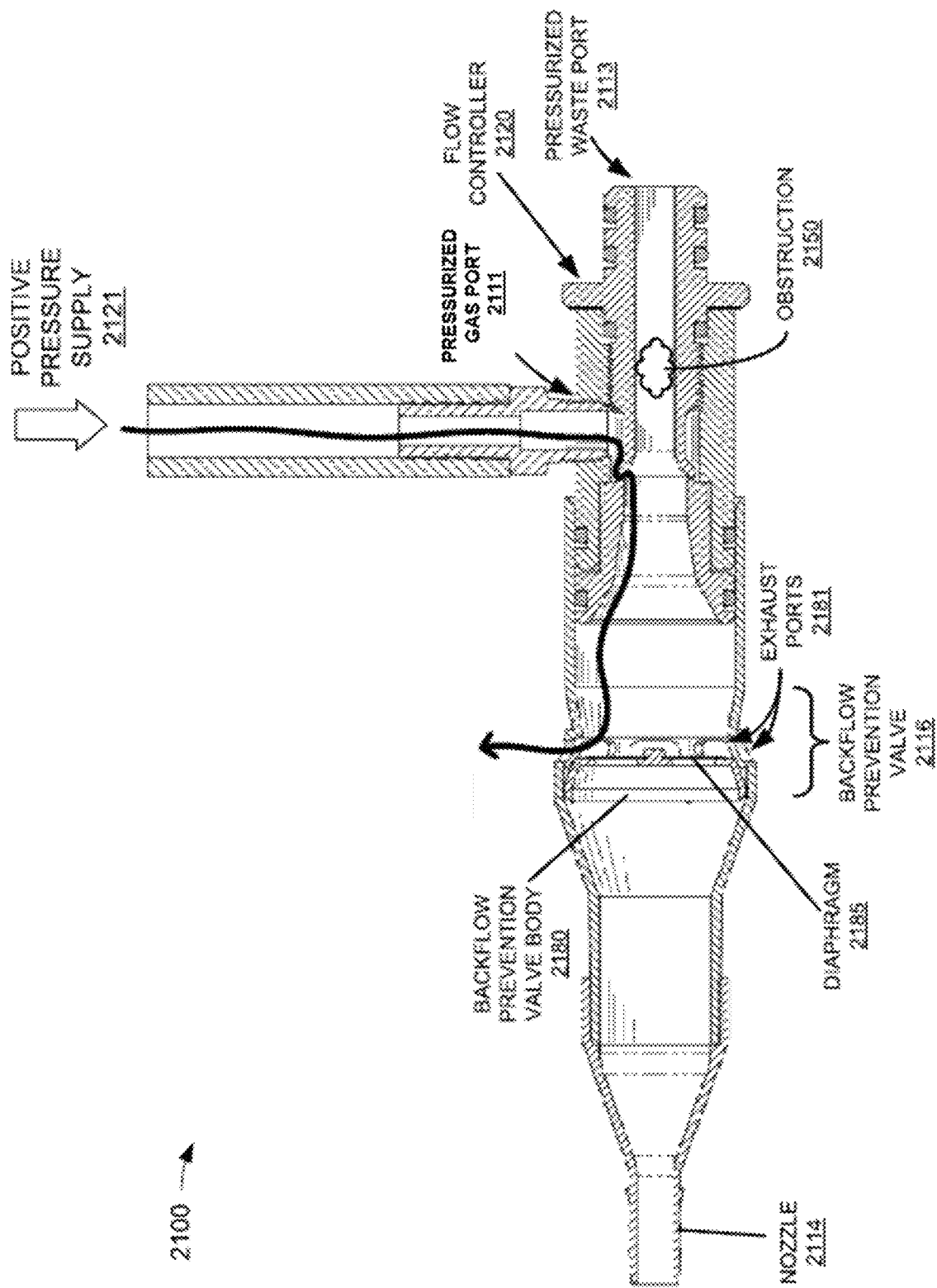
FIG. 21E is a diagram illustrating the operation of a suction device with backflow prevention valve in the event of an obstruction.

FIG. 21E is a diagram illustrating the operation of suction device with backflow prevention valve 2100 in the event of an obstruction. As illustrated in FIG. 21E, pressurized waste port/outlet port 2113 is blocked by obstruction 2150. Obstruction 2150 can prevent all or a substantial portion of positive pressure supply 2121 from flowing out pressurized waste port/outlet port 2113. Without backflow prevention valve 2116, when positive pressure supply 2121 (or a combination of positive pressure supply 2121 and positive pressure effluent 2123) cannot flow out of pressurized waste port/outlet port 2113, the positive pressure supply 2121 and possibly positive pressure effluent 2123 may instead be ejected out nozzle 2114. The ejection of an effluent (and of positive pressure supply 2121, in particular) is undesirable and can cause damage or other problems to items in the vicinity of nozzle 2114 (e.g., a patient). However, backflow prevention valve 2116 is configured to at least stop the flow of positive pressure supply 2121 and positive pressure effluent 2123 from exiting via nozzle 2114.

Backflow prevention valve 2116 can stop the operation of suction device with backflow prevention valve 2100 by preventing any 'reverse' flow of matter from exiting via nozzle 2114. Backflow prevention valve 2116 includes backflow prevention valve body 2180, exhaust ports 2181 and diaphragm 2185. Backflow prevention valve 2116 can activate when matter starts to flow in a manner that the flow would exit nozzle 2114. Backflow prevention valve 2116 may be configured such that, once activated, it will stay activated thereby preventing any flow out of nozzle 2114 until positive pressure supply 2121 is removed (i.e., turned off), or obstruction 2150 is cleared.

FIG. 21E is a diagram illustrating the operation of suction device with backflow prevention 2100 in the event of an obstruction. Obstruction 2150 prevents positive pressure supply 2121 from exiting pressurized waste port/outlet port 2113. Since positive pressure supply 2121 cannot exit pressurized waste port/outlet port 2113 due to obstruction 2150, the flow of positive pressure supply 2121 reverses direction towards nozzle 2114. Positive pressure supply 2121 forces diaphragm 2185 to flex against backflow prevention valve body 2180. Pressure is transferred from diaphragm 2185 to backflow prevention valve 2116 causing backflow prevention valve 2116 to slide within suction assembly 2112. When activated, backflow prevention valve 2116 may open exhaust ports 2181 allowing positive pressure supply 2121 to exhaust through exhaust ports 2181.

FIG. 22A is a diagram illustrating an exploded view of backflow prevention valve 2200. Backflow prevention valve 2220 is an example of backflow preventer 316, backflow preventer 516, backflow preventer 716, backflow preventer 816, backflow prevention valve 1316, backflow prevention valve 1516, backflow valve 1616, check valve 1716, valve 1916, and backflow prevention valve 2116; however, backflow prevention valve 2200 may include alternative configurations or methods of operation. Backflow prevention valve 2200 includes sliding body 2280 and diaphragm 2285.

Backflow prevention valve 2200 includes sliding body 2280. Sliding body 2280 includes alignment features 2282, male coupling 2283, apertures 2286 and support elements 2288. Sliding body 2280 is configured to reside within a housing, for example suction assembly 2112. Sliding body 2280 includes alignment features 2282. Alignment features 2282 comprise inclusions in sliding body 2280. Alignment features may be configured to interface with alignment features included in a housing to prevent backflow prevention valve 2200 from rotating. Sliding body 2280 includes support elements 2288. Support elements 2288 are configured to provide structural support to diaphragm 2285. Diaphragm 2285 is comprised of a flexible material. Support elements 2288 are configured to limit the amount of flexure of diaphragm 2285 in one direction. Pressure from a positive pressure source may be transferred from diaphragm 2285 to sliding body 2280 by support elements 2288. Male coupling is configured to couple sliding body 2280 to diaphragm 2285. As illustrated in FIG. 22A, male coupling 2283 is configured to couple to female coupling 2284 using a snap-fit. In some embodiments, male coupling 2283 may be a mechanical fastener (e.g., screw, bolt, rivet, etc.), a point where adhesive is applied, or other means of coupling male coupling 2283 to female coupling 2284. Sliding body 2280 includes apertures 2286. Apertures 2286 are configured to allow a flow of matter through sliding body 2280.

Backflow prevention valve 2200 includes diaphragm 2285. Diaphragm 2285 is configured to block a flow through apertures 2286 in one direction, while allowing a flow in the opposite direction. Diaphragm 2285 is comprised of a flexible material. Diaphragm 2285 is configured to flex in response to pressure. When a pressure flow is traveling in one direction, diaphragm 2285 is configured to flex allowing a flow to pass through apertures 2286. When a pressure flow is traveling in an opposite direction, diaphragm 2285 is configured to flex until the flexure is limited by support elements 2288. Diaphragm 2285 is configured to transfer pressure from pressure source to sliding body 2280. This transfer of pressure causes sliding body 2280 to move within a housing. Diaphragm 2285 includes female coupling 2284. Female coupling 2284 is configured to couple diaphragm 2285 to sliding body 2280. As illustrated in FIG. 22A, female coupling 2284 is configured to couple to male coupling 2283 using a snap-fit. In some embodiments, female coupling 2284 may be a hole to for a mechanical fastener (e.g., screw, bolt, rivet, etc.), a point where adhesive is applied, or some other means of coupling female coupling 2284 to male coupling 2283.

FIG. 22B is a diagram illustrating backflow prevention valve 2200 during a blockage. In the event of a blockage, pressure from a pressure source causes diaphragm 2285 to flex. Flexure of diaphragm 2285 is limited by support elements 2288. As illustrated in FIG. 22B, diaphragm 2285 is resting upon support elements 2288. In this mode of operation, diaphragm 2285 is able to transfer pressure from a pressure source to sliding body 2280. This transfer of pressure can cause backflow prevention valve 2200 to activate.

FIG. 22C is a diagram illustrating backflow prevention valve 2200 during normal operation. During normal operation, pressure from a pressure source causes diaphragm 2285 to flex thereby allowing a flow through apertures 2286. Pressure from a pressure source may act on diaphragm 2285. Pressure may be transferred from diaphragm 2285 to sliding body 2280 by male coupling 2283 and female coupling 2284. During normal operation, pressure from a pressure source may act on diaphragm 2285 thereby causing backflow prevention valve 2200 to slide within a housing. When deactivate, backflow prevention valve 220 may be configured to block exhaust ports.

Figure 23A:
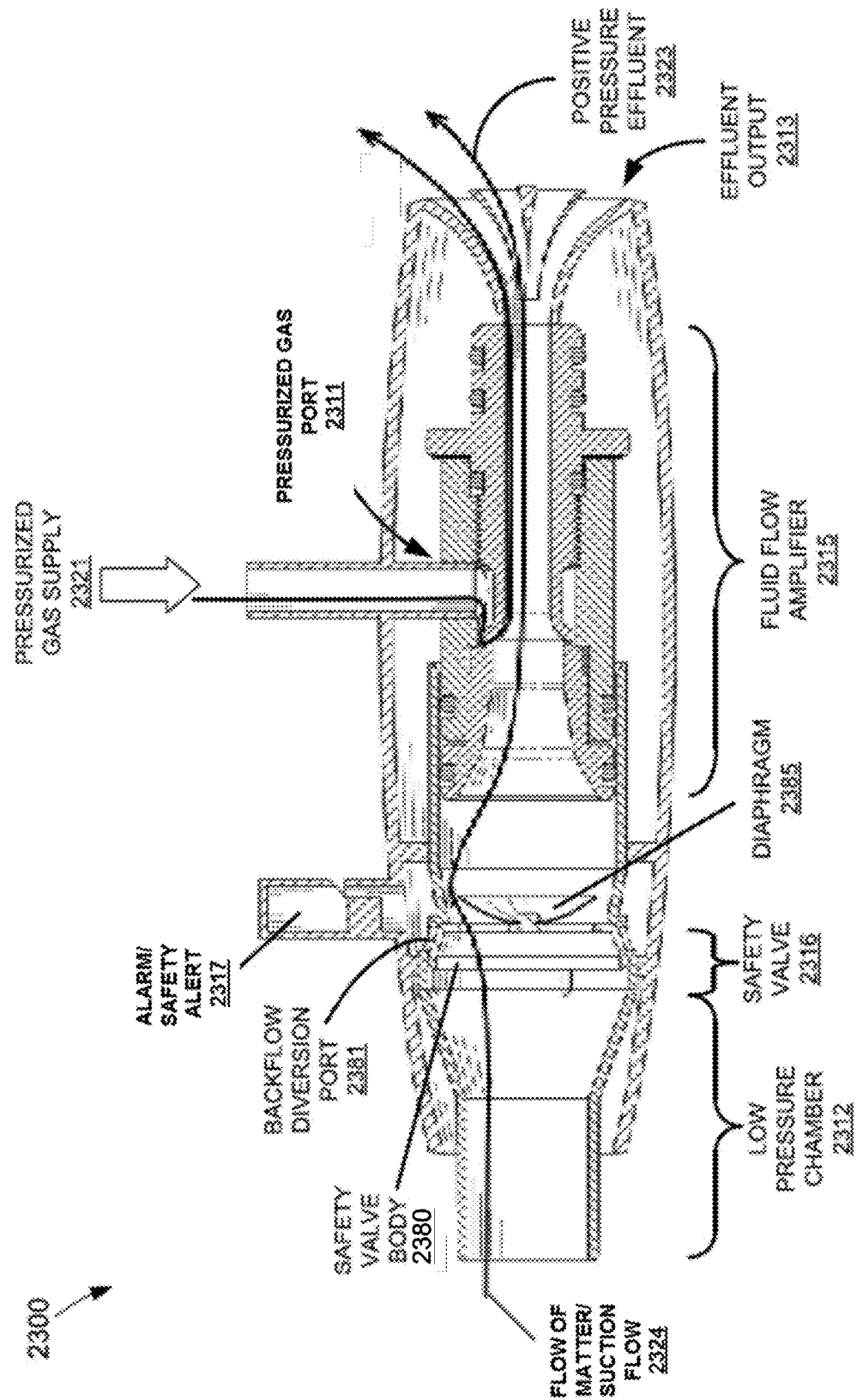
FIG. 23A is a diagram illustrating the operation of a positive pressure vacuum device with safety features during normal operation.

FIG. 23A is a diagram illustrating the operation of positive pressure vacuum device with safety features 2300 during normal operation. Positive pressure vacuum device with safety features 2300 is an example of suction system 100, suction system with backflow prevention 300, suction system with backflow alert 400, suction system with safety features 500, positive pressure operated suction device 1200, positive pressure operated suction device with backflow prevention 1300, positive pressure operated suction device with backflow alert 1400, and positive pressure operated suction device with safety features 1500; however, positive pressure operated vacuum device with safety features 2300 may include alternative configurations and methods of operation. Positive pressure vacuum device with safety features 2300 includes pressurized gas port (such as a positive pressure input port) 2311, low pressure chamber 2312, effluent output 2313, fluid flow amplifier 2315, safety valve 2316, safety valve body 2380, and alarm/safety alert 2317.

In operation, fluid flow amplifier 2315 receives pressurized gas supply 2321 to generate a low pressure region near low pressure chamber 2312. Fluid flow amplifier 2315 may be configured to take advantage of the Coanda effect to generate a low pressure region near low pressure chamber 2312. The low pressure region draws safety valve 2316 proximally within low pressure chamber 2312, blocking backflow diversion ports 2381 and opening diaphragm 2385. During normal operation, backflow prevention valve 2116 blocks backflow diversion ports 2381 to provide maximum suction near low pressure chamber 2312. The low pressure region pulls flow of matter/suction flow 2324 into low pressure chamber 2312. Flow of matter/suction flow 2324 can include liquids, gasses, and solids. Low pressure chamber 2127 directs flow of matter/suction flow 2324 to fluid flow amplifier 2315. Fluid flow amplifier 2315 is configured to generate a laminar flow. Flow of matter/suction flow 2324 may be entrained with pressurized gas supply 2321 within fluid flow amplifier 2315 and ejected as positive pressure effluent 2323 out effluent output 2313. The laminar flow within fluid flow amplifier 2315 allows positive pressure gas supply 2321 to be separated from flow of matter/suction flow 2324 by effluent output 2313. Effluent output 2313 may be configured to eject pressurized gas supply 2321 and positive pressure effluent 2323 as separate streams. Effluent output 2313 may be configured to couple to tubes, pipes, etc. for collection, further separation, and/or disposal of pressurized gas supply 2321 and positive pressure effluent 2323.

Figure 23B:
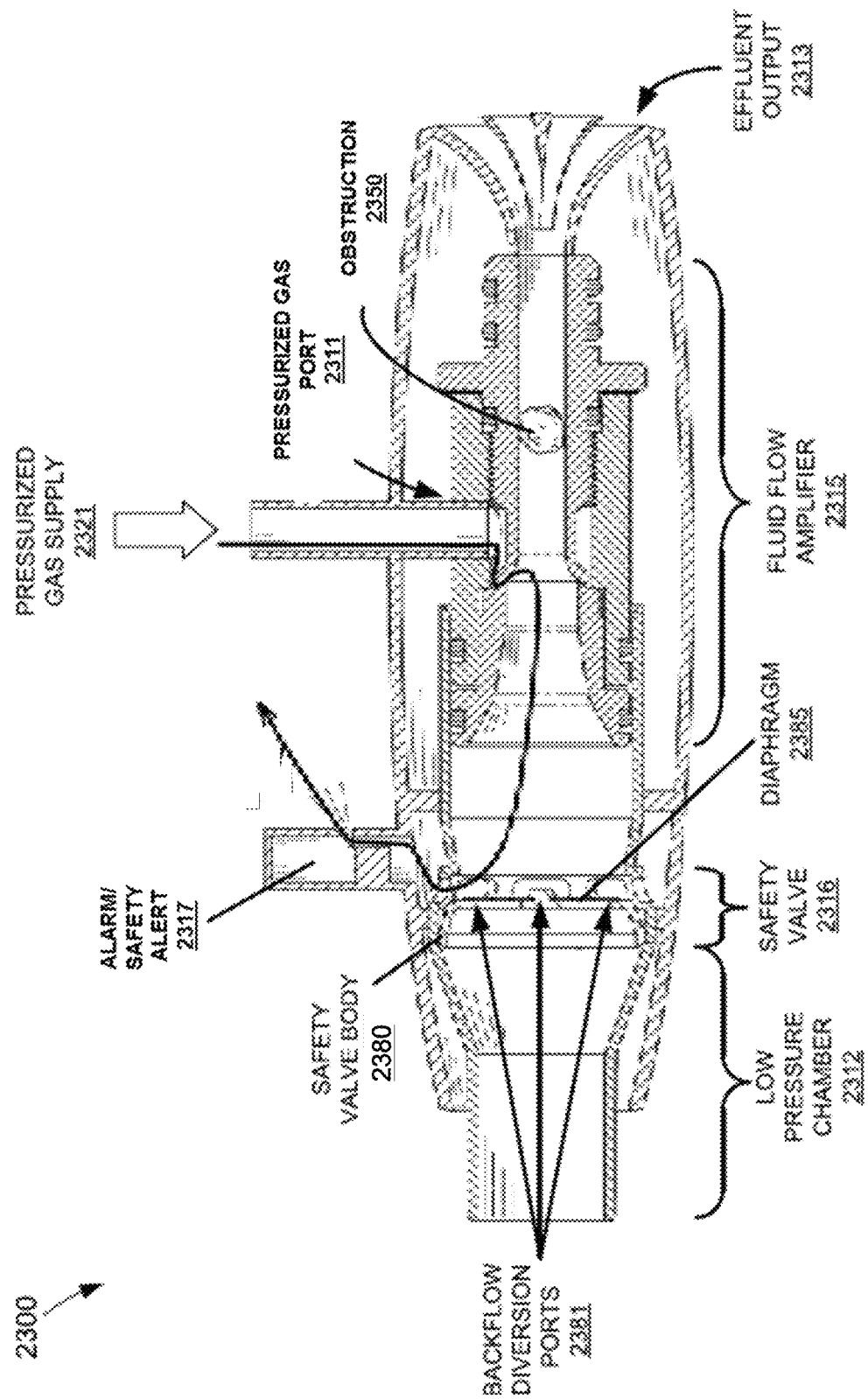
FIG. 23B is a diagram illustrating the operation of a positive pressure suction device with safety features in the event of a blockage.

FIG. 23B is a diagram illustrating the operation of positive pressure suction device with safety features 2300 in the event of a blockage. Flow through positive pressure suction device with safety feature 2300 is blocked by obstruction 2350. Obstruction 2350 can prevent all or a substantial portion of pressurized gas supply 2321 from flowing out of effluent output 2313. When pressurized gas supply 2321 is prevented from exhausting at effluent output 2313, pressurized gas supply 2321 may be forced to exit out low pressure chamber 2312. Without backflow safety valve 2316 pressurized gas supply 2321 and possibly flow of matter/suction flow 2324 may be ejected out of low pressure chamber 2312. The ejection pressurized gas supply 2321 and flow of matter/suction flow 2324 is undesirable and can cause damage or other problems to items in the vicinity of low pressure chamber 2312 (e.g., a patient). However, safety valve 2316, along with safety valve body 2380, is configured to at least stop the flow of pressurized gas supply 2321 from exiting via low pressure chamber 2312.

FIG. 23B illustrates obstruction 2350 preventing pressurized gas supply 2321 from exiting effluent output 2313. Since pressurized gas supply 2321 cannot exit effluent output 2313 due to obstruction 2350, the flow of pressurized gas supply 2321 reverses direction towards low pressure chamber 2312. Pressurized gas supply 2321 forces diaphragm 2385 to close and safety valve 2316 to slide within low pressure chamber 2312. Once activated, safety valve 2316 may open backflow diversion ports 2381 to allow pressurized gas supply 2321 to escape thereby preventing pressure from increasing beyond a desirable limit within positive pressure suction device with safety features 2300.

Backflow diversion ports 2381 are operatively coupled to alarm/safety alert 2317. Backflow diversion ports 2381 may be configured to direct pressurized gas supply 2321 to alarm/safety alert 2317 when safety valve 2316 is activated. In this example, alarm/safety alert 2317 is configured to produce an audible alert using pressurized gas supply 2321.

Figure 24A:
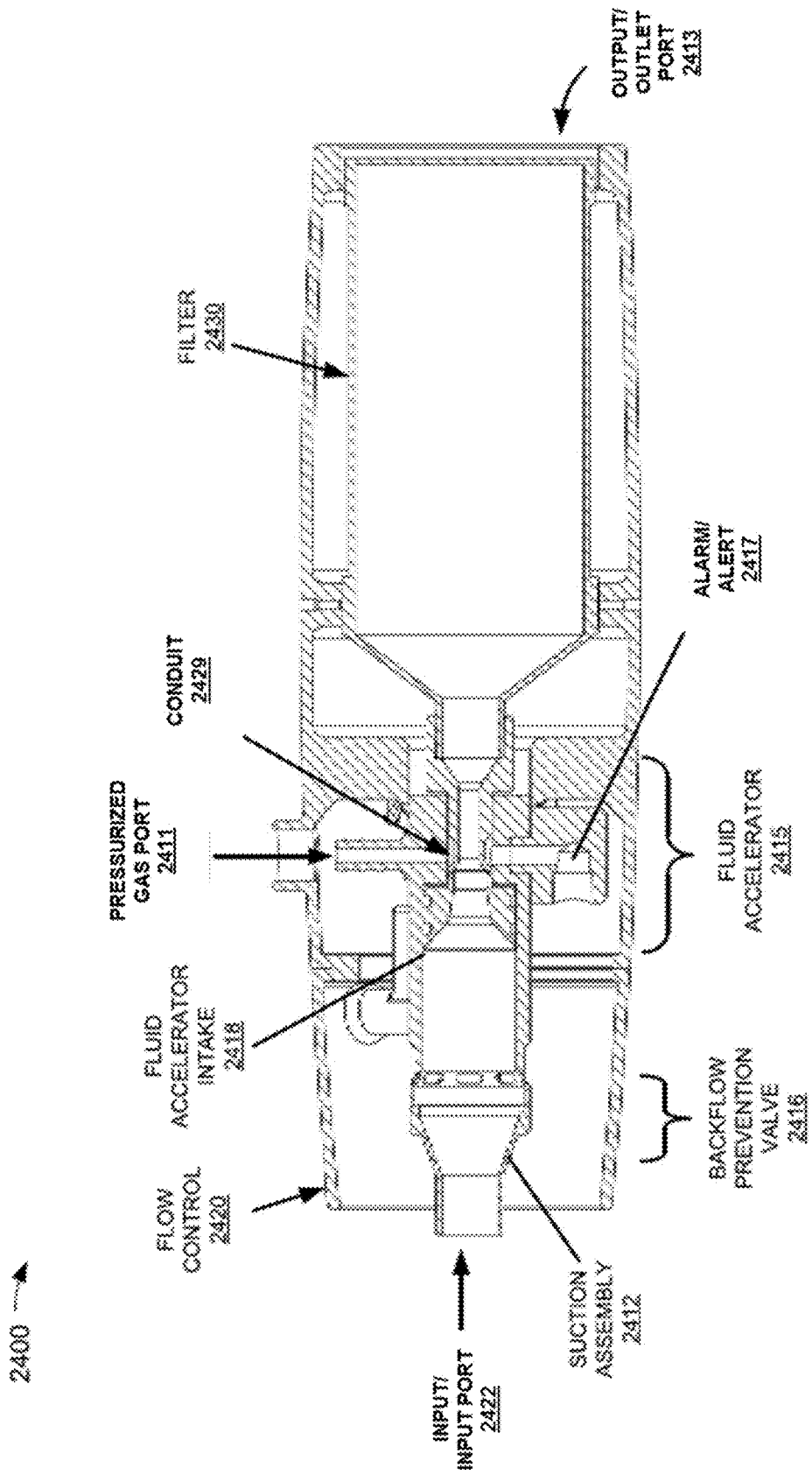
FIG. 24A is a diagram illustrating a positive pressure operated suction device.

FIG. 24A is a diagram illustrating positive pressure operated suction device 2400. Positive pressure operated suction device 2400 is an example of suction system 100, suction system with backflow prevention 300, suction system with backflow alert 400, suction system with safety features 500, filtering suction system 1000, positive pressure operated suction device 1200, positive pressure operated suction device with backflow alert 1400, positive pressure operated suction device with safety features 1500, filtering suction device with safety features 1600, and suction device with adjustable pressure gap 1900; however, positive pressure operated suction device 2400 may include alternative configurations and methods of operation. Positive pressure operated suction device 2400 includes pressurized gas port (such as a positive pressure intake) 2411, suction assembly 2412, output/outlet port 2413, fluid accelerator 2415, backflow prevention valve 2416, alarm/alert 2417, fluid accelerator intake 2418, flow control 2420, input/input port 2422, conduit (such as an annular opening) 2429 and filter 2430.

Pressurized gas port 2411 is configured to receive positive pressure from a positive pressure source. The positive pressure source is configured to provide gas at a pressure above an ambient air pressure. The positive pressure source may include compressed gas from a compressor, gas from a high-pressure gas cylinder, or even a human breath. Pressurized gas port 2411 is configured to supply positive pressure to fluid accelerator 2415 via conduit 2429.

Suction assembly 2412 is disposed towards the distal end of positive pressure operated suction device 2400. Suction assembly 2412 includes input/input port 2422. Suction assembly 2412 is configured to receive a flow of matter. Suction assembly 2412 is configured to house backflow prevention valve 2416.

Fluid accelerator 2415 is configured to generate a low pressure region within suction assembly 2412 and near input/input port 2422. The low pressure region generated by fluid accelerator 2415 is below an ambient air pressure. The low pressure region causes an ambient air pressure to push a flow of matter into input/input port 2422 and through suction assembly 2412. The flow of matter may include liquids, solids, and gasses.

Output/outlet port 2413 is disposed towards the proximal end of positive pressure operated suction device 2400. Output/outlet port 2413 is configured to receive a filtrate from filter 2430. Output/outlet port 2413 may be configured to output the filtrate received from filter 2430 to a collection source. The collection source may include tubing, a canister, or a waste drain.

Fluid accelerator 2415 is configured to accelerate flow of matter/suction flow 2424 using positive pressure supply 2421. Fluid accelerator 2415 includes conduit 2429. Conduit 2429 is configured to direct positive pressure supply 2421 received from pressurize gas port 2411 at an angle in relation to an interior wall of fluid accelerator 2415. Fluid accelerator 2415 may be configured to take advantage of the Coanda effect to generate a low pressure region near input/input port 2422 from positive pressure supply 2421. Fluid accelerator 2415 is configured to generate positive pressure effluent 2423. Positive pressure effluent 2423 may include a combined flow of positive pressure supply 2421 and flow of matter/suction flow 2424. Fluid accelerator 2415 is configured to direct positive pressure effluent through filter 2430. Filter 2430 is configured to trap particles included in positive pressure effluent 2423 and pass positive pressure filtrate 2426 out output/outlet port 2413.

Backflow prevention valve 2416 is disposed between suction assembly 2412 and fluid accelerator 2415. Backflow prevention valve 2416 is configured to prevent at least positive pressure supply 2421 from exiting input/input port 2422.

Alarm/alert 2417 is configured to notify a user that flow through positive pressure operated suction device 2400 has become obstructed. Alarm/alert 2417 may be configured to operate in conjunction with backflow prevention valve 2416. Flow through suction assembly 2412 may be blocked upon activation of backflow prevention valve 2416. Backflow prevention valve 2416 may be configured to direct positive pressure supply 2421 through exhaust ports 2181 and to alarm/alert 2417. Alarm/alert 2417 may be configured to generate an alert from positive pressure supply 2421.

Fluid accelerator intake 2418 includes a plurality of conic sections each having a wide end and a narrow end. In some embodiments, fluid accelerator intake may be configured to take advantage of the Venturi effect to accelerate flow through fluid accelerator intake 2418. Fluid accelerator intake is configured to direct a flow of matter received at input/input port 2422 into fluid accelerator 2415.

Flow control 2420 is disposed toward the distal end of positive pressure operated suction device 2400. Flow control 2420 includes a rotatable member configured to receive a user input. Flow control translates rotational motion received from a user input into a linear motion that can adjust a pressure gap disposed between fluid accelerator intake 2418 and fluid accelerator 2415. In some embodiments, flow control 2420 may translate a larger movement from into a smaller movement near conduit 2429.

Conduit 2429 is disposed between fluid accelerator intake 2418 and fluid accelerator 2415. Conduit 2429 includes an adjustable pressure gap. The adjustable pressure gap controls the flow of pressure received from pressurized gas port 2411 through conduit 2429 and therefore the flow of pressure into fluid accelerator 2415. Conduit 2429 may be adjusted by a user by adjusting flow control 2420. The strength of the low pressure region may be adjusted by adjustment of conduit 2429.

Filter 2430 is disposed near the proximal end of positive pressure operated suction device 2400. Filter 2430 is configured to receive positive pressure effluent 2423. Filter 2430 is configured to trap particles and pass positive pressure filtrate 2426 to output/outlet port 2413.

FIG. 24B is a close-up diagram of FIG. 24B1, illustrating the operation of adjustable pressure gap 2431 for positive pressure operated suction device. Flow control 2420 includes adjustment feature, such as a tuner arm 2440. Tuner arm 2440 is configured to allow a user to control the low pressure region near input/input port 2422. In this embodiment, tuner arm 2440 permits a user to adjust adjustable pressure gap 2431 using one hand. Tuner arm 2440 is configured to receive a rotational input from a user. Tuner arm 2440 is configured to provide rotational motion to flow control 2420. Flow control 2420 is configured to provide rotational motion to motion translator 2442. Motion translator 2442 is configured to translate rotational motion received from flow control 2420 to a linear motion. The linear motion from motion translator 2442 is configured to adjust pressure gap 2431.

Conduit 2429 includes pressure gap 2431. Pressure gap 2431 is configured to be adjustable. Adjustment of pressure gap 2431 adjusts the flow rate of positive pressure supply 2421 through conduit 2429. Adjustment of positive pressure supply 2421 through conduit 2429 adjusts a pressure difference between a low pressure region generated near input/input port 2422 and an ambient air pressure. Pressure gap 2431 may be configured to control a ratio of gas suction to liquid suction to solid suction provided by a second hollow segment 2402, such as fluid accelerator 2415. Adjustment of positive pressure supply 2421 through conduit 2429 may allow a user to tune positive pressure operated suction device 2400 to intake desired ratios of gas (e.g., smoke), liquids and solids, or a combination of all three. Conduit 2429 may be configured such that positive pressure supply 2421 enters second hollow segment 2402 at an angle (e.g., 0°-90°) with respect to an inner wall of second hollow segment 2402. In some embodiments, a more acute angle (e.g., 30°-50°) may be desirable.

Conduit 2429 is partially comprised of a first hollow segment 2401, such as fluid accelerator intake 2418, and a second hollow segment 2402, such as fluid accelerator 2415. The proximal end of first hollow segment 2401 and the distal end of second hollow segment 2402 may be configured to define a jet opening adapted to allow positive pressure supply 2421 to flow through conduit 2429. The proximal end of first hollow segment 2401 may include geometry comprising conic sections configured to direct the flow of positive pressure supply 2421 into second hollow segment 2402 at an angle in relation to an interior wall of second hollow segment 2402.

First hollow segment 2401 may comprise a first opening 2405 that may be adjacent to a second opening 2406 of the second hollow segment 2402. A first facing surface 2403 may at least partially surround the first opening 2405. A second facing surface 2404 may at least partially surround the second opening 2406. The first facing surface 2403 may face the second facing surface 2404. The first facing surface 2403 or the second facing surface 2404 may be beveled, flared, angled, or any combination thereof.

Conduit 2429 is partially comprised of second hollow segment 2402. The distal end of second hollow segment 2402 may be flared to direct positive pressure supply 2421 to enter second hollow segment 2402 at an angle in relation to an interior wall of second hollow segment 2402.

As illustrated in FIG. 24B, pressure gap 2431 is adjusted to allow an increased flow of positive pressure supply 2421 through conduit 2429 with respect to pressure gap 2431 as illustrated in FIG. 24C. Pressure gap 2431 as illustrated in FIG. 24B generates a larger difference between a low pressure region generated near input/input port 2422 and an ambient air pressure thereby generating more flow through positive pressure operated suction device 2400 than pressure gap 2431 as illustrated in FIG. 24C.

FIG. 24C is a close-up diagram of FIG. 24C1, illustrating conduit 2429. As illustrated in FIG. 24C, pressure gap 2431 is adjusted to allow a decreased flow of positive pressure supply 2421 through conduit 2429 with respect to pressure gap 2431 as illustrated in FIG. 24B. Pressure gap 2431 as illustrated in FIG. 24C generates a smaller difference between a low pressure region generated near input/input port 2422 and an ambient air pressure thereby generating less flow through positive pressure operated suction device 2400 than pressure gap 2431 as illustrated in FIG. 24B. In some embodiments, adjustment of adjustable pressure gap 2431 can stop operation of positive pressure operated suction device 2400.

Figure 24D:
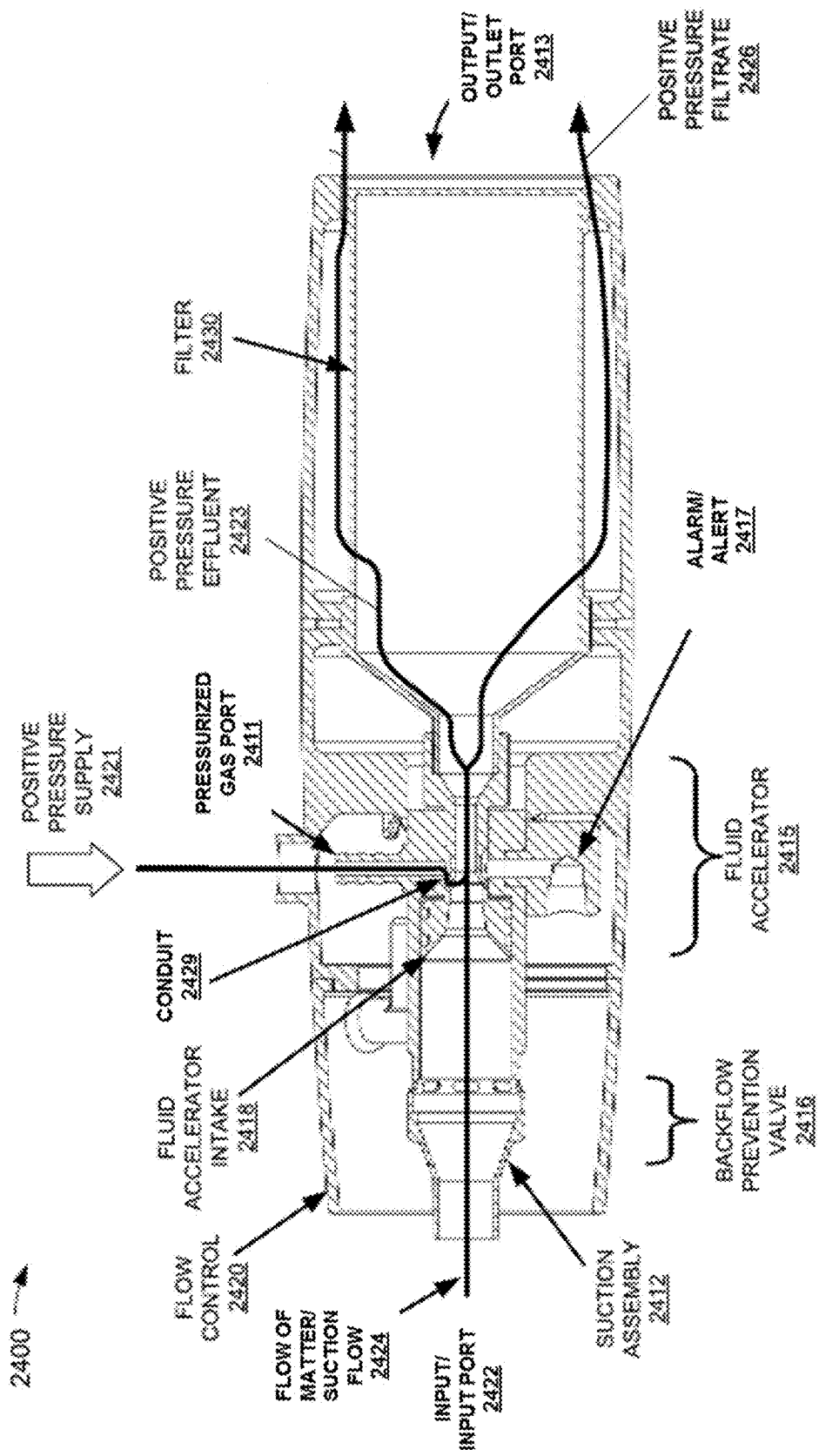
FIG. 24D is a diagram illustrating the operation of a positive pressure operated suction device during normal operation.

FIG. 24D is a diagram illustrating the operation of positive pressure operated suction device 2400 during normal operation. Backflow prevention valve 2416 includes backflow prevention valve body 2180 and exhaust ports 2181. Backflow prevention valve 2416 is configured to move within suction assembly 2412. During normal operation, backflow prevention valve 2416 may be configured to block exhaust ports 2181 and allow flow through positive pressure operated suction device 2400. In the event of a blockage, backflow prevention valve 2416 slides to within suction assembly 2412 to prevent at least positive pressure supply 2421 from exiting intake/input port 2422. Backflow prevention valve 2416 may be configured to open exhaust ports 2181 to prevent positive pressure supply 2421 from increasing beyond a desirable limit within positive pressure operated suction device 2400.

In operation, positive pressure supply 2421 is introduced to pressurize gas port 2411. Pressurized gas port 2411 supplies positive pressure supply 2421 to fluid accelerator 2415. Fluid accelerator 2415 may be configured to take advantage of the Coanda effect. Fluid accelerator 2415 is configured to generate a low pressure region near input/input port 2422 from positive pressure supply 2421. Conduit 2429 may be configured to supply positive pressure supply 2421 to fluid accelerator 2425 at an angle in relation to the interior wall of fluid accelerator 2415. Portions of positive pressure operated suction device 2400, particularly in fluid accelerator 2415, are configured to create a low pressure region in suction assembly 2412. This low pressure region may be used to entrain and induce flow of matter/suction flow 2424 through positive pressure operated suction device 2400.

FIG. 24D illustrates flow of matter/suction flow 2424 entering input/input port 2422. Flow of matter/suction flow 2424 may be entrained with positive pressure supply 2421 within fluid accelerator 2415. This combined flow is illustrated as positive pressure effluent 2423. Fluid accelerator 2415 pushes positive pressure effluent 2423 through filter 2430. Filter 2430 is configured to trap particles and pass positive pressure effluent 2426 out output/outlet port 2413.

Figure 25:
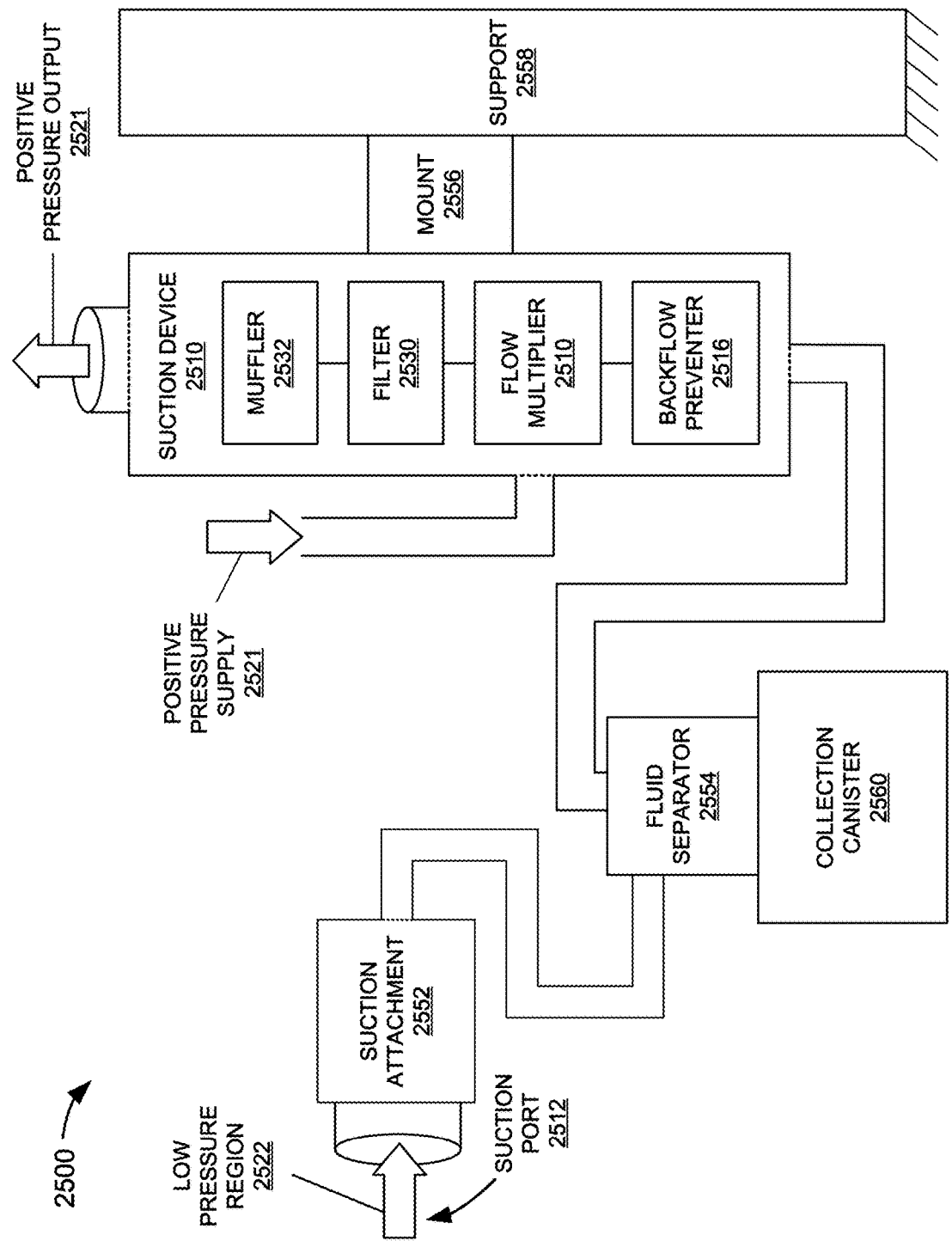
FIG. 25 is a block diagram illustrating a suction system for use in an operating room.

FIG. 25 is a block diagram illustrating suction system for use in an operating room 2500. Suction system 2500 includes suction device 2510, suction attachment 2552, fluid separator 2554, support 2558 and collection canister 2560.

Suction system 2500 includes suction device 2510. Suction device 2510 is an example suction system 100, suction system with backflow prevention 300 (shown in FIG. 25 as 2516), filtering suction system 1000, positive pressure operated suction device 1200, positive pressure operated suction device with backflow prevention 1300, suction device with adjustable pressure gap 1900; however, suction device 2510 includes muffler 2532 and mount 2556.

Suction device 2510 includes muffler 2531. Muffler 2531 is configured to suppress the volume level of positive pressure output 2521. Muffler 2521 includes a plurality of openings configured to direct airflow in a manner that lowers the volume level of positive pressure output 2521.

Suction device 2510 includes mount 2556. Mount 2556 is configured to couple suction device to support 2558. Mount 2556 may be used for hands-free operation of suction device 2510. In some embodiments, mount 2556 may be configured to mount to a pole as frequently used in hospital and operating room environments. In some embodiments, mount 2556 may be configured to couple suction device 2510 to a wall. In some embodiments, mount 2556 may be configured to hang suction device 2510 from an overhead structure.

Suction system 2500 includes suction attachment 2552. Suction attachment is configured to supply low pressure region 2522 to a target area. In some embodiments, suction attachment may be configured for hand-held operation. In some embodiments, suction attachment 2552 may be configured to couple to a surgical instrument. While FIG. 25 illustrates suction attachment 2552 coupled to fluid separator 2554, it should be understood that suction attachment may be directly coupled to suction device 2510.

Suction system 2500 includes fluid separator 2554. Fluid separator 2552 is configured to separate constituents of a flow of matter. The flow of matter may include solids, liquids and gases in varying ratios. Fluid separator 2554 is configured to separate liquids and solids from gas in a flow of matter. Fluid separator 2554 is configured to expel liquids and solids into collection canister 2560. Smoke and gasses are suctioned from fluid separator 2554 by suction device 2510.

Suction system 2500 includes support 2558. Support 2558 can be any structure capable of supporting suction device 2510. In some embodiments, support 2558 may be a pole as commonly found in hospital or operating room environments. In some embodiments, support 2558 may be a wall. In some embodiments, support 2558 may be a structure suspended from a ceiling. Support 2550 may even include a person holding suction device 2510.

Suction system 2500 includes collection canister 2560. Collection canister 2560 is configured to receive liquids and solids from fluid separator 2554. Collection canister 2560 may be used to measure the volume of liquids and solids received, safe disposal of waste or some other purpose.

In operation, suction device 2510 generates low pressure region 2522 using positive pressure supply 2521. Suction generated by suction device 2510 is supplied to fluid separator 2554. Fluid separator 2554 transfers the suction to suction attachment 2552. The suction forms low pressure region 2522 near suction port 2512. A flow of matter (which can include liquids, solids and gasses) is pulled into suction attachment 2552 by low pressure region 2522. The flow of matter is received by fluid separator 2554. Fluid separator 2554 separates liquids, solids and gasses from the flow of matter. Fluid separator 2554 expels the liquids, solids and gasses from the flow of matter into collection canister 2560. Gases from the flow of matter are suctioned from fluid separator 2544 by suction device 2510. Elements from the gasses are removed by filter 2530. A filtrate from filter 2530 is passed through muffler 2532 as positive pressure output 2521.

Figure 24E:
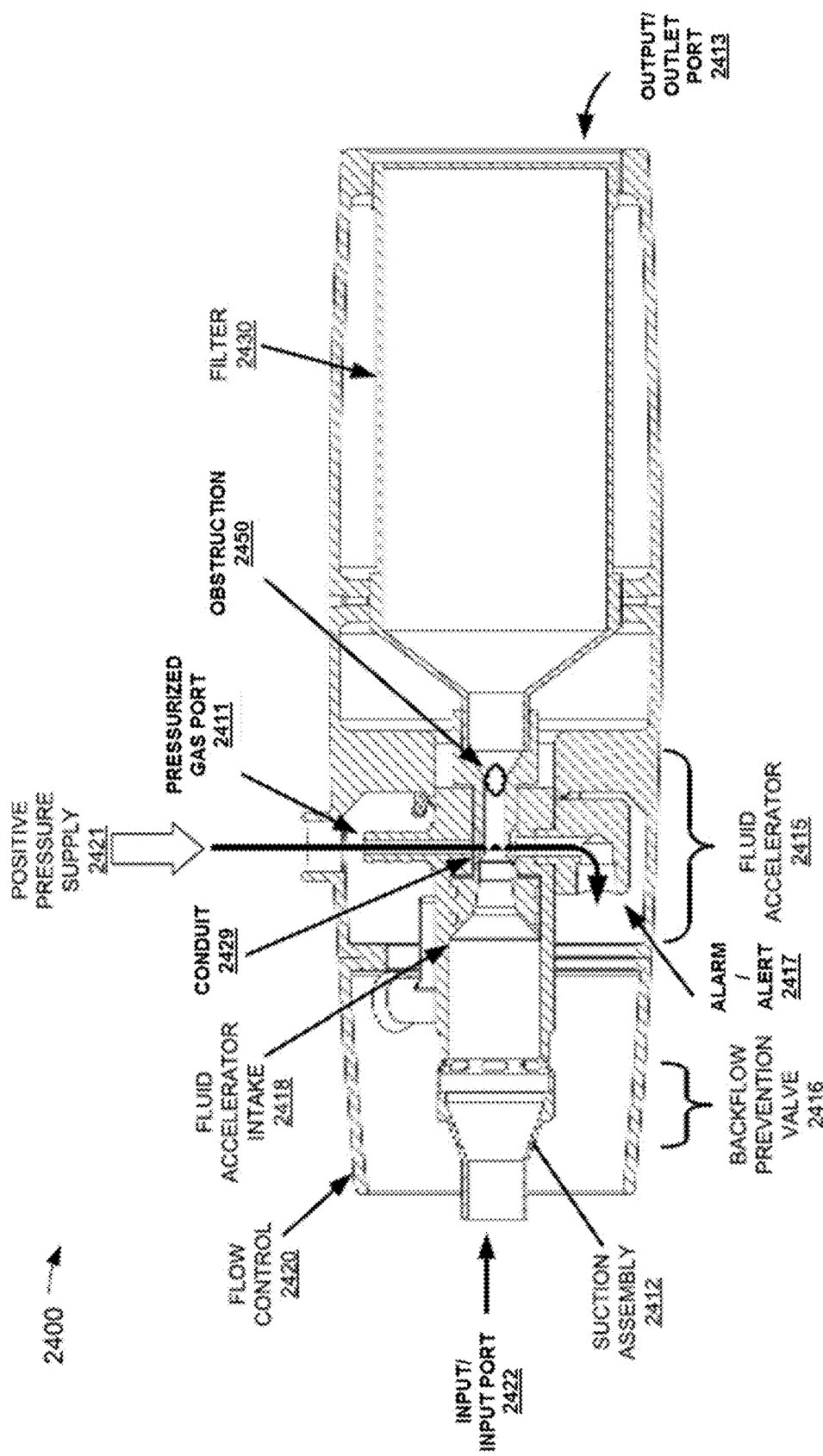
FIG. 24E is a diagram illustrating the operation of a positive pressure operated suction device during normal operation.

FIG. 24E is a diagram illustrating the operation of a positive pressure operated suction device during normal operation. In this example, obstruction 2450 prevents all or a portion of positive pressure supply 2421 from exiting at output/outlet port 2413. Backflow prevention valve 2416 is configured to active in the event that obstruction 2450 prevents all or a portion of positive pressure supply 2421 from exiting at output/outlet port 2413. Backflow prevention valve 2421 may prevent matter from being expelled near input/input port 2422 by positive pressure supply 2421. When backflow prevention valve 2421 is activated, positive pressure supply 2421 is directed through alarm/alert 2417. Alarm/alert 2417 is configured to activate when pressure within suction system 2500 increases to a threshold that is indicative of obstruction 2450 preventing all or a portion of positive pressure supply 2421 from exiting output/outlet port 2413.

Figure 26:
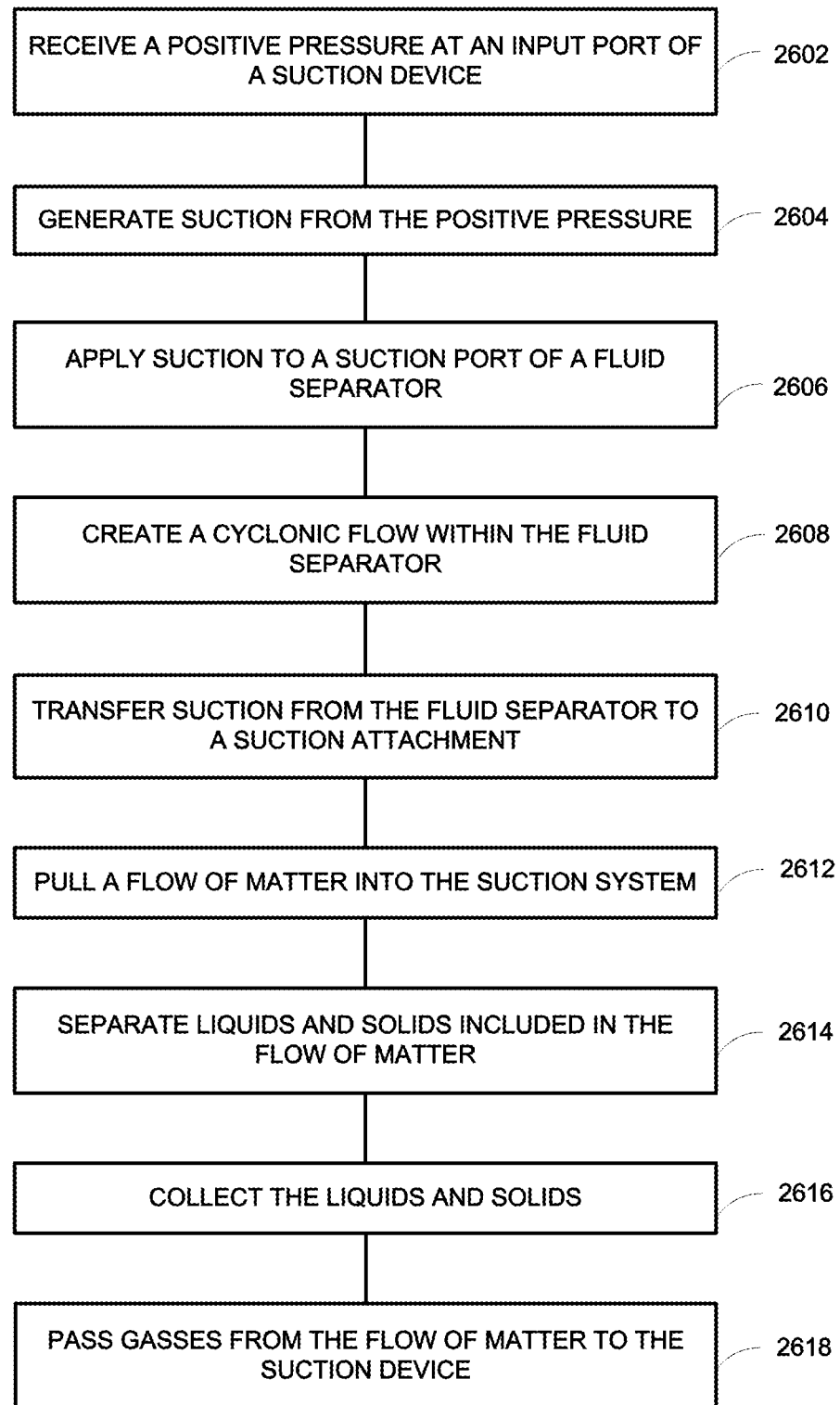
FIG. 26 is a diagram illustrating a method of operating a suction system for use in an operating room.

FIG. 26 is a diagram illustrating a method of operating a suction system for use in an operating room. The steps illustrated in FIG. 26 may be performed by one or more elements of suction system 2500. Positive pressure is received at an input port of a suction device (2602). For example, suction device 2510 is configured to receive positive pressure supply 2521. Suction is generated from the positive pressure (2604). For example, suction device 2510 is configured to generate suction from positive pressure supply 2521. Suction is applied to a suction port of a fluid separator (2606). For example, suction device 2510 is configured to couple to fluid separator 2554. Fluid separator 2554 includes a suction port. Suction device 2510 is configured to apply suction to the suction port of fluid separator 2554. Create a cyclonic flow within the fluid separator (2608). For example, fluid separator 2554 is configured to create a cyclonic flow from suction received from suction device 2510. Suction is transferred from the fluid separator to a suction attachment (2610). For example, fluid separator 2554 is configured to transfer suction from suction device 2510 to suction attachment 2552. Suction from suction device 2510 generates low pressure region 2522 near suction port 2512. A flow of matter is pulled into the suction system (2612). For example, Suction attachment 2552 is configured to receive a flow of matter from low pressure region 2522. Liquids and solids included in the flow of matter are separated (2614). For example, fluid separator 2554 is configured to separate liquids, solids and gasses from a flow of matter. Collect the liquids and solids (2616). Collection canister 2560 is configured to receive liquids and solids. Collection canister 2560 is coupled to fluid separator 2554. Fluid separator 2554 may expel liquids and solids into collection canister 2560. Gasses from the flow of matter are passed to the suction device (2618). Fluid separator 2554 is configured to pass gasses from a flow of matter to suction device 2510. Suction generated by suction device 2510 pull gasses from fluid separator 2554.

Figure 27:
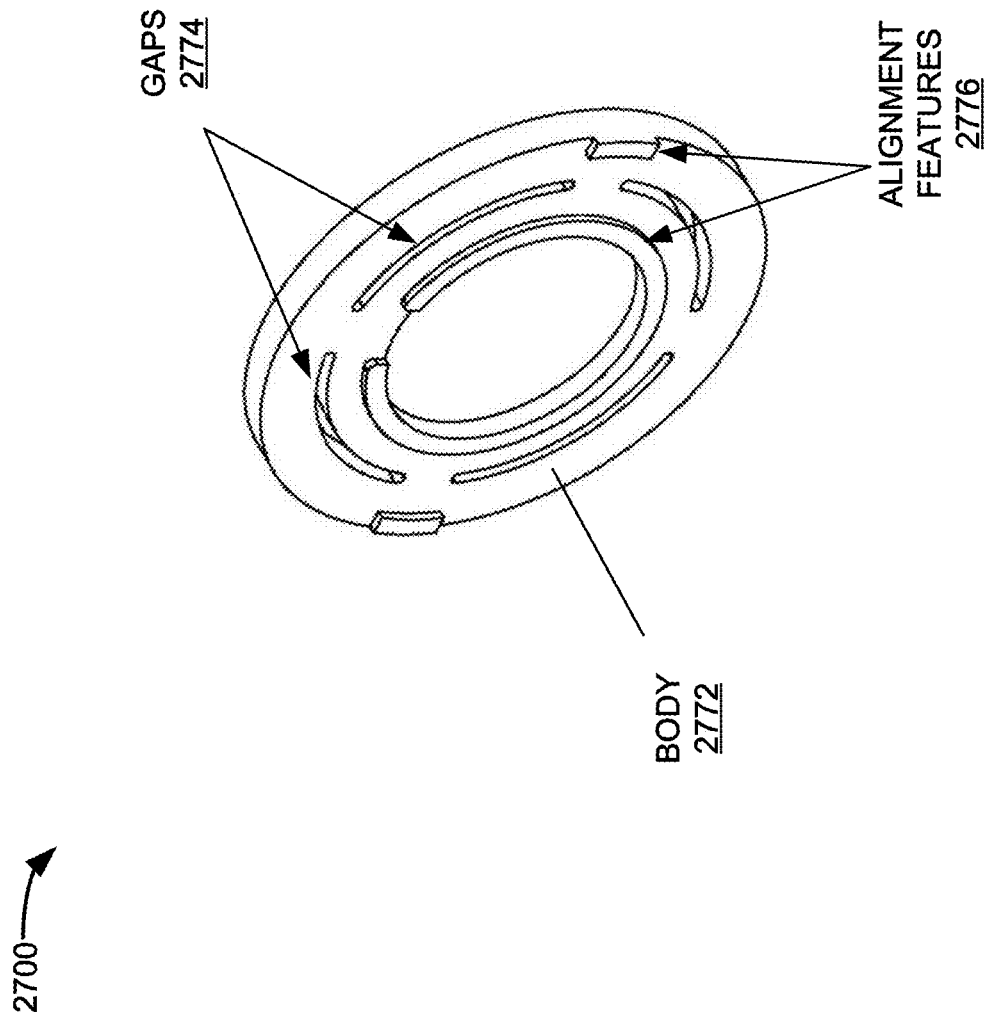
FIG. 27 is a diagram illustrating a muffler for a positive pressure operated suction device.

FIG. 27 is a diagram illustrating a muffler for positive pressure operated suction device 2700. Muffler 2700 includes body 2772, gaps 2774 and alignment features 2776. Muffler 2700 is configured to reduce a volume level of exhaust from a suction device, such as positive pressure operated suction device 2500. The volume level of exhaust is reduced by directing flow paths of the exhaust. Body 2772 is configured couple to the output of a suction device. Body 2772 can be manufactured from a variety of materials including: plastic, metal, glass and ceramic. Muffler 2700 includes gaps 2774. Gaps 2774 are configured to direct flow paths of exhaust from a suction device such that the volume level generated by the exhaust is reduced with respect to undirected flow paths of exhaust. The size and shape of gaps 2774 affects the volume level of exhaust. The size and shape of gaps 2774 may be varied to accommodate various embodiments of suction devices. In some embodiments, gaps 2774 may have a width of 1.5 millimeters. In some embodiments, gaps 2774 may have a width of 2.5 millimeters. Muffler 2700 includes alignment features 2776. Alignment features 2776 are configured to couple to corresponding alignment features on a suction device. Alignment features 2776 may be used to position muffler 2776 with respect to a suction device. In some embodiments, alignment features 2776 may be configured to position muffler 2776 with respect to a filter included in a suction device.

Figure 28:
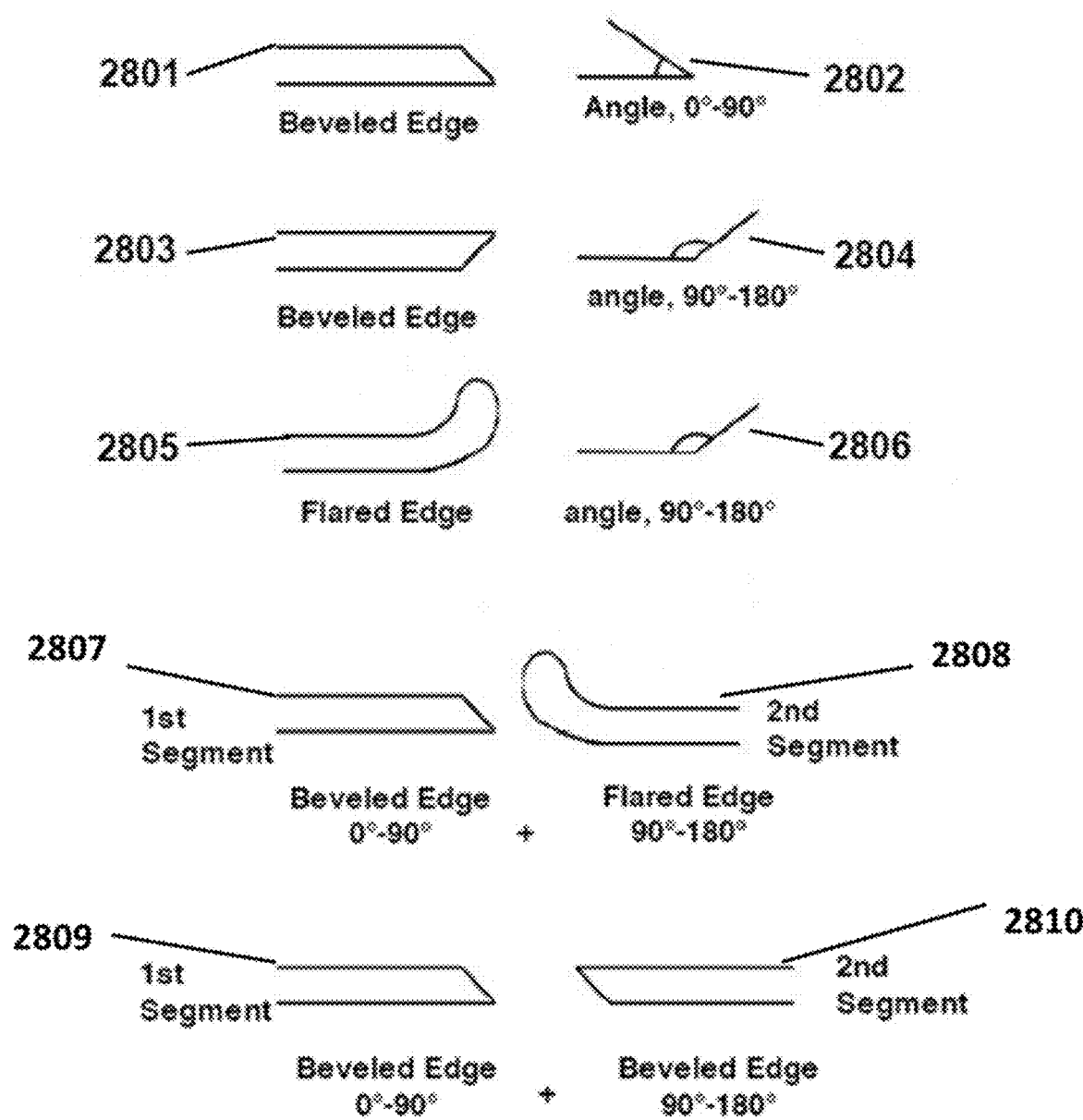
FIG. 28 illustrates the angles of beveled or flared ends that form a conduit when two segments are placed adjacent to one another.

FIG. 28 illustrates a beveled edge of a hollow segment 2801. The beveled edge can form an angle of between 0 degrees and 90 degrees 2802 relative to the segment. FIG. 28 also illustrates a beveled edge of a hollow segment 2803. The beveled edge can form an angle of between 90 degrees and 180 degrees 2804 relative to the segment. FIG. 28 also illustrates a flared edge of a hollow segment 2805. The flared edge can form an angle of between 90 degrees and 180 degrees 2806 relative to the segment. FIG. 28 also illustrates a hollow segment with a beveled edge 2807 in series with a second hollow segment with a flared end 2808, wherein the beveled edge 2807 and flared edge 2808 can be adjacent to one another. The beveled edge can have an angle between 0 degrees and 90 degrees and the flared edge can have an angle between 90 degrees and 180 degrees. FIG. 28 also illustrates a hollow segment with a beveled edge 2809 in series with a second hollow segment with a beveled edge 2810, wherein the two beveled edges are adjacent to one another. The beveled edge of the first hollow segment can have an angle between 0 degrees and 90 degrees and the beveled edge of the second hollow segment can have an angle between 90 degrees and 180 degrees.

FIG. 29 is a table illustrating different device settings and corresponding values of smoke flow rate in standard cubic feet per minute (scfm) and static vacuum in millimeters of mercury (mmHg).

FIG. 30 illustrates the device noise of different devices at 1.5 meters away and 30 psi input pressure. In some embodiments, the device may emit one or more sounds at about 49 decibels. The device may emit one or more sounds at about 6 decibels above a background noise.

Figure 31A:
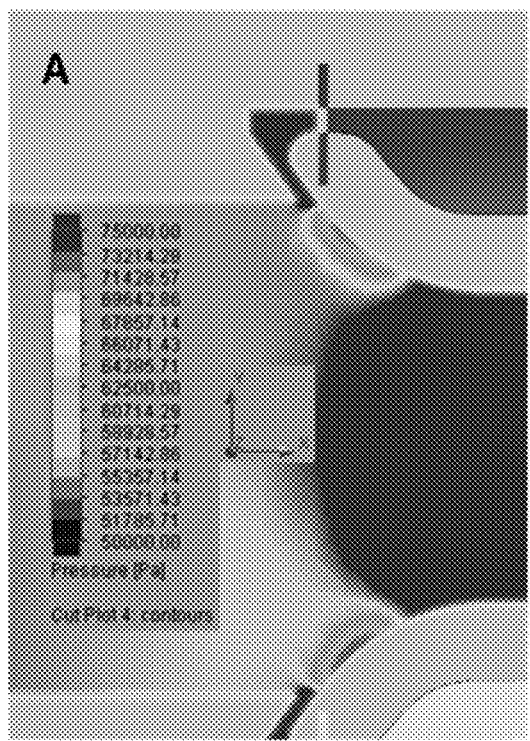
FIG. 31A-B illustrates a computational fluid dynamics (CFD) analysis using a flared end with a 35 degree angle relative to a central axis (FIG. 31A) or a flared end with a 55 degree angle relative to a central axis (FIG. 31B).
Figure 31B:
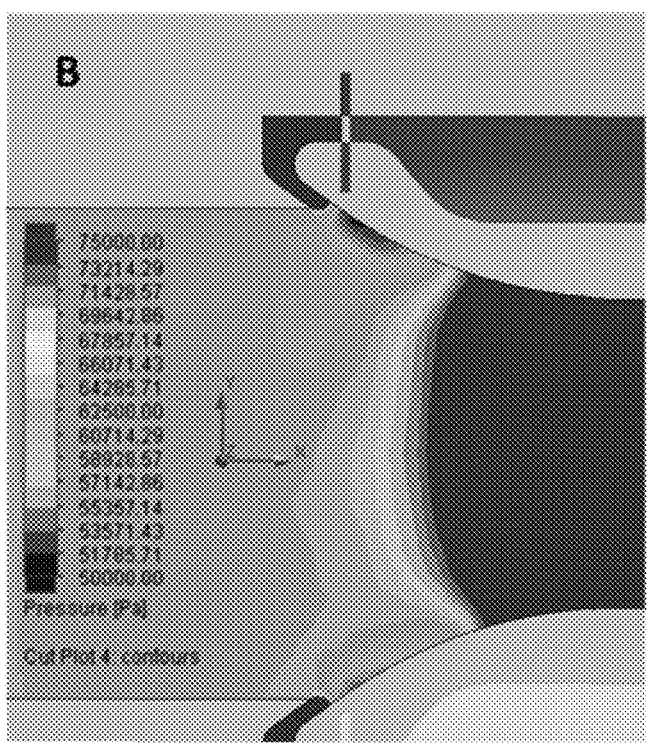

FIG. 31A-B illustrates a computational fluid dynamics (CFD) analysis using a flared end with a 35 degree angle relative to a central axis (FIG. 31A) or a flared end with a 55 degree angle relative to a central axis (FIG. 31B). Altering the angle may increase suction resolution. For example, altering the angle from 35 degrees to 55 degrees may increase the suction resolution by about 20%.

Figure 32:
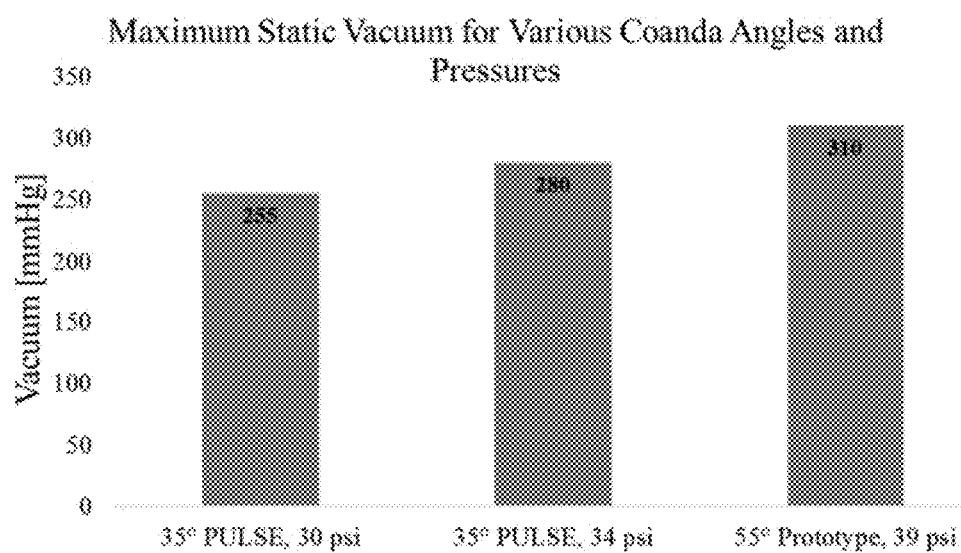
FIG. 32 is a graph illustrating the maximum static vacuum as a function of input pressure at a 35 degree angle relative to a central axis or a 55 degree angle relative to a central axis.

FIG. 32 is a graph illustrating the maximum static vacuum as a function of input pressure at a 35 degree angle relative to a central axis or a 55 degree angle relative to a central axis. Altering the angle may alter the maximum static vacuum. Maximum static vacuum may be between about 250 mmHg and about 260 mmHg for a 35 degree angle relative to a central axis at 30 psi input pressure. Maximum static vacuum may be between about 275 mmHg and about 285 mmHg for a 35 degree angle relative to a central axis at 34 psi input pressure. Maximum static vacuum may be between about 305 mmHg and about 315 mmHg for a 55 degree angle relative to a central axis at 39 psi input pressure.

Figure 33:
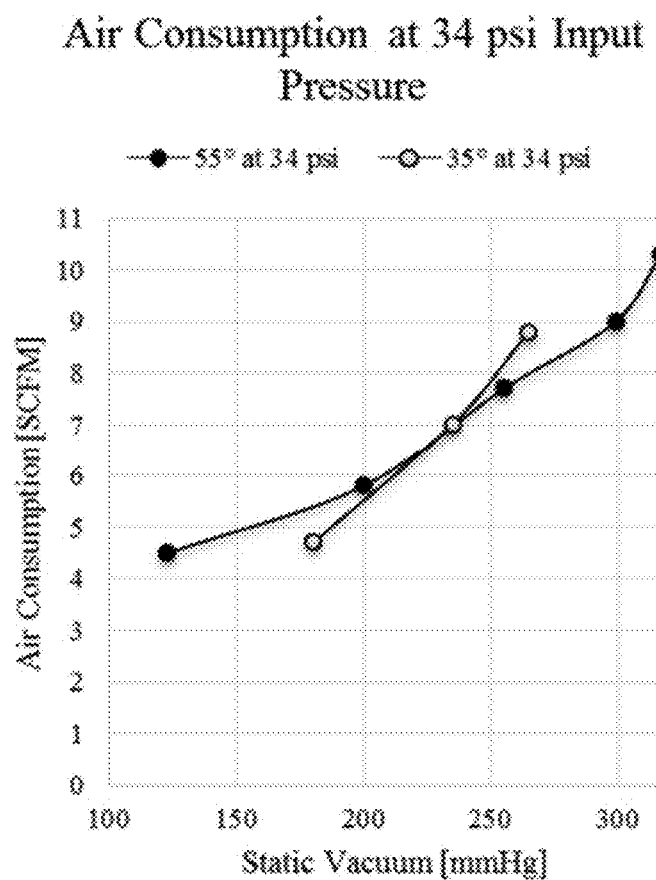
FIG. 33 is a graph illustrating air consumption (scfm) as a function of static vacuum at 34 psi input pressure.

FIG. 33 is a graph illustrating air consumption (scfm) as a function of static vacuum at 34 psi input pressure. Air consumption may be between about 4 scfm and about 11 scfm for a static vacuum of between about 100 mmHg and about 325 mmHg at 34 psi input pressure. Air consumption may be between about 4 scfm and about 9 scfm for a static vacuum of between about 150 mmHg and about 300 mmHg at 34 psi input pressure.

Figure 34:
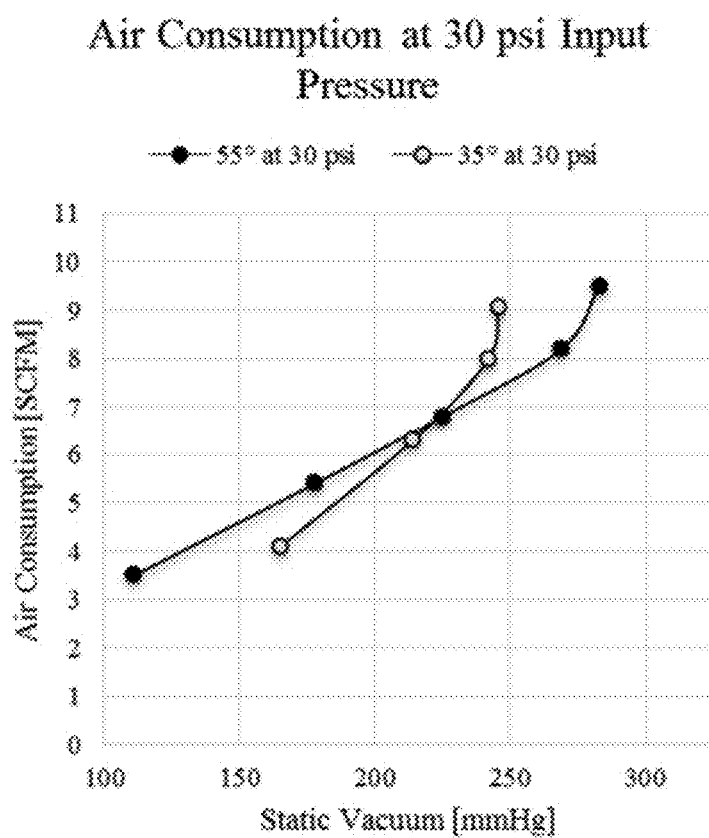
FIG. 34 is a graph illustrating air consumption (scfm) as a function of static vacuum at 30 psi input pressure.

FIG. 34 is a graph illustrating air consumption (scfm) as a function of static vacuum at 30 psi input pressure. Air consumption may be between about 3 scfm and about 10 scfm for a static vacuum of between about 100 mmHg and about 300 mmHg at 30 psi input pressure. Air consumption may be between about 4 scfm and about 9 scfm for a static vacuum of between about 150 mmHg and about 250 mmHg at 30 psi input pressure.

Figure 35:
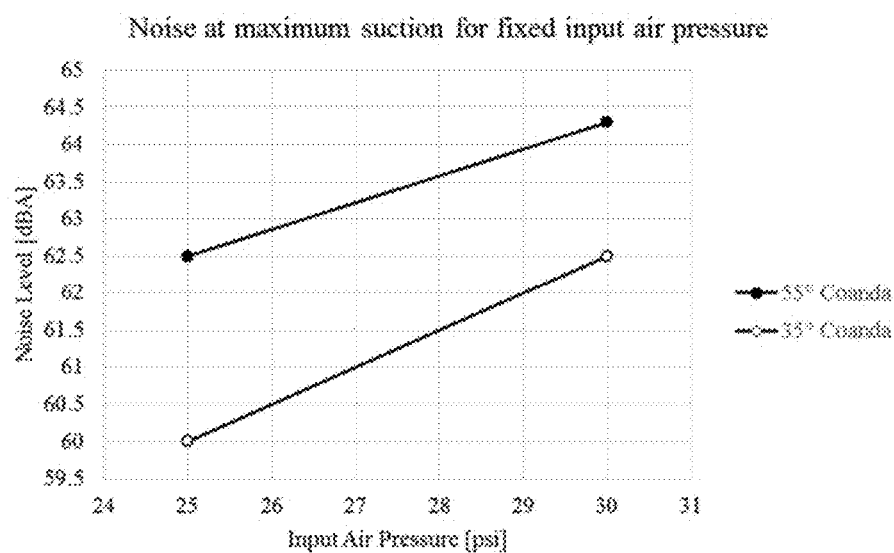
FIG. 35 is a graph illustrating the noise level (dB) at maximum suction as a function of input air pressure in pounds per square inch (psi).

FIG. 35 is a graph illustrating the noise level at maximum suction as a function of input air pressure. Additional air consumption may increase the noise level, such as an increase of about 1 or 2 decibels. A change in a geometry of the device may increase the noise level, such as an increase of about 1 or 2 decibels. A change in a geometry of the device, such as sound baffles or a laminate layer with a micro-surface architecture, may decrease the noise level. A noise level at maximum suction may be about 62.5 dB at 25 psi for a 55 degree angle relative to a central axis or about 60 dB at 25 psi for a 35 degree angle relative to a central axis. A noise level at maximum suction may be about 64.25 dB at 30 psi for a 55 degree angle relative to a central axis or about 62.5 dB at 30 psi for a 35 degree angle relative to a central axis.

Figure 36:
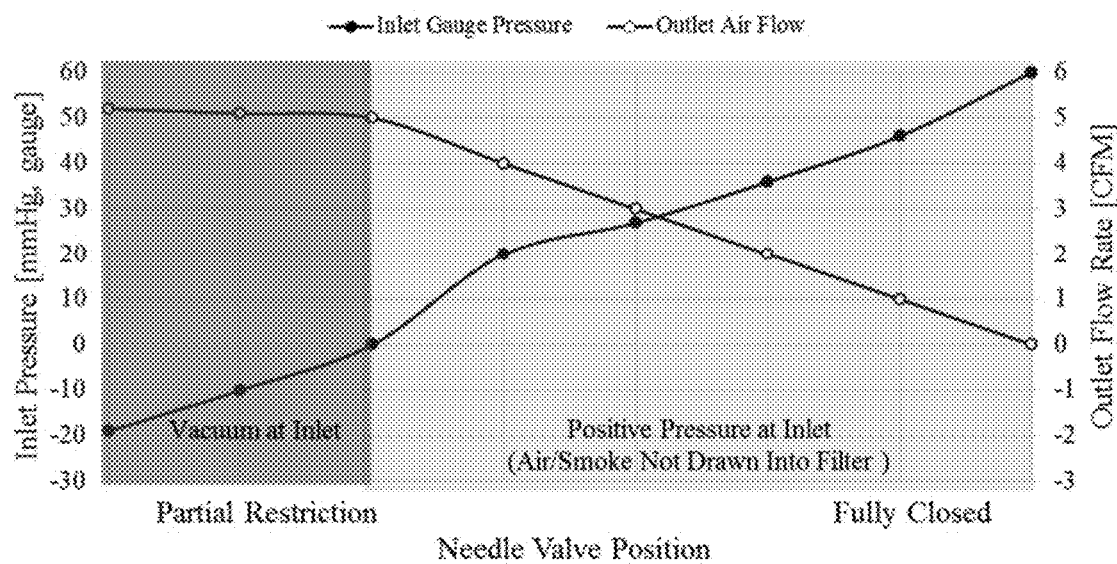
FIG. 36 is a graph illustrating the inlet pressure and outlet flow rate as a function of a simulated filter occlusion.

FIG. 36 is a graph illustrating the inlet pressure and outlet flow rate as a function of a simulated filter occlusion. As the one or more filters partially or completely occludes, the suction generated by the device decreases. In some cases, loss of suction occurs before complete occlusion of the one or more filters. In some cases, it may be possible for a suction flow to fully occlude the one or more filters. In some cases, it may not be possible for a suction flow, such as smoke, to fully occlude the one or more filters.

Figure 37:
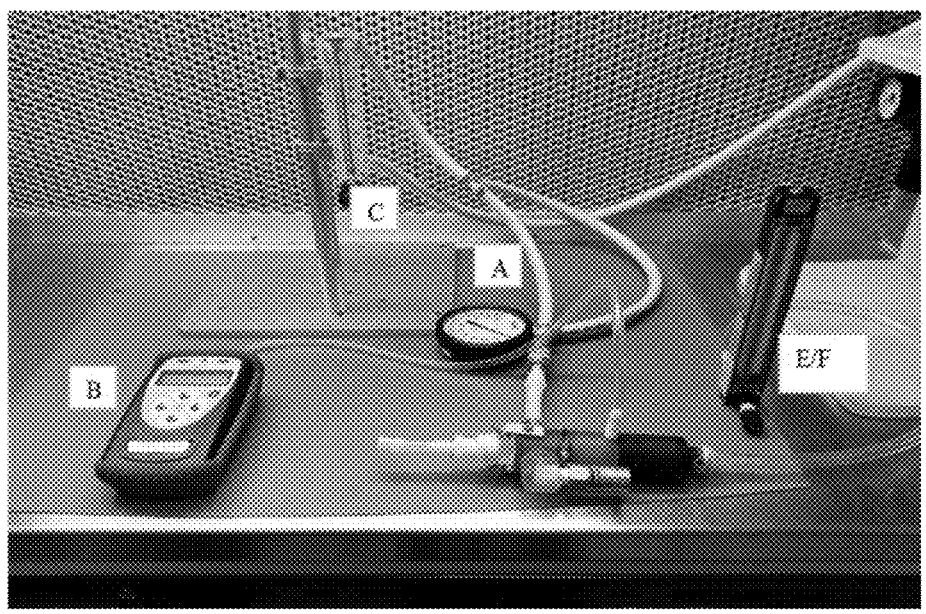
FIG. 37 is an image illustrating the test equipment set up where 37A is a pressure gauge, 37B is a manometer, 37C is a flow meter, 37D is a sound meter, 37E is a flow meter, and 37F is a flow meter.

FIG. 37 is an image illustrating a test equipment set up. FIG. 37A can be a pressure gauge, such as a SPAN 0-100 psi pressure gauge, QMS-596. FIG. 37B can be a manometer, such as a Meriam M2 Series smart manometer, ZM200-DNO200, QMS-689. FIG. 37C can be a flow meter, such as a Key Instruments FR4A67SVVT flow meter. FIG. 37D can be a sound meter, such as an Extech instruments SL130 Sound Meter, QMS-548. FIG. 37E can be a flow meter, such as a Cole-Parmer Model PMR1-010608 0.08-1.25 LPM Flow Meter, S/N 371889-1, QMS-687. FIG. 37F can be a flow meter, such as a Cole-Parmer Model PMR1-0106920 0.5-5LPM Flow Meter, S/N 371889-1, QMS-587 (inactive).

Figure 38:
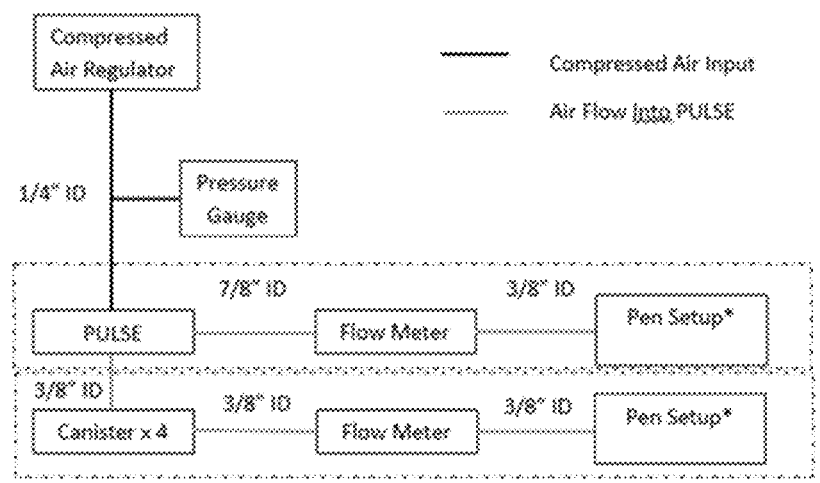
FIG. 38 is a flow diagram illustrating a test equipment set up for air consumption measurement.

FIG. 38 is a flow diagram illustrating a test equipment set up for air consumption measurement. The device can be powered by compressed air, such as from a compressed air regulator. The pressure entering the device can be verified by a pressured gauge, placed, for example, between the air regulator and the device. Air can be drawn into the device through the flow meter and a pen setup. Pressure can be recorded from the pressure gauge at one or more times, and flow rate can be recorded by the flow meter at one or more times. Settings on a tuner arm, for example 0 through 14, may correspondence to the width of the gap space, where 0 on the tuner arm can correspond to 0 inches of width and 14 on the tuner arm can correspond to 0.0115 inches of width. In a first setup, Setup A, to measure air flow, a pen setup can be connected to the device and flow meter with tubing, such as corrugated tubing 4 feet in length with a ⅜ inch internal diameter (ID) and corrugated tubing 6 feet in length with a ⅞ inch ID. In a second setup, Setup B, to measure air and liquid flow, a pen setup can be connected to four canisters with tubing. For example, 4 fluid knock out canisters can be connected to the pen setup with tubing 2 meters long and ⅜ inch ID. The canisters can be connected together with tubing, such as ⅛ inch ID. The canisters can be connected to the device and flow meter with ⅜ inch ID tubing.

Figure 39:
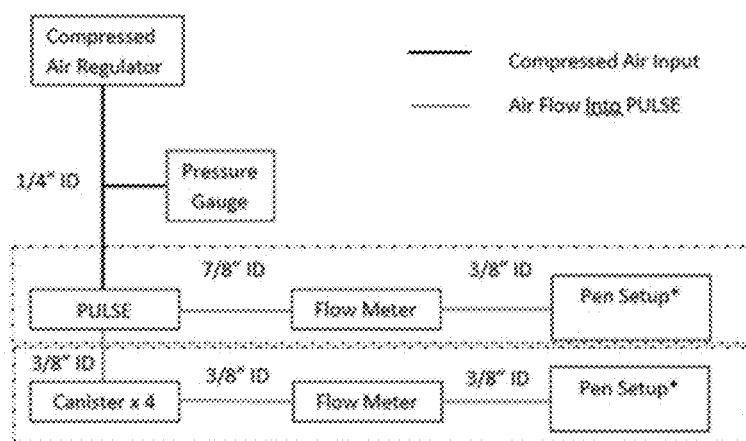
FIG. 39 is a flow diagram illustrating a test equipment set up for static vacuum measurement.

FIG. 39 is a flow diagram illustrating a test equipment set up for static vacuum measurement. The device can be powered by compressed air, such as from a compressed air regulator. The pressure entering the device can be verified by a pressure gauge, placed, for example between the air regulator and the device. The vacuum generated by the device can be recorded with a digital manometer. The maximum vacuum can be recorded by tuning one or both of the input pressure and the gap space of the device to achieve a maximum vacuum.

Figure 40:
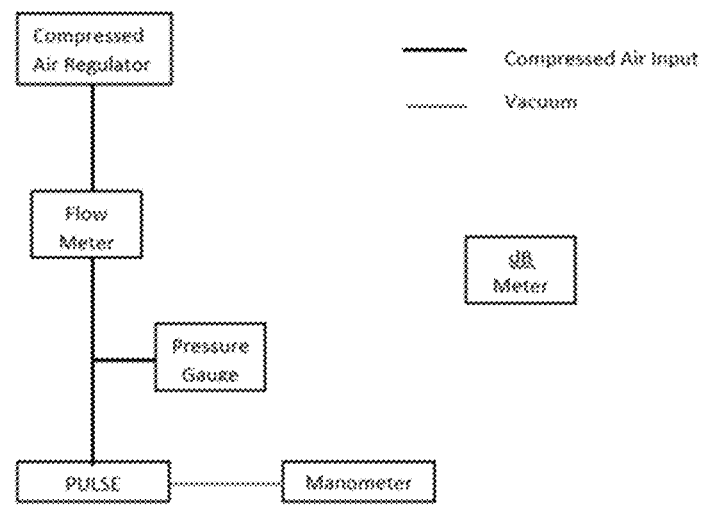
FIG. 40 is a flow diagram illustrating a test equipment set up for static vacuum and noise measurement.

FIG. 40 is a flow diagram illustrating a test equipment set up for static vacuum and noise measurement. The test can be similar to the static vacuum test, however, the flow rate of air into the device can also be measured with a flow meter and device noise can be measured with a decibel meter placed about 1 meter away from the device. The decibel meter can be placed 1.5 meters or more away from the device.

Example

The objective of this study was to determine typical flow rates (cubic feet per minute, cfm) and pressure (millimeters of mercury, mmHg) for fluid evacuation, evacuation of smoke, evacuation of liquid, evacuation of air and liquid and to compare sound levels with typical smoke evacuation units (Rapid VAC, and Conmed AER Defense). Testing was done with a 24131 Rev X9 and an updated shuttle valve (24444 Rev X2). Time was taken from a laptop clock. The air pressure connected to the device was measured with a SPAN 0-100 psi pressure gauge (QMS-596). The tuner arm settings of the device (0 through 14) corresponded to a gap space of 0 inches to 0.0115 inches. The vacuum was the vacuum relative to atmosphere at the outlet of the flow meter (when connected), and it was measured with a Meriam M2 Series smart manometer, P/N ZM200-DNO200, QMS-689. The ΔP was the pressure drop across the flow meter when connected, and it was measured with a Meriam M2 Series smart manometer, P/N ZM200-DNO200, QMS-641. The flow rate of air into the device was measured at the device inlet with a Key Instruments FR4A67SVVT flow meter. The sound was measured by an Extech Instruments SL130 Sound Meter, QMS-548. The results are tabulated in FIGS. 41-44.

Figure 43:
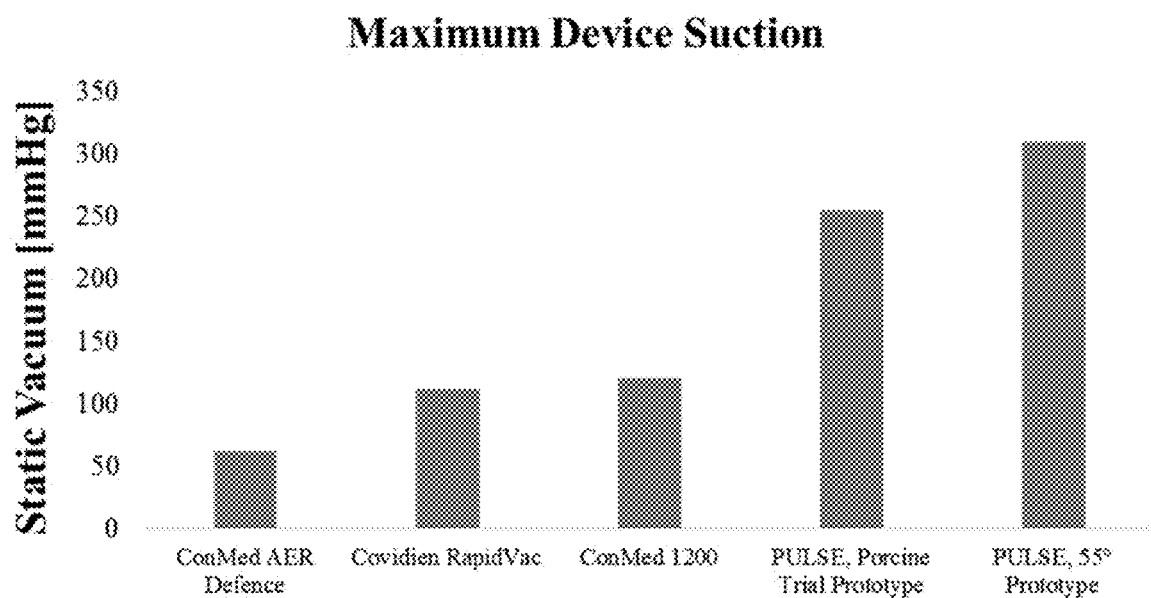
FIG. 43 is a graph illustrating maximum static vacuum (mmHg) in the porcine trial.

FIG. 41 is a table illustrating different device conditions for smoke evacuation in the porcine trial. FIG. 42 is a table illustrating maximum static vacuum (mmHg) in the porcine trial. FIG. 43 is a graph illustrating maximum static vacuum (mmHg) in the porcine trial. FIG. 44 is a table illustrating the auditory noise level in decibels (dB) as a function of maximum static vacuum (mmHg) in the porcine trial.

The various embodiments described herein operate from a pressure source that is above an ambient air pressure. This pressure source may be supplied by a compressed air canister, an air compressor or even a human breath. In battlefield applications, or other situations where electricity is not available, the suction devices presented herein may be operated without electricity by supplying a pressure above an ambient air pressure. In the field a compressed air cylinder may provide pressure. Alternatively, in an emergency, the suction devices presented herein may operate from a human breath. A traditional suction device that operates by a vacuum source may present danger to a human being if they were to use their breath to provide suction. A person providing suction may inhale blood, bodily fluids, tissue or other undesirable elements. This risk is eliminated if a person can generate suction by blowing.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

What is claimed is:

1. A passive suction device comprising:
   a first hollow segment having a central axis, wherein the first hollow segment comprises an inlet port configured to receive a gas, a liquid, a solid or any combination thereof;
   a first opening; and
   a beveled edge at the first opening, the beveled edge comprising a first facing surface comprising a central axis surface and an angled surface with an interior wall therebetween, the central axis surface and the angled surface forming an angle less than 90 degrees;
   a second hollow segment comprising
   an outlet port configured to release the gas, the liquid, the solid or any combination thereof;
   a second opening facing the first opening; and
   a second facing surface positioned at the second opening and facing the first facing surface; and
   an airflow amplifier comprising:
   a pressurized gas port configured to receive a pressurized gas flow; and
   a conduit having its interior surface formed by the first facing surface and the second facing surface, wherein the conduit is in fluid communication with the pressurized gas port, and wherein the conduit is configured to receive the pressurized gas flow and direct the pressurized gas flow into the second opening such that the pressurized gas flow through the second opening generates an area of low pressure which generates a suction flow causing the inlet port to receive the gas, the liquid, the solid, or the combination thereof; and
   a backflow prevention valve configured to prevent backflow of the gas, the liquid, or the combination thereof comprising a sliding body and a diaphragm, wherein the sliding body is configured to move along the central axis within the device when acted upon by pressure transferred from a pressure source via the diaphragm to the sliding body, and the diaphragm is configured to move with respect to the sliding body.

2. The device of claim 1, further comprising an alarm configured to activate in the presence of a backflow of the gas, the liquid, or the combination thereof.

3. The device of claim 2, wherein an alarm port is in fluid communication with the first segment.

4. The device of claim 1, further comprising a filter configured to filter the gas, the liquid, the solid, or the combination thereof.

5. The device of claim 1, further comprising a tuner arm configured to adjust a width of the conduit, wherein the tuner arm is configured to move one or more of the first hollow segment and the second hollow segment relative to each other thus changing a distance between the first facing surface and the second facing surface.

6. The device of claim 5, wherein the width of the conduit is adjustable between 0 millimeters (mm) and 2 mm.

7. The device of claim 1, further comprising an angle adjustment controller, wherein the angle adjustment controller is configured to adjust the angle.

8. The device of claim 1, wherein the angle is between 20 degrees to 60 degrees.

9. The device of claim 1, wherein an end of the second hollow segment that is facing the first hollow segment is rounded.

* * * * *